United States Patent
McDonald et al.

(12) 
(10) Patent No.: US 6,602,693 B1
(45) Date of Patent: Aug. 5, 2003

(54) GENE ENCODING HYALURONAN SYNTHASE

(75) Inventors: John A. McDonald, Scottsdale, AZ (US); Andrew P. Spicer, Scottsdale, AZ (US); Mary Louise Augustine, Scottsdale, AZ (US)

(73) Assignee: Clear Solutions Biotech, Inc., Stony Brook, NY (US)

( * ) Notice: Subject to any disclaimer, the term of this patent is extended or adjusted under 35 U.S.C. 154(b) by 0 days.

(21) Appl. No.: 08/812,008

(22) Filed: Mar. 5, 1997

Related U.S. Application Data

(63) Continuation of application No. 08/675,499, filed on Jul. 3, 1996, now Pat. No. 6,492,150.

(51) Int. Cl.$^7$ .............................. C12N 9/00; C12N 1/20; C07H 21/04
(52) U.S. Cl. ................. 435/183; 435/320.1; 435/252.3; 435/254.11; 435/325; 435/410; 536/23.1; 536/23.2
(58) Field of Search ............................. 536/23.2, 23.1, 536/72.1; 435/320.1, 252.3, 254.11, 325, 410, 183

(56) References Cited

PUBLICATIONS

Sigma Catalog (1993) Catalog No. A 2383. p. 48, Jan. 1993.*

Balazs, E.A., et al., "Matrix Engineering", *Blood Coagulation and Fibrinolysis*, 2, 173–178, (1991).

DeAngelis, P.L., et al., "Immunochemical Confirmation of the Promary Structure of Streptococcal Hyaluronan Synthase and Synthesis of High Molecular Weight Product by the Recombinant Enzyme", *Biochemistry*, 33, 9033–9039, (Aug., 1994).

DeAngelis, P.L., et al., "Molecular Cloning, Identification, and Sequence of the Hyaluronan Synthase Gene from Group A Streptococcus pyogenes", *J. Biol. Chem.*, 268, 19181–19184, (Sep., 1993).

Itano, N., et al., "Expression Cloning and Molecular Characterization of HAS Protein, a Eukaryotic Hyaluronan Synthase", *J. Biol. Chem.*, 271, 9875–9878, (Apr., 1996).

Laurent, T.C., et al., "Hyaluronan", *FASEB. J.*, 6, 2397–2404, (1992).

Meyer, M.F., et al., "Cells Expressing the DG42 Gene from Early Xenopus Embryos Synthesize Hyaluronan", *Proc. Natl. Acad. Sci., USA*, 93, 4543–4547, (May, 1996).

O'Regan, M., et al., "Molecular Mechanisms and Genetics of Hyaluronan Biosynthesis", *Int. J. Biol. Macromol.*, 16, 283–286, (1994).

Semino, C.E., et al., "Homologs of the Xenopus Developmental Gene DG42 are Present in Zebrafish and Mouse and Are Involved in the Synthesis of Nod–Like Chitin Oligosaccharides During Early Embryogenesis", *Proc. Natl. Acad. Sci., USA*, 93, 4548–4553, (May, 1996).

Varki, A., "Does DG42 Synthesize Hyaluronan or Chitin?: A Controversy About Oligosaccharides in Vertebrate Development", *Proc. Natl. Acad. Sci., USA*, 93, 4523–4225, (May, 1996).

Wilson, R.K., "Nucleotide sequence, SW:DG42–Xenla P13563 DG42 Protein, dbEST Id. No: 528557", *GenBank Accession No: W21505*, (May 1996).

Watanabe et al., Molecular Identification of a Putative Human Hyaluronan Synthase, Journal of Biological Chemistry 271(38): 22945–22948, Sep. 1996.*

Hillier, L., et al., Accession No. W21505 "The WashU–Merck EST Project", *HTTP://www.ncbi.nlm.nih.gov unpublished* (*1995*), 2.

* cited by examiner

Primary Examiner—Rebecca E. Prouty
Assistant Examiner—Richard Hutson
(74) Attorney, Agent, or Firm—Schwegman, Lundberg, Woessner & Kluth, P.A.

(57) ABSTRACT

An isolated and purified DNA molecule encoding hyaluronan synthase-2 (Has2) is provided, as is purified and isolated Has2 polypeptide. Also provided is an isolated and purified DNA molecule encoding hyaluronan synthase-3 (Has3), as is purified and isolated Has3 polypeptide.

24 Claims, 25 Drawing Sheets

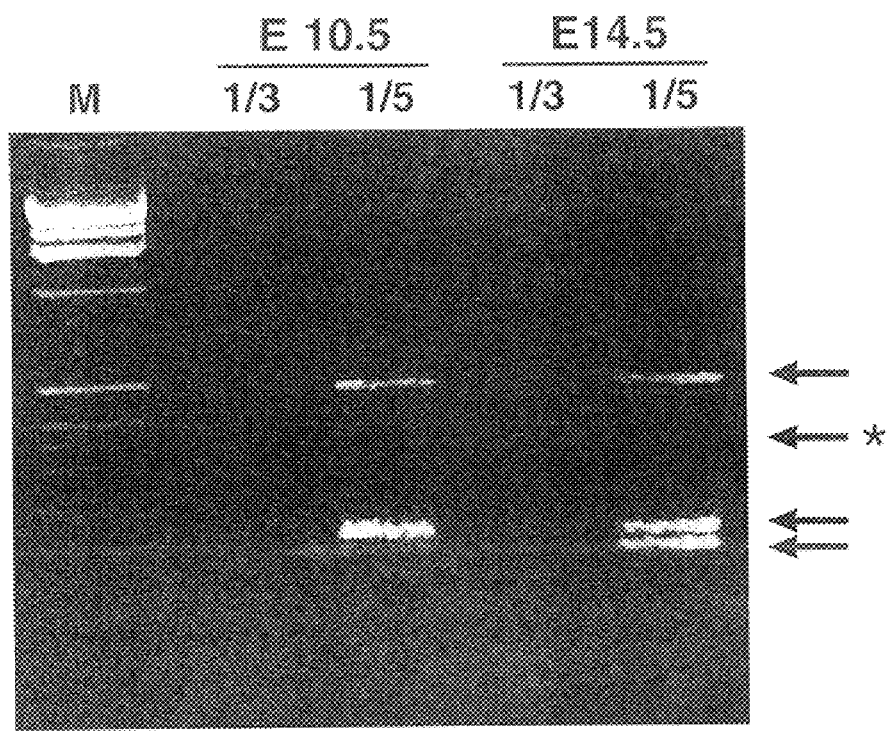
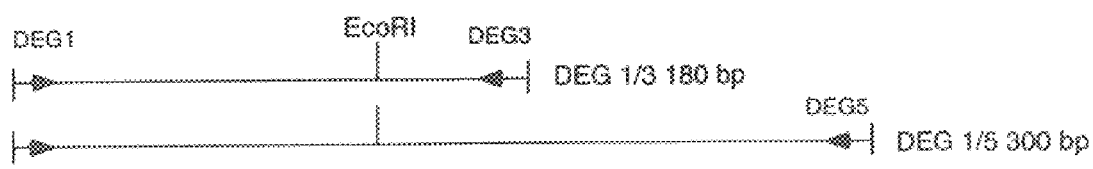
Fig. 1

```
   1  acatgtaagaagaaggagaagtcaaggcgctctggaagaattaccagtcctgcttcgagcagcccattga
  73  acggggacttgaaccagccaaagactccttcattctgctcttgactctgctgagtcttgacccggct
 145  tgtaggttgatgtgtgaaaagagattttgtgtcgtcggagggaaggattggagcaaatagcaaacaggggg
 217  aaaagttaattatctttaaagcagataacaaagaagaattagaagacttaagtgcagcggaaatatttttaaat
 289  aatattagtgaaatttctcttcctcaaagagagggagaaccaagcattaaggctcccatcttttttaat
 361  gttgttttaaatttctttattttttggccgtcgtctcaaattcatctgattctcttattgagcaggctgaac
 433  ggaaacttcctccgacccctccgggaccacacagaggcggaggagtctatgagcagagctgaac
 505  aagATGCATTGTGAGAGGTTTCTATGTGTCCTAGTTTATCCAAACAGATAATTACTACTTCTCATTTGGA        23
                M  H  C  E  R  F  L  C  V  L  R  I  I  G  T  T  L  F  G  V  S  L  L
 577  CTCGGAATCACAGCTGCTTATATTGTTGGCTACCAGTTTATCCAAACAGATAATTACTACTTCTCATTTGGA      47
           L  G  I  T  A  A  Y  I  V  G  Y  Q  F  I  Q  T  D  N  Y  Y  F  S  F  G
 649  CTGTACGGTGCCTTTTTAGCCTCGCATCTCATCATCCAAAGCCTCTTTGCCTTTGCCTTTGAACACCGGAAAATG   71
           L  Y  G  A  F  L  A  S  H  L  I  I  Q  S  L  F  A  F  L  E  H  R  K  M
 721  AAGAGTCCCTGAAATCTGAAATGTTTGCAATCTGTGAAAAGGCTGACCTACCCTGGGATTAAAGTCGTGATGGTC   95
           K  S  L  E  T  P  I  K  L  N  K  T  V  A  L  C  I  A  A  Y  Q  E  D
 793  CCTGACTACTTACGGAAACTCAGACGACGACCTTTACATGATGAACATATTCAGCGAAGTTATTGGCAGGGACAAATCG 119
           P  D  Y  L  R  K  C  L  Q  S  V  K  R  L  T  Y  P  G  I  K  V  V  M  V
 865  ATCGATGGGAACTCAGACGACGACCTTTACATGATGGACATATTCAGCGAAGTTATTGGCAGGGACAAATCG    143
           I  D  G  N  S  D  D  D  L  Y  M  M  D  I  F  S  E  V  I  G  R  D  K  S
 937  GCCACGTACATCTGGAAGAACAACTTTCATGAAGGGACCTGGTGAGACAGAAGAGTCCCATAAAGAAAGT        167
           A  T  Y  I  W  K  N  N  F  H  E  K  G  P  G  E  T  E  E  S  H  K  E  S
1009  TCACAACATGTCACCCAGTCTTGTCTTAACAAAGTATTTGCATCATCATCAAAAATGGGTGGAAAGAGA       191
           S  Q  H  V  T  Q  L  V  L  S  N  K  S  I  C  I  M  Q  K  W  G  G  K  R
1081  GAAGTCATGTACACAGCCTTCAGAGCACTGGGGCGAAGCGTGGATTATGTACAGGTGTGTGACTCAGATACT    215
           E  V  M  Y  T  A  F  R  A  L  G  R  S  V  D  Y  V  Q  V  C  D  S  D  T
1153  ATGCTTGACCCTGCCTCATCTGTGGAGATGGTGAAGGTCTTAGAGGAAGACCCTATGGTTGGAGGTGTTGGA     239
           M  L  D  P  A  S  S  V  E  M  V  K  V  L  E  E  D  P  M  V  G  G  V  G
1225  GGAGATGTCCAGATTTTAAACAAGTATGATTCCTCAGCAGCGTGAGATACTGGATGGCT
```

Fig.3-1

```
             G   D   V   Q   I   L   N   K   Y   D   S   W   I   S   F   L   S   S   V   R   Y   W   M   A
1297  TTTAATATAGAAAGGGCCTGCCAGTCTTATTTGGCTGTGTCCAGTGCATAAGCCGGTCCTCTGGAATGTAC     263
         F   N   I   E   R   A   C   Q   S   Y   F   G   C   V   Q   C   I   S   G   P   L   G   M   Y
1369  AGAAACTCCTTGCTGCATGAATTTGTGGAAGACTGGTACAATCAGGAATTCATGGGTAACCAATGCAGTTTT     287
         R   N   S   L   H   E   F   V   E   D   W   Y   N   Q   E   F   M   G   N   Q   C   S   F
1441  GGTGACGACAGGCACCTTACCAACAGGGTGTTGAGTCTGGGCTATGCAACTAAATACACGGCTCGGTCCAAG     311
         G   D   D   R   H   L   T   N   R   V   L   S   L   G   Y   A   T   K   Y   T   A   R   S   K
1513  TGCCTTACTGAAACTCCCATAGAATATCTGAGATGGCTGAACCAGACCCGATGGAGCAAGTCCTACTTC      335
         C   L   T   E   T   P   I   E   Y   L   R   W   L   N   Q   T   R   W   S   K   S   Y   F
1585  CGAGAGTGGCTGTACAATGCCATGTGGTTTCACAAGCATCACCTGTGATGACCTATGAAGCTGTTATCACT    359
         R   E   W   L   Y   N   A   M   W   F   H   K   H   H   L   W   M   T   Y   E   A   V   I   T
1657  GGATTCTTTCCTTTCTTTCTCATTGCCACAGTCATCCAGCTCTTCATCAAGTCATCTTTTGCCTTAGAGAAATATCCTC    383
         G   F   F   P   F   F   L   I   A   T   V   I   Q   L   F   Y   R   G   K   I   W   N   I   L
1729  CTCTTCCTGTTAACTGTCCAGCTAGTGGGTCTGTATTCAGTGTTATACATGTCAAGTCTCTACTTCCTGCCAAGATGTTTGCAATT    407
         L   F   L   L   T   V   Q   L   V   G   L   I   K   S   S   F   A   S   C   L   R   G   N   I
1801  GTCATGGTATTCATGTCTCTGTATTCAGTGTTATACATGTCAAGTCTCTTGTTATACATGTCTTGCCAAGATGTTTGCAATT    431
         V   M   V   F   M   S   L   Y   S   V   L   Y   M   S   S   L   L   P   A   K   M   F   A   I
1873  GCAACCATAAAACAAAGCTGGGTGGGGCACATCTGGAAGGAAGACCATTGTTTAATTTCATAGGACTTATT     455
         A   T   I   N   K   A   G   W   G   T   S   G   R   K   T   I   V   N   F   I   G   L   I
1945  CCAGTGTCCGTGTGGTTTACAATCCTTCTAGGTGGTGTAATTTTCACCATTTATAAGGAATCTAAAAAGCCA    479
         P   V   S   V   W   F   T   I   L   L   G   G   V   I   F   T   I   Y   K   E   S   K   K   P
2017  TTTTCCGAATCCAAACAGACTGTTCTCATCGTTGGGAACTTTGATCGTATGCATGCTACTGGGTCATGCTTTTG    503
         F   S   E   S   K   Q   T   V   L   I   V   G   T   L   I   Y   A   C   Y   W   V   M   L   L
2089  ACTCTCTATGTGGTTCTCATCAATAAGTGTGGCAGGCGGAAGAAGGACAACAGTATGACATGGTGCTTGAT    527
         T   L   Y   V   V   L   I   N   K   C   G   R   R   K   K   G   Q   Q   Y   D   M   V   L   D
2161  GTA TGAtgatgtttgtagtcacacctggagacacacacatcacacacacaccttagctc                552
         V   *
```

Fig.3-2

```
2232  ctcaaggggctatacagtattgtggcaccgcacctgccaccacaggagacatatcactgctgctgggactt
2304  gaacaaagacattcaatggggtggtttctttttattctgccaaagcaaattgatacatcagtgagaaga
2376  aagtccgattaaatctgacagtttaggacgtgggatgtcttggcttatgcactttcccttactgtg
2448  catctgcctgacagtgttgttctaaatacctcacttgccatgcttgtgtgggtgatcatgaagaaagg
2520  attctgaaaactcaaggaacgttcttcaacctacacatcctaacttatgactctttgatagctgatga
2592  tttctttctattttttgtttttaaggaaaattgttcatcttttaccaaatgaaatgccaaggaaagttgga
2664  aagccactggctatgctgtatttgatatttactgtgttttaaattttgtatccggatttaaa
2736  aacaaaatttcacaccatagtctatattttactctctggcaaaatacacttttgttctttttatatat
2808  atatatatataataggttctaaaaaatccatactataaaaaattaacctgcccaaatgtg
2880  aaacgtggttgactgattgttcatgaaagaataaatgttttctctttctttctctacattttaaaaaaa
```

Fig.3-3

```
MHas2  -MHCERFLCVLR-IIGTTL------------------FGVSLLLGITAVYIVGYQFIQTDNYYFSFGLYGAFL
MHas1  ----MRQDMPKPSEAARCCSGLARRALTII---FALLIGLMTWAYAAGVPLASDRYGLLAFGLYGAFL
DG42   MKEKAAETMEIPEGIPKDLEPKHPTLWRIIYYSFGVLLATITAAYVAEFQVLKHEAILFSLGLYGLAM
HasA   --------MPIFKKTLIVLSFIFLISILIYLNMYLFGTST---VGI-YGVILITYLVIKL------GLSF
NodC   -----------------------MYLLDTTTSTAAISI-YALLLTAYRSMQVLYARPIDGLAV
                                                                *

MHas2  ASHLIIQSLFAFLEHRKM----KKSLETPIKLNKT---VALCIAAYQEDPDYLRKCLQSVKRLTYPGIK
MHas1  SAHLVAQSLFAYLEHRRVAAAARRSLAKGPLDAATARSVALTISAYQEDPAYLRQCLTSARALLYPHTR
DG42   LLHLMMQSLFAFLEIRRV----NKSEL-PCSFKKT---VALTIAGYQENPEYLIKCLESCKYVKYPKDK
HasA   LYEPFKGNPHDY-------------------------KVAAVIPSYNEDAESLLETIKSVLAQTYPLS-
NodC   AAEPVETRPLP--------------------------AVDVIVPSFNEDPGILSACLASIADQDYPGE-
         **                                         *

MHas2  --VVMVIDGNSDDDLYMMDIFSEVIGRDKSATYIWKNNFHE-KGPGET--------EESHKESSQHVTQ-
MHas1  LRVLMVVDGNRAEDLYMVDMFREVFADEDPATYVWDGNYHQPWEPAEATGAVGEGAYREVEAEDPGRLA
DG42   LKIILVIDGNTEDDAYMMEMFKDVFHGEDVGTYVWKGNYHTVKKPEETNKGSCPEVSKPLN-EDEGINM
HasA   -EIYIVDDGSSNTDAIQL--------------IEEYVNRE------------VDICRNVIVHRS--
NodC   LRVYVVDDGSRNREAIVR--------------VRAFYSRD------------PRFSFILLPE----
          ***                         *

MHas2  ---LVLSNKSICIMQKWGGKREVMYTAFRALGRSVDYVQVCDSDTMLDPASSVEMVKVLEEDPMVGGVG
MHas1  VEALVRTRRCVCVAQRWGGKREVMYTAFKALGDSVDYVQVCDSDTRLDPMALLELVRVLDEDPRVGAVG
DG42   VEELVRNKRCVCIMQQWG-KREVMYTAFQAIGTSVDYVQVCDSDTKLDELATVEMVKVLESNDMYGAVG
HasA   ---LVNK--------G-KRHAQAWAFERSDADV-FLTV-DSDTYIYPNALEELLKSFNDETVYAATG
NodC   ----NV---------G-KRKAQIAAIGQSSGDL-VLNV-DSDSTIAFDVVSKLASKMRDPEVGAVMG
                       *                    *                        **

MHas2  GCVQILNKYDSWISFLSSVRYWMAFNIERACQSYFGCVQCISGPLGMYRNSLLHEFVEDWYNQEFMGNQ
MHas1  GDVRILNPLDSWVSFLSSLRYWVAFNVERACQSYFHCVSCISGPLGLYRNNLLQQFLEAWYNQKFLGTH
DG42   GDVRILNPYDSFISFMSSLRYWMAFNVERACQSYFDCVSCISGPLGMYRNNILQVFLEAWYRQKFLGTY
HasA   -HLNARNRQTNLLTRLTDIRYDNAFGVERAAQSLTGNILVCSGPLSIYRREVIPNLERYKNQTFLGLP
NodC   -QLTASNSGDTWLTKLIDMEYWLACNEEERAAQSRFGAVMCCCGPCAMYRRSALASLLDQYETQLFRGKP
                                                               **
```

Fig. 4-1

```
MHas2    CSFGDDRHLTNRVLSLGYATKYTARSKCLTETPIEYLRWLNQQTRWSKSYFREWLYNAMWFHKHHL-------
MHas1    CTFGDDRHLTNRMLSMGYATKYTSRSRCYSETPSSFLRWLSQQTRWSKSYFREWLYNALWWHRHHA-------
DG42     CTLGDDRHLTNRVLSMGYRTKYTHKSRAFSETPSLYLRWLNQQTRWTKSYFREWLYNAQWWHKHHI-------
HasA     VSIGDDRCLTNYAIDLG-RTVYQSTARCDTDVPFQLKSYLKQQNRWNKSFFRESIISVKKILSNPIVAL
NodC     SDFGEDRHLTIIMLKAGFRTEYVPDAIVATVVPDTLKPYLRQQLRWARSTFRDTFLAL------PL--L
                 *                              *      *                 *

MHas2    W------MTYEAVI----TGFFPFFLIATVIQLFYRGKI--WNILLFLLTVQLVGLIKSSFASCLRGNIV
MHas1    W------MTYEAVV----SGLFPFFVAATVLRLFYAGRP--WALLWVLLCVQGVALAKAAFAAWLRGCVR
DG42     W------MTYESVV----SFIFPFFITATVIRLLIYAGTI--WNVVWLLLCIQIMSLFKSIYACWLRGNFI
HasA     WTIFEVVMFMMLIVAIGNLLFNQAIQLDLIKLFAFLSI----IFIVALC---R----NVHYMVKHPAS
NodC     RGLSPFLAFDAVGQNIGQLLLALSVVTGLAHLIMTATVPWWTILIIA--C---MTIIRCSVVALHARQLR
                                                                          **

MHas2    MVFMSLYSVLYMSSLLPAKMFAIATINKAGWTSGRKTIVVNF-IGLIPVSVWFTILLGGVIFTIYKES
MHas1    MVLLSLYAPLYMCGLLPAKFLALVTMNQSGWGTSGRKKLAANY-VPVLPLALWALLLGGLARSVAQEA
DG42     MLLMSLYSMLYMTGLLPSKYFALLTLNKTGWGTSGRKKIVGNY-MPILPLSIWAAVLCGGVGYSIYMDC
HasA     FLLSPLYGILHLFVLQPLKLYSLCTIKNTEWGTR-----------------------KKVTIFK*
NodC     FLGFVLHTPINLFLILPLKAYALCTLSNSDWLSR-----------------------GGKQTPIQT--
                                              ***     *              *

MHas2    KKPFSES-KQ---TVLIVGTLIYACYWVMLLTLYVVLINKCGRRKKGQQY------DMVLDV*
MHas1    RADWSGPSRAAEAYHLAAGAGAYAVAYWVVMLTIYWVGVRRLCRRRSGGYRVQV*
DG42     QNDWSTPEKQKEMYHLLYGCVGYVMYWVIMAVMYWVWVWKRCCR-KRSQTVTLVHDIPDM--CV*
HasA     
NodC     ----SGRVTPDCTCSGE*
                      *     *   *
```

Fig. 4-2

MHas2  190  KREVMY--TAFRALGRSVD--YVQVCDSDTMLDPASSVEMVKVLEED  232
MHas1  220  KREVMY--TAFKALGDSVD--YVQVCDSDTRLDPMALLELVRVLDED  262
DG42   207  KREVMY--TAFQAIGTSVD--YVQVCDSDTKLDELATVEMVKVLESN  249
HasA   138  KRHAQA--WAFERSDADV---FLTV-DSDTYIYPNALELLKSFNDE   178
NodC   120  KRKAQI--AAIGQSSGDL---VLNV-DSDSTIAFDVVSKLASKMRDP  160
Chs2   415  KKKINSHRWLFNAFCPVLQPTVVTLVDVGTRLNNTAIYRLWKVFDMD  461

MHas2  270  QCSFGDDRHLTN-RVLS--LGYATKYTARSKCLTETPIEYLRWLNQQTRWSKSYFREW  362
MHas1  338  HCTFGDDRHLTN-RMLS--MGYATKYTSRSRCYSETPSSFLRWLSQQTRWSKSYFREW  392
DG42   337  YCTLGDDRHLTN-RVLS--MGYRTKYTHKSRAFSETPSLYLRWLNQQTRWTKSYFREW  390
HasA   253  PVSIGDDRCLTN-YAID--LG-RTVYQSTARCDTDVFQLKSYLKQQNRWNKSFFRES  306
NodC   236  PSDFGEDRHLTI-LMLK--AGFRTEYVPDAIVATVVPDTLKPYLRQQLRWARSTFRDT  288
Chs2   557  NMYLAEDRILCWELVAKRDAKWVLKYVKEATGETDVPEDVSEFISQRRRWLNCAMFAA  613

Fig.5

```
  1 GTCTTATTTT GGGTGTGTTC AGTGCATTAG TGGACCTCTG GGAATGTACA
 51 GAAACTCCTT GTTGCATGAG TTTGTGGAAG ATTGGTACAA TCAAGAATTT
101 ATGGGCAACC AATGTAGCTT TGGTGATGAC AGGCATCTCA CGAACCGGGT
151 GCTGAGCCTG GGCTATGCAA CAAAATACAC AGCTCGATCT AAGTGCCTTA
201 CTGAAACACC TATAGAATAT CTCAGATGGC TAAAC
```

Fig.10A

```
HHAS2    1 ..........................SYFGCVQCISGPLGMYRNSLLHEFVEDWY  29
           |||||||||||||||||||||||||||||
MHas2  251 WISFLSSVRYWMAFNIERACQSYFGCVQCISGPLGMYRNSLLHEFVEDWY 300

30 NQEFMGNQCSFGDDRHLTNRVLSLGYATKYTARSKCLTETPIEYLRWLN.  78
            |||||||||||||||||||||||||||||||||||||||||||||||||
        301 NQEFMGNQCSFGDDRHLTNRVLSLGYATKYTARSKCLTETPIEYLRWLNQ 350
```

Fig.10C

```
HHAS2     1 ..........................GTCTTATTTTGGGTGTGTTCAGTGCATTAGT  31
                                       |||||||||||||||||||||||||||||||
Mhas2  1301 atatagaaagggcctgccagtcttattttggctgtgtccagtgcataagc          1350

32 GGACCCTCTGGGAATGTACAGAAACTCCTTGTTGCATGAGTTTGTGGAAGA   81
              |||||||||||||||||||||||||||||||||||||||||||||||||||
         1351 ggtccctctgggaatgtacagaaactccttgctgcatgaatttgtggaaga  1400

82 TTGGTACAATCAAGAATTTATGGGCAACCAATGTAGCTTTGGTGATGACA   131
              ||||||||||||||||| |||||||||||||||||||||||||||||||
         1401 ctggtacaatcaggaattcatgggtaaccaatgcagttttggtgacgaca   1450

132 GGCATCTCACGAACCGGGTGCTGAGCCTATGCAACAAAATACACA        181
              ||||||||||||||||||||||||||||||||||||||||||||
         1451 ggcacccttaccaacagggtgttgagtctgggctatgcaactaaatacacg  1500

182 GCTCGATCTAAGTGCCTTACTGAAACACCTATAGAATATCTCAGATGGCT   231
              |||||||||||||||||||||||||||||||||||||||||||||||||
         1501 gctcggtccaagtgccttactgcctgaaactcccatagaatatctgagatggct 1550

232 AAAC.....................................            235
              ||||
         1551 gaaccagcagacccgatggagcaagtcctacttccgagagtggctgtaca  1600
```

Fig.10B

```
  1 GTCCTACTTT GGCTGTGTGC AGTGTATTAG TGGGCCCTTG GGCATGTACC
 51 GCAACAGCCT CCTCCAGCAG TTCCTGGAGG ACTGGTACCA TCAGAAGTTC
101 CTAGGCAGCA AGTGCAGCTT CGGGGATGAC CGGCACCCTCA CCAACCGAGT
151 CCTGAGCCTT GGCTACCGAA CTAAGTATAC CGCGCGCTCC AAGTGCCCTCA
201 CAGAGACCCC CACTAAGTAC CTCCGGTGGC TCAAC
```

Fig.11A

```
  1 GTCCTACTTT GGCTGTGTGC AATGTATTAG TGGGCCTTTG GCATGTACC
 51 GCAACAGCCT CCTTCAGCAG TTCCTGGAGG ATTGGTACCA TCAGAAGTTC
101 CTAGGCAGCA AGTGCAGCTT TGGCGATGAT CGGCACCTTA CCAACCGAGT
151 CCTGAGTCTT GGCTACCGGA CTAAGTATAC AGCACGCTCT AAGTGCCCTCA
201 CAGAGACCCC CACTAGGTAC CTTCGATGGC TCAAT
```

Fig.11B

```
MHas3    1 GTCCTACTTTGGCTGTGTGCAATGTATTAGTGGGCCTTTGGGCATGTACC   50
           ||||||||||||||||||||||| ||||||||||||| ||||||||||||
HHAS3    1 GTCCTACTTTGGCTGTGTGCAGTGTATTAGTGGGCCCTTGGGCATGTACC   50

51 GCAACAGCCTCCTTCAGCAGTTCCTGGAGGATTGGTACCATCAGAAGTTC  100
           |||||||||| ||||||||||||||||| |||||||||||||||||||||
        51 GCAACAGCCTCCTCCAGCAGTTCCTGGAGGACTGGTACCATCAGAAGTTC  100

101 CTAGGCAGCAAGTGCAGCTTTGGGGATGATCGGCACCTTACCAACCGAGT  150
           |||||||||||||||||||| ||||| ||||||||||| ||||||||||
       101 CTAGGCAGCAAGTGCAGCTTCGGGGACGATCGGCACCTCACCAACCGAGT  150

151 CCTGAGTCTTGGCTACCGGACTAAGTATACAGCACGCTCTAAGTGCCTCA  200
           ||||||||| ||||||||| ||||||||||| ||||||| ||||||||||
       151 CCTGAGCCTTGGCTACCGAACTAAGTATACCGCGCGCTCCAAGTGCCTCA  200

201 CAGAGACCCCCACTAGGTACCTTCGATGGCTCAAT  235
           ||||||||||| |||||| ||||| ||||||||||
       201 CAGAGACCCCCCACTAGATACCTCCGGTGGCTCAAC  235
```

Fig.11C

```
HHAS3    1 SYFGCVQCISGPLGMYRNSLLQQFLEDWYHQKFLGSKCSFGDDRHLTNRV  50
           ||||||||||||||||||||||||||||||||||||||||||||||||||
MHas3    1 SYFGCVQCISGPLGMYRNSLLQQFLEDWYHQKFLGSKCSFGDDRHLTNRV  50

51 LSLGYRTKYTARSKCLTETPTKYLRWLN  78
           ||||||||||||||||||||| ||||||
        51 LSLGYRTKYTARSKCLTETPTRYLRWLN  78
```

Fig.11D

```
MHas3  276  SYFGCVQCISGPLGMYRNSLLQQFLEDWYHQKFLGSKCSFGDDRHLTNRVLSLGY
HHAS3       ------------------------------------------------------

MHas3  331  RTKYTARSKCLTETPTRYLRWLNQQTRWSKSYFREWLYNSLWFHKHHLWMTYESV
HHAS3       ---------------------------K--------------------------

MHas3  386  VTGFFPFFLIATVIQLFYRGRIWNILFLLTVQLVGIIKATYACFLRGNAEMIFM
HHAS3       ------------------------------------------------------

MHas3  441  SLYSLLYMSSLLPAKIFAIATINKS
HHAS3       -------------------------
```

Fig.12A

```
  1  ATGCCGGTGCAGCTGACTACAGCCCTGCGTGTGGGCACCAGTCTGTTTGCCCTGGTAGTGCTG    22
       M  P  V  Q  L  T  T  A  L  R  V  G  T  S  L  F  A  L  V  V  L
 67  GGAGGCATCCTGGCGGCCTATGTGACAGGCTACCAGTTTATCCACACAGAAAAGCACTACCTGTCC   44
       G  G  I  L  A  A  Y  V  T  G  Y  Q  F  I  H  T  E  K  H  Y  L  S
133  TTTGCCTTCTACGGTGCCATCCTTGGTCTCTACATCTGCTCATCCAGAGCCTGTTTGCCTTTCCTGGAG   66
       F  A  F  Y  G  A  I  L  G  L  Y  I  C  S  P  E  P  V  C  L  F  L  E
199  CACCGTGCGAATGCGCAGGGCGCAGGAGGCAGGCCTCTCAAGCTGCACTGCTCCCAGAGAGTCGCGTTCAGTG   88
       H  R  R  M  R  A  G  R  P  L  K  L  H  C  S  Q  R  S  R  S  V
265  GCACTCTGCATTGCTGCTGCCAAGAGAGACCCGAATACCTGCGCAAGTGCCTTCGCTCAGTCAG   110
       A  L  C  I  A  A  Y  Q  E  D  P  E  Y  L  R  K  C  L  R  S  A  Q
331  CGCATTGCCTTTCCAAACCTCAAGGTGGTCATGGTGGTCATGGTGGTGACAAGCTGGCCGACTAC   132
       R  I  A  F  P  N  L  K  V  V  M  V  V  D  G  N  R  Q  E  D  T  Y
397  ATGTTGGACATCTTCCATGAGGTGCTGGGTGGCACTGAGCAAGCTGGCTTCTTCTTTGTGTGGCGTAGC   154
       M  L  D  I  F  H  E  V  L  G  G  T  E  Q  A  G  F  F  V  W  R  S
463  AATTTCCATGAGGCGGGTGAAGGAGAGACCACCTTCTCATGCATCATGCAGAAGTGGGGGGGCCAAGCTGTGAGGTCATG   176
       N  F  H  E  A  G  E  G  E  T  E  A  S  L  Q  K  W  G  G  Q  V  M
529  GCTGTGGTGTGGGCCAGCACCTTCAAGGCCCCTTGGCCAACAGAGAAGTGGGGGGGCCAAGCGTGAGGTCATG   198
       A  V  V  W  A  S  T  F  S  C  I  M  Q  K  W  G  G  Q  V  R
595  TACACTGCCTTCAAGGCCCTTCAAGGCCCTTGGACTACATCCAGTGACTACATCAGTGACTCTGACACTGTG
       Y  T  A  F  K  A  L  Q  A  L  G  L  H  P  V  T  L  T  L
```

```
MHas3   --MPVQLTTALR-VVGTSL-------------------FALVVLGGILAAYVTGYQFIHTEKHYLSFGLYGAIL
MHas2   -MHCERFLCVLR-IIGTTL-------------------FGVSLLLGITAAYIVGYQFIQTDNYYFSFGLYGAFL
MHas1   ---MRQDMPKPSEAARCCSGLARRALTII---------FALLILGLMTWAYAAGVPLASDRYGLLAFGLYGAFL
DG42    MKEKAAETMEIPEGIPKDLEPKHPTLWRIIYYSFGVLLATITAAYVAEFQVLKHEAILFSLGLYGLAM------
HasA    ------MPIFKKTLIVLSFIFLISILIYLNMYLFGTST----VGI-YGVILITYLVIKL-------GLSF
                    *                             *      *                 *

MHas3   GLHLLIQSLFAFLEHRRM-----RRA-GRPLKLHCSQRSRSVALCIAAYQEDPEYLRKCLRSAQRIAFPN
MHas2   ASHLIIQSLFAFLEHRKM-----KKSLETPIKLN-------KTVALCIAAYQEDPDYLRKCLQSVKRLTYPG
MHas1   SAHLVAQSLFAYLEHRRVAAAAARRSLAKGPLDAATA--RSVALTISAYQEDPAYLRQCLTSARALLYPH
DG42    LLHLMMQSLFAFLEIRRV----NKSEL-PCSFK------KTVALTIAGYQENPEYLIKCLESCKYVKYPK
HasA    LYEPFKGNPHDY-----------------------------K-VAAVIPSYNEDAESLLETLKSVLAQTYPL
               *                                          *

MHas3   LK--VVMVVDGNRQEDTYMLDIFHEVLGGTEQAGFFVWRSNFHE-AGEGET------EASLQEGMERV
MHas2   IK--VVMVIDGNSDDDLYMMDIFSEVMGRDK-SATYIWKNNFHE-KGPGET------EESHKESSQHV
MHas1   TRLRVLMVVDGNRAEDLYMVDMFREVFADED-PATYVWDGNYHQPWEPAEATGAVGEGAYREVEAEDPG
DG42    DKLKIILVIDGNTEDDATMMEMFKDVFHGED-VGTYVWKGNYHTVKKPEETNKGSCPEVSKPLN-EDEG
HasA    S--EIYIVDDGSSNTDAIQL-----------IEEYVNRE----------------VDICRNVIVHR
                                          **                    *

MHas3   RA----VVWASTFSCIMQKWGGKREVMYTAFKALGNSVDYIQVCDSDTVLDPACTIEMLRVLEEDPQVG
MHas2   TQ----LVLSNKSICIMQKWGGKREVMYTAFRALGRSVDYVQVCDSDTMLDPASSVEMVKVLEEDPMVG
MHas1   RLAVEALVRTRRCVCVAQRWGGKREVMYTAFKALGDSVDYVQVCDSDTRLDPMALLELVRVLEDPRVG
DG42    INMVEELVRNKRCVCIMQQWGGKREVMYTAFQAIGTSVDYVQVCDSDTKLDELATVEMVKVLESNDMYG
HasA    S-----LVNK---------G-KRHAQAWAFERSDADV-FLTV-DSDTYIYPNALEELLKSFNDETVYA
                                                               ***
```

Fig.14A-1

```
MHas3                 GVGGDVQILNKYDSWISFLSSVRYWMAFNVERACQSYFGCVQCISGPLGMYRNSLLQQFLEDWYHQKFL
MHas2                 GVGGDVQILNKYDSWISFLSSVRYWMAFNVERACQSYFGCVQCISGPLGMYRNSLLHEFVEDWYNQEFM
MHas1                 AVGGDVRILNPLDSWVSFLSSLRYWMAFNVERACQSYFHCVSCISGPLGLYRNNLLQQFLEAWYNQKFL
DG42                  AVGGDVRILNPYDSFISFMSSLRYWMAFNVERACQSYFDCVSCISGPLGMYRNILQVFLEAWYRQKFL
HasA                  ATG-HLNARNRQTNLLTRITDIRYDNAFGVERAAQSLTGNILVCSGPLSIYRREVIIPNLERYKNQTFL
                        *      *  **   *   *  * ***        *  * *** **  **           *  *

MHas3                 GSKCSFGDDRHLTNRVLSLGYRTKYTARSKCLTETPTRYLRWLNQQTRWSKSYFREWLYNSLWFHKHHL
MHas2                 GNQCSFGDDRHLTNRVLSLGYATKYTARSKCLTETPIEYLRWLNQQTRWSKSYFREWLYNAMFHKHHL
MHas1                 GTHCTFGDDRHLTNRMLSMGYATKYTSRSRCYSETPSSFLRWLSQQTRWSKSYFREWLYNALWWHRHHA
DG42                  GTYCTLGDDRHLTNRVLSMGYRTKYTHKSRAFSETPSLYLRWLNQQTRWTKSYFREWLYNAQWWHKHHI
HasA                  GLPVSIGDDRCLTNYAIDLG-RTVYQSTARCDTDVPFQLKSYLKQQNRWNKSFFRESIISVKKILSNPI
                       *   **** **      *   *      * ** *    **  * **  **  *  *

MHas3                 ---W-----TGFFPFFLIATVIQLFYRGRI--WNILLFLLTVQLVGIIKATYACFLRG
MHas2                 ---W-----TGFFPFFLIATVIQLFYRGKI--WNILFLLTVQLVGLIKSSFASCLRG
MHas1                 ---W-----SGLFPFFVAATVLRLFYAGRP--WALLWVLLCVQGVALAKAAFAAWLRG
DG42                  ---W-----SFIFPFFITATVIRLIYAGTI--MNVVWLLLCIQIMSLFKSIYACWLRG
HasA                  VALWTIFEVVMFMMLIVAIGNLLFNQAIQLDLIKLFAFLSI----IFIVALC------R--NVHYMVKH
                        *        *   *  *    *                *                 *

MHas3                 NAEMIFMSLYSLLYMSSLLPAKIFAIATINKSGWGTSGPKTIVVNFIGLIPVSIWVAVLLGGLAYTAY-
MHas2                 NIVMVFMSLYSVLYMSSLLPAKMFAIATINKAGWGTSGRKTIVVNFIGLIPVSVWFTILLGGVIFTIYK
MHas1                 CVRMVLLSLYAPLYMCGLLPAKFLALVTMNQSGWGTSGRKKLAANYVPVLPLALWALLLGGLARSVAQ
DG42                  NFIMLLMSLYSMLYMTGLLPSKYFALLTLNKTGWGTSGRKKIVGNYMPILPLSIWAAVLCGVGYSIYM
HasA                  PASFLLSPLYGILHLFVLQPLKLYSLCTIKNTEWGTRKKVTIFK!
                         *     *   *  *  **    * *          *

MHas3                 -CQDLFSET----ELAFLVSGAILYGCYWVALLMLYLAITARRCG--KKPEQYSLAFAEV!
MHas2                 ESKKPFSES-KQ---TVLIVGTLIYACYWVMLLTLYVVLI-NKCGRRKKGQQYDMV-LDV!
MHas1                 EARADWSGPSRAAEAYHLAAGAGAYAYWVMLTIYWGVRRLC-RRRSGG-YRVQV!
DG42                  DCQNDWSTPEKQKEMYHLLYGCVGYVMYMVIMAVMYWVWVKRCC-RKRSQTVTLVHDIPDMCV!
                          *                                  *
```

Fig.14A-2

```
MHas3  194  KREVMY--TAFKALGNSVD--YIQVCDSDTVLDPACTIEMLRVLEED  236
MHas2  190  KREVMY--TAFRALGRSVD--YVQVCDSDTMLDPASSVEMVKVLEED  232
MHas1  220  KREVMY--TAFKALGDSVD--YVQVCDSDTRLDPMALLELVRVLDED  262
DG42   207  KREVMY--TAFQAIGTSVD--YVQVCDSDTKLDELATVEMVKVLESN  249
HasA   138  KRHAQA--WAFERSDADV---FLTV-DSDTYIYPNALEELLKSFNDE  178
NodC   120  KRKAQI--AAIGQSSGDL---VLNV-DSDSTIAFDVVSKLASKMRDP  160
celA1  435  KAGAENALVRVSAVLTNAP--FILNLDCDHYVNNSKAVREAMCFLMD  479
Chs2   415  KKKINSHRWLFNAFCPVLQPTVVTLVDVGTRLNNTAIYRLWKVFDMD  461

MHas3  312  KCSFGDDRHLTN-RVLS--LGYRTKYTARSKCLTETPTRYLRWLNQQTRWSKSYFREW  366
MHas2  308  QCSFGDDRHLTN-RVLS--LGYATKYTARSKCLTETPIEYLRWLNQQTRWSKSYFREW  362
MHas1  338  HCTFGDDRHLTN-RMLS--MGYATKYTSRSRCYSETPSSFLRWLSQQTRWSKSYFREW  392
DG42   337  YCTLGDDRHLTN-RVLS--MGYRTKYTHKSRAFSETPSLYLRWLNQQTRWTKSYFREW  390
HasA   253  PVSIGDDRCLTN-YAID--LG-RTVYQSTARCDTDVPFQLKSYLKQQNRWNKSFFRES  306
NodC   236  PSDFGEDRHLTI-LMLK--AGFRTEYVPDAIVATVVPDTLKPYLRQQLRWARSTFRDT  288
celA1  666  YGSVTED-ILTGFKMHCRGWRSIYCMPLRPAFKGSAPINLSDRLHQVLRWALGSVEIF  722
Chs2   557  NMYLAEDRILCWELVAKRDAKWVLKYVKEATGETDVPEDVSEFISQRRRWLNCAMFAA  613
```

Fig.14B

GENE ENCODING HYALURONAN SYNTHASE

RELATED APPLICATIONS

This application is a continuation in part of U.S. application Ser. No. 08/675,499, filed Jul. 3, 1996, now U.S. Pat. No. 6,492,150, the disclosure of which is incorporated by reference herein.

STATEMENT OF GOVERNMENT RIGHTS

This invention was made with the support of the U.S. Government via a grant from the National Institutes of Health (NRSA #1F32HL09311-01). The Government may have certain rights in the invention.

BACKGROUND OF THE INVENTION

Hyaluronan (HA, hyaluronic acid) is a linear unbranched polymer made up of repeating disaccharide units of D-glucuronic acid (β1→3) N-acetylglucosamine (β1→4). HA biosynthesis requires two enzyme activities; the transfer of UDP-N-acetylglucosamine (UDP-GlcNAc) and UDP-glucuronic acid (UDP-GlcUA), respectively, to the growing HA chain. HA is synthesized at the inner face of the plasma membrane and is subsequently extruded to the outside of the cell. HA is a major constituent of the extracellular matrix during embryonic development. For example, within the developing embryo, HA accumulates at sites of cell migration and proliferation, and has been proposed to play important roles in craniofacial, limb, neural tube, and heart development. In particular, HA is essential for the formation of endocardial cushions, the structures required for septation and the development of heart valves. In adults, HA is a major constituent of the extracellular matrix of most tissues and organs, and a critical component of the vitreous humor of the eye, joint fluid and cartilage.

HA is highly biocompatible and completely biodegradable, and has demonstrated beneficial effects when administered to the joints of arthritic race horses and to perforated rat tympanic membranes. HA has also been employed to protect eye tissue during artificial intraocular lens implantations, as a delivery agent for drugs and to prevent post-operative scarring.

Genes which encode HA biosynthetic enzymes have been identified in bacteria, e.g., Group A Streptococcus (Wessels et al., *Infect. Immun.*, 62, 433 (1994); DeAngelis et al., *J. Biol. Chem.*, 268, 19181 (1993); DeAngelis et al., *Biochemistry*, 33, 9033 (1994)). Polymerization of HA by *S. pyogenes* occurs through the action of a single enzyme, HA synthase, encoded by the hasA gene. The *S. pyogenes* HA synthase is localized to the membrane and is predicted to have several transmembrane domains and a large intracellular loop encompassing the active site of the enzyme. Purified immobilized HasA has been shown to be sufficient for HA polymerization in vitro (DeAngelis et al., *Biochemistry*, 33, 9033 (1994)). The transfer of the hasA gene and a second gene, hasB, into heterologous bacterial species results in the synthesis of an HA capsule (DeAngelis et al., *J. Biol., Chem.*, 268, 19181 (1993)). The hasB gene encodes a UDP-glucose dehydrogenase, which converts UDP-glucose to UDP-glucuronic acid (UDP-GlcUA), a subunit of HA.

However, there is evidence that other genes are also involved in bacterial HA biosynthesis. A protein originally identified in *Streptococcus equisimilis* as HA synthase (Lansing et al., *Biochem. J.*, 289, 179 (1993)) has no sequence similarity to *S. pyogenes* HasA but has significant sequence similarity to bacterial proteins involved in oligopeptide binding and transport. Although the total amount of HA synthesized by bacterial cells overexpressing the *S. equisimilis* HA synthase increased, the length of the resultant HA chains was significantly shorter, suggesting that the increase may be a function of an elevation in the rate of HA transport from the cell (O'Regan et al., *Int. J. Biol. Macromol.*, 16, 283 (1994)). Thus, rather than being directly involved in HA biosynthesis, the *S. equisimilis* HA synthase may be involved in the transport of HA, or may participate in HA synthesis as an accessory molecule, rather than as the synthase itself.

While both bacterial and animal sources of HA exist, high molecular weight HA is difficult and costly to isolate and purify due to the fact that HA is complexed with proteoglycans. Moreover, both bacterial and animal sources of HA are increasingly under more stringent regulatory controls due to fear of contamination with identifiable, or as yet unidentified, infectious or toxic agents. Furthermore, the extensive purification process of HA polymer from cells results in an HA polymer of considerable molecular weight polydispersity Thus, there is a need to isolate and purify genes that encode eukaryotic HA biosynthetic enzymes or proteins associated with the extracellular accumulation of HA.

SUMMARY OF THE INVENTION

The present invention provides an isolated and purified DNA molecule comprising a preselected DNA segment encoding eukaryotic, preferably mammalian, hyaluronan synthase-2 (Has2), or which encodes a biologically active subunit thereof. A preferred embodiment of the invention is a DNA molecule comprising a preselected DNA segment, e.g., SEQ ID NO:1, that encodes murine hyaluronan synthase-2. A murine hyaluronan synthase-2 having SEQ ID NO:2 has 21% identity and 28% similarity to Streptococcal HasA, and 55% identity and 73% similarity to murine Has1 (Itano et al., *J. Biol. Chem.*, 271, 9875 (1996)). Because the deduced amino acid sequence of Has1 is distinct from the murine hyaluronan synthase-2 having SEQ ID NO:2, there appears to be more than one mammalian gene encoding an enzyme or protein which is associated with HA biosynthesis and/or extracellular HA accumulation. Another preferred embodiment of the invention is a DNA molecule comprising a preselected DNA segment, e.g., SEQ ID NO:23, that encodes human hyaluronan synthase-2. Also provided is an isolated and purified DNA molecule comprising a preselected DNA segment which encodes a protein that increases the amount of extracellular hyaluronan produced by cultured primate cells transformed so as to express said DNA segment.

Further provided is an isolated and purified DNA molecule comprising a DNA segment encoding eukaryotic, preferably mammalian, hyaluronan synthase-3 (Has3), or a biologically active subunit thereof. A preferred embodiment of the invention includes a preselected DNA segment comprising SEQ ID NO:31 which encodes a murine hyaluronan synthase-3 comprising SEQ ID NO:32. Another preferred embodiment of the invention includes a DNA molecule comprising a preselected DNA segment comprising SEQ ID NO:25 which encodes a human hyaluronan synthase-3 comprising SEQ ID NO:29. The DNA molecules of the invention are double-stranded or single-stranded, preferably, they are cDNA.

An isolated and purified DNA molecule, such as a probe or a primer, of at least seven, preferably at least fifteen, nucleotide bases which hybridizes under stringent conditions to the DNA molecules of the invention, or RNA molecules derived from these DNA molecules, is also provided by the invention. The term "stringent conditions" is defined hereinbelow. The probes or primers of the invention have at least about 80%, preferably at least about 90%, identity to the above-disclosed DNA sequences. A preferred embodiment of the invention includes a probe or primer which has at least about 80%, preferably at least about 90%, identity to 1) SEQ ID NO:25, 2) SEQ ID NO:26 or 3) SEQ ID NO:31, or a sequence complementary thereto. The probes or primers of the invention are detectably labeled or have a binding site for a detectable label. Such probes or primers are useful to detect, quantify and/or amplify DNA strands with complementary to sequences related to hyaluronan synthase-2 or hyaluronan synthase-3 in eukaryotic tissue samples.

The present invention also provides an expression cassette comprising a promoter which is functional in a host cell operably linked to a preselected DNA segment encoding hyaluronan synthase-2. Preferably, the expression cassette comprises a preselected DNA segment encoding murine hyaluronan synthase-2. Another preferred embodiment of the invention is an expression cassette comprising a preselected DNA segment encoding human hyaluronan synthase-2.

The present invention further provides an expression cassette comprising a promoter which is functional in a host cell operably linked to a preselected DNA segment encoding hyaluronan synthase-3. Preferably, the expression cassette comprises a preselected DNA segment encoding murine hyaluronan synthase-3. Another preferred embodiment of the invention is an expression cassette comprising a preselected DNA segment encoding human hyaluronan synthase-3. Such expression cassettes can be placed into expression vectors which can then be employed to transform prokaryotic or eukaryotic host cells. The present vectors can also contain a functional DNA sequence which is a selectable marker gene or reporter gene, as described below.

Also provided is a transformed host cell, the genome of which has been augmented by a preselected DNA sequence encoding hyaluronan synthase-2, a preselected DNA sequence encoding hyaluronan synthase-3, or a combination thereof. Preferably, the preselected DNA sequence is integrated into the chromosome of the transformed host cell, and is heritable.

Expression of mouse hyaluronan synthase-2 or mouse hyaluronan synthase-3 in COS-1 cultured primate cells results in the formation of large well-pronounced HA coats, as described hereinbelow. Moreover, HA coat formation in COS cells transfected with an hyaluronan synthase-2 expression vector occurred in the absence of HA receptor expression, exogenously added HA, or proteoglycans. This suggests that hyaluronan synthase-2 expression leads to the synthesis of HA, in a form which is extruded through the plasma membrane and may associate with the cell surface to form an HA coat through continued attachment to the HA synthase.

Further provided is isolated, purified hyaluronan synthase-2 polypeptide. A preferred embodiment of the invention is isolated, purified murine hyaluronan synthase-2 polypeptide. A more preferred embodiment of the invention is isolated, purified murine hyaluronan synthase-2 polypeptide having SEQ ID NO:2.

Also provided is isolated, purified hyaluronan synthase-3 polypeptide. A preferred embodiment of the invention is isolated, purified murine hyaluronan synthase-3 polypeptide. A more preferred embodiment of the invention is isolated, purified murine hyaluronan synthase-3 polypeptide having SEQ ID NO:32.

As used herein, the term "Has2" or "hyaluronan synthase-2" is preferably defined to mean a polypeptide comprising SEQ ID NO:2, as well as variants of SEQ ID NO:2 which have at least about 80%, preferably at least about 90%, identity or homology to SEQ ID NO:2, or a biologically active subunit thereof. Biologically active subunits of hyaluronan synthase-2, variant hyaluronan synthase-2 polypeptides and biologically active subunits thereof, falling within the scope of the invention have at least about 50%, preferably at least about 80%, and more preferably at least about 90%, the activity of the hyaluronan synthase-2 polypeptide comprising SEQ ID NO:2. The activity of an hyaluronan synthase-2 polypeptide can be measured by methods well known to the art including, but not limited to, the particle exclusion assay described hereinbelow, an immunoassay which detects HA production, as described by Itano et al. (*J. Biol. Chem.*, 271, 9875 (1996)), HA synthase activity of crude membrane preparations, as described by Itano et al. (supra), or HA synthase activity of cell lysate preparations, as described by Meyer et al. (*Proc. Natl. Acad. Sci. USA*, 93, 4543 (1996)).

As used herein, the term "Has3" or "hyaluronan synthase-3" is preferably defined to mean a polypeptide comprising SEQ ID NO:32, SEQ ID NO:29, or a biologically active subunit thereof, as well as variants of SEQ ID NO:32 or SEQ ID NO:29 and subunits thereof which have at least about 80%, preferably at least about 90%, identity or homology to SEQ ID NO:32 or SEQ ID NO:29, respectively. Biologically active subunits of hyaluronan synthase-3, variant hyaluronan synthase-3 polypeptides and biologically active subunits thereof, falling within the scope of the invention have at least about 50%, preferably at least about 80%, and more preferably at least about 90%, the activity of the hyaluronan synthase-3 polypeptide comprising SEQ ID NO:32 or SEQ ID NO:29. The activity of an hyaluronan synthase-3 polypeptide can be measured by the methods described above for hyaluronan synthase-2.

The present invention also provides a method to produce hyaluronan synthase-2, comprising: culturing a host cell transformed with a nucleic acid molecule comprising a DNA segment encoding hyaluronan synthase-2 operably linked to a promoter, so that said host cell expresses said hyaluronan synthase-2. The method also preferably provides isolated recombinant hyaluronan synthase-2 polypeptide which is recovered from the transformed host cells.

Also provided is a method to produce hyaluronan synthase-3, comprising: culturing a host cell transformed with a nucleic acid molecule comprising a DNA segment encoding hyaluronan synthase-3 operably linked to a promoter, so that said host cell expresses said hyaluronan synthase-3. The method also preferably provides isolated recombinant hyaluronan synthase-3 polypeptide which is recovered from the transformed host cells. Optionally, host cells can be co-transformed with a nucleic acid molecule comprising a DNA segment encoding hyaluronan synthase-3 operably linked to a promoter and a nucleic acid molecule comprising a DNA segment encoding hyaluronan synthase-2 operably linked to a promoter.

Further provided is a method of altering the amount of hyaluronan produced by a cell. The method comprises introducing into a host cell a preselected DNA segment encoding hyaluronan synthase-2 operably linked to a promoter so as to yield a transformed host cell. The preselected DNA segment is expressed as hyaluronan synthase-2 in the transformed host cell in an amount that results in the transformed host cell producing an altered, preferably increased, amount of hyaluronan relative to the amount of hyaluronan produced by a corresponding untransformed host cell.

Also provided is a method of altering the amount of hyaluronan produced by a cell. The method comprises introducing into a host cell a preselected DNA segment encoding hyaluronan synthase-3 operably linked to a promoter so as to yield a transformed host cell. The preselected DNA segment is expressed as hyaluronan synthase-3 in the transformed host cell in an amount that results in the transformed host cell producing an altered, preferably increased, amount of hyaluronan relative to the amount of hyaluronan produced by a corresponding untransformed host cell.

Once isolated and purified, the genes involved in HA biosynthesis and extracellular accumulation of HA can be employed to synthesize HA in vitro. Because in vitro synthesized HA is of extremely high purity, is free from bacterial and animal cell contaminants, and can be optimized as to its physicochemical properties, it is a preferred source of HA relative to HA derived from bacterial or animal sources.

Moreover, the identification of genes involved in HA biosynthesis and/or coat formation may also be useful for defining the molecular basis for genetic diseases which are associated with a deficiency in HA biosynthesis, such as cartilage pathologies, for providing a clinically useful diagnostic test or in molecular-based therapeutics. Furthermore, the cloning of these genes will help to elucidate the molecular mechanism giving rise to the alteration of the protein encoded by the gene in patients having a particular disorder, e.g., a cartilage deficiency associated with reduced HA biosynthesis.

The probes and primers of the present invention are useful for detecting the expression of the DNA molecules of the present invention, detecting related DNA molecules and amplifying nucleic acid sequences that fall within the scope of the present invention.

The present invention also provides isolated and purified DNA molecules which provide "anti-sense" mRNA transcripts of the DNA sequences, including SEQ ID NO:1 or SEQ ID NO:31, which, when expressed from an expression cassette in a host cell, can alter HA expression.

BRIEF DESCRIPTION OF THE FIGURES

FIG. 3. Nucleotide sequence encoding, and corresponding amino acid sequence of, mouse Has2 (SEQ ID NO:1 and SEQ ID NO:2, respectively). The 5' and 3' untranslated nucleotide sequences are shown in lowercase, whereas the open reading frame is shown in uppercase. The stop codon, consensus polyadenylation signals, CA repeat and TA repeat are underlined.

FIG. 4. Alignment of mouse Has2 with mouse Has1 (Itano et al., *J. Biol. Chem.*, 271, 9875 (1996)) (SEQ ID NO:3), Xenopus laevis DG42 (SEQ ID NO:4), *Streptococcus pyogenes* HasA (SEQ ID NO:5), and *Rhizobium meliloti* NodC (SEQ ID NO:6). Identical residues are boxed. Dashes indicate gaps that have been introduced to maximize the identity. Asterisks below the line indicate positions at which there have been conservative amino acid substitutions.

FIG. 5. Alignment of two regions of mouse Has2 (SEQ ID NOS:7 and 8) with equivalent regions of mouse Has1 (Itano et al., supra) (SEQ ID NOS:9 and 40, respectively), X laevis DG42 (SEQ ID NOS:10 and 42, respectively), *S. pyogenes* HasA (SEQ ID NOS:11 and 44, respectively), *R. meliloti* NodC (SEQ ID NOS:12 and 46, respectively) and *S. cerevisiae* chitin synthase 2 (Chs2) (SEQ ID NOS:13 and 45, respectively). Dashes represent gaps that have been introduced to maximize homology. Residues highlighted in bold type are those that have been demonstrated to be critical in terms of enzyme activity of Chs2 (see Nagahashi et al., *J. Biol. Chem.*, 270, 13961 (1995)) and that are conserved in all six sequences.

FIG. 10. (A) Partial nucleotide sequence of human hyaluronan synthase-2 (SEQ ID NO:23). (B) Nucleotide sequence alignment of human hyaluronan synthase-2 (SEQ ID NO:23) and mouse hyaluronan synthase-2 (SEQ ID NO: 1). (C) Amino acid sequence alignment of human hyaluronan synthase-2 (SEQ ID NO:24) and mouse hyaluronan synthase-2 (SEQ ID NO:2).

FIG. 11. (A) Partial nucleotide sequence of human hyaluronan synthase-3 (SEQ ID NO:25). (B) Partial nucleotide sequence of murine hyaluronan synthase-3 (SEQ ID NO:26). (C) Nucleotide sequence alignment of human hyaluronan synthase-3 (SEQ ID NO:25) and mouse hyaluronan synthase-3 (SEQ ID NO:26). (D) Amino acid sequence alignment of human hyaluronan synthase-3 (SEQ ID NO:27) and mouse hyaluronan synthase-3 (SEQ ID NO:28).

FIG. 12. (A) Amino acid sequence alignment of a partial sequence for human hyaluronan synthase-3 (Has3) (SEQ ID NO:29) with the equivalent sequence of mouse Has3 (SEQ ID NO:30). Conserved amino acids are indicated by a dash (–). (B) Nucleotide (SEQ ID NO:31) and predicted amino acid (SEQ ID NO:32) sequence of the Has3 open reading frame. Sequences representing consensus HA binding motifs are underlined. The location of three introns within the gene are indicated by arrowheads. The first intron is located immediately preceding the start codon (ATG).

FIG. 14. (A) Amino acid sequence alignment of mouse Has3 (SEQ ID NO:32) with mouse Has2 (Mhas2) (SEQ ID NO:2), mouse Has1 (Mhas1) (SEQ ID NO:3), Xenopus laevis DG42 (DG42) (SEQ ID NO:4) and Streptococcus pyogenes HasA (SEQ ID NO:5). Conserved residues are boxed. Gaps have been introduced to maximize the alignment. Asterisks indicate positions at which there have been significant conservative amino acid substitutions. (B) Alignment of two regions of the mouse Has3 protein sequence (SEQ ID NO:35 and SEQ ID NO:36, respectively) with equivalent regions of related glycosyltransferases including mouse Has2 (SEQ ID NO:7 and SEQ ID NO:8, respectively), mouse Has1 (SEQ ID NO:9 and SEQ ID NO:40, respectively), Xenopus DG42 (SEQ ID NO:10 and SEQ ID NO:42, respectively), S. pyogenes HasA (SEQ ID NO:11 and SEQ ID NO:44, respectively), Rhizobium meliloti NodC (SEQ ID NO:42 and SEQ ID NO:46, respectively), Gossypium hirsutum putative cellulose synthase A1 (celA1) (SEQ ID NO:47 and SEQ ID NO:48, respectively) and Saccharomyces cerevisiae Chitin synthase 2 (Chs2) (SEQ ID NO:13 and SEQ ID NO:45, respectively). Site-directed mutagenesis of the residues highlighted in bold of yeast Chs2 resulted in loss of enzymatic activity (Nagahashi et al., J. Biol. Chem., 270, 13961 (1995)), suggesting that these residues may be critical for β1→4 glycosyltransferase activity. (C) Kyte-Doolittle hydrophilicity plots of mouse Has3, mouse Has2, mouse Has1 and S. pyogenes HasA. Hydrophobic areas are represented below the axes. Potential transmembrane domains are indicated by black bars drawn below each plot.

DETAILED DESCRIPTION OF THE INVENTION

Definitions

Figure 2:
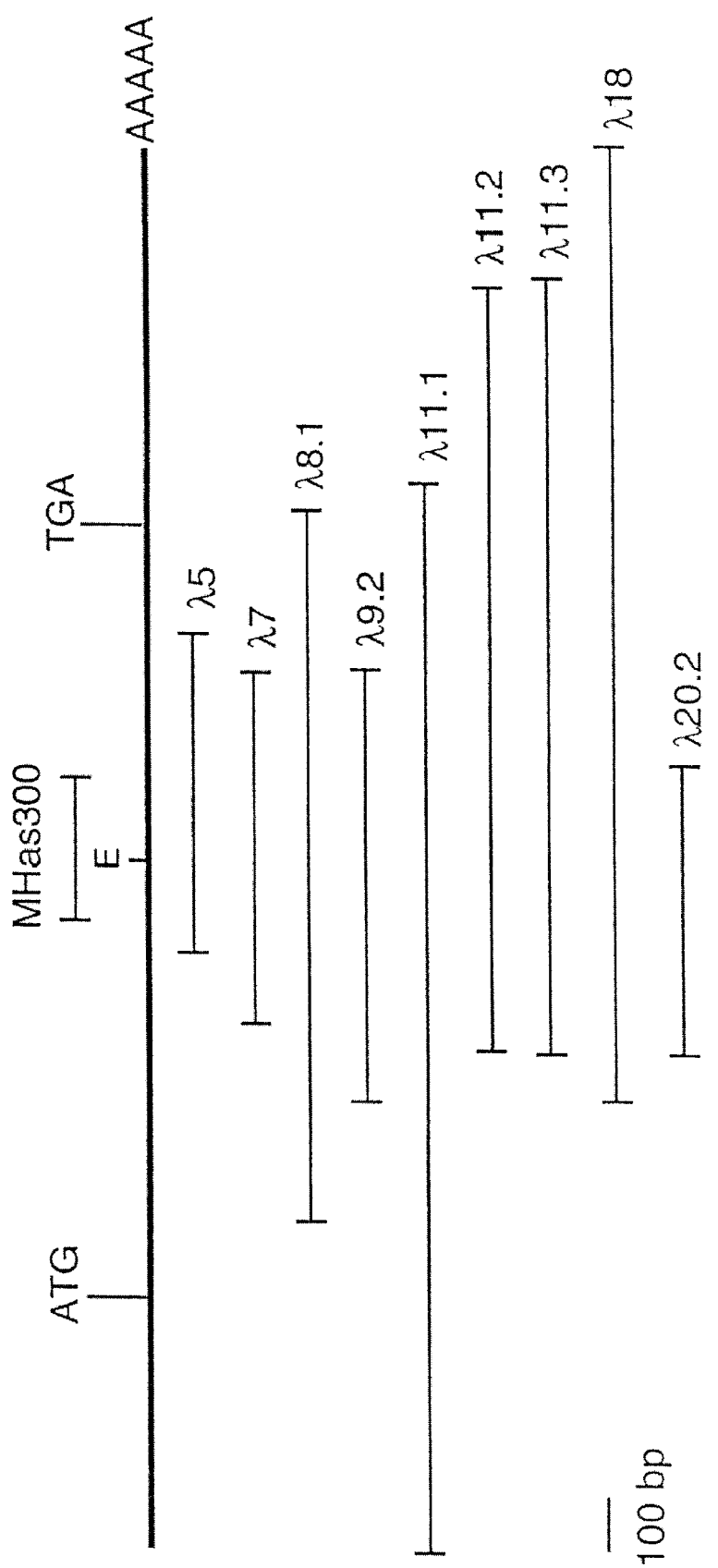
FIG. 2. cDNA library clones. The extent of overlapping cDNA clones is shown in relation to the mouse Has2 cDNA and to the degenerate RT-PCR mouse Has2 cDNA clone, MHas300. The positions of the translation initiation codon (ATG), the translation termination codon (TGA), and the internal EcoRI restriction endonuclease site (E) are indicated.

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., *Molecular Cloning: A Laboratory Manual*, Cold Spring Harbor (1989).

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989).

As used herein "stringent conditions" means conditions that detect a nucleic acid molecule with at least 80%, preferably at least 90%, nucleotide sequence homology to the probe or primer sequence. See Sambrook et al., *Molecular Cloning: A Laboratory Manual*, Cold Spring Harbor Laboratory Press (2nd ed., 1989) for selection of hybridization and washing conditions for DNA:DNA, as well as DNA:RNA (Northern blot), stable and specific duplex formation. Stringent conditions are those that (1) employ low ionic strength and high temperature for washing, for example, 0.015 M NaCl/0.0015 M sodium citrate (SSC);

0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS.

Sources of Nucleic Acids Encoding Has2 or Has3

A mouse gene has been recently identified that encodes a putative HA synthase, Has1 (Itano et al.,*J. Biol. Chem.*, 271, 9875 (1996)). However, the results of a complementation analysis conducted by Itano et al. during the isolation of the Has1 gene indicated that in the mouse, there are at least three genes that are involved in HA biosynthesis. Sources of nucleotide sequences from which these other genes, i.e., the present DNA molecules encoding Has2 or Has3, can be derived include total or polyA$^+$ RNA from eukaryotic, preferably mammalian, embryonic cells, or mesothelioma and Wilms' tumors or cell lines derived therefrom, as well as RNA isolated from embryonic tissue samples of cartilage, heart, neural tube and the like. Other sources of the DNA molecules of the invention include genomic DNA or cDNA libraries derived from any eukaryotic source including other mammals, e.g., rat, bovine, equine and the like, and other primates, e.g., humans and monkeys.

Isolation of a Gene Encoding Has2 or Has3

A nucleic acid molecule encoding mammalian HA biosynthetic enzymes, such as Has2 or Has3, can be identified and isolated using standard methods, as described by Sambrook et al., *Molecular Cloning: A Laboratory Manual*, Cold Spring Harbor, N.Y. (1989). For example, degenerate reverse-transcriptase PCR (RT-PCR) can be employed to isolate and clone Has2 or Has3 genes. This approach relies upon conserved sequences deduced from alignments of related gene or protein sequences. Sequence analysis of the hasA gene of *S. pyogenes* predicts that the HA synthase is a membrane protein with a large intracellular loop encoding the active site of the enzyme (DeAngelis et al., *J. Biol. Chem.*, 268, supra). Similarly, in mammalian cells, the HA synthase has been localized to the plasma membrane, with the active site on the inner face of the membrane (Philipson et al.,*J. Biol. Chem.*, 259, 5017 (1984); Prehm, *Biochem. J.*, 220, 597 (1984)). Moreover, database searches have identified the *Rhizobium sp.* nodulation factor C (NodC) proteins, the *Saccharomyces cerevisiae* chitin synthase 2 (Chs2) proteins, and the *Xenopus laevis* DG42 protein as sharing sequence identity with HasA (DeAngelis, et al., *Biochem. Biophys. Res. Commun.*, 199, 1 (1994)).

At least two degenerate primer pools for RT-PCR are prepared, one of which is predicted to anneal to the antisense strand, and one of which is predicted to anneal to the sense strand of a putative eukaryotic DNA molecule which encodes HA synthase. The oligonucleotides are made to correspond to highly conserved regions of the proteins which were compared to generate the primers.

One degenerate primer pool is then utilized for the first-strand synthesis. RNA is isolated, e.g., using TRI-ZOL™ reagent (GIBCO-BRL/Life Technologies, Gaithersburg, Md.). Reverse transcription reactions are performed on a source of nucleic acid believed to contain the DNA or RNA sequences of interest, e.g., total RNA isolated from mouse embryos.

Resultant first-strand cDNAs are then amplified in separate PCR reactions. The products of each PCR reaction are separated via an agarose gel and all consistently amplified products are gel-purified and cloned directly into a suitable vector, such as a plasmid vector. The resultant plasmids are subjected to restriction endonuclease and dideoxy sequencing of double-stranded plasmid DNAs.

Another approach to identify, isolate and clone genes which encode mammalian HA biosynthetic enzymes is to screen a cDNA library generated from embryonic heart or cartilage tissue. Screening for DNA fragments that encode all or a portion of the gene encoding Has2 or Has3 can be accomplished by probing the library with a probe, which has sequences that are highly conserved between genes believed to be related to Has2 or Has3, e.g., Has1, HasA, DG42 or NodC, or by screening of plaques for binding to antibodies that specifically recognize Has2 or Has3 related proteins. DNA fragments that bind to a probe having sequences which are related to Has2 or Has3, or which are immunoreactive with antibodies to Has2 or Has3 related proteins, can be subcloned into a suitable vector and sequenced and/or used as probes to identify other cDNA or genomic sequences encoding all or a portion of Has2 or Has3.

As used herein, the terms "isolated and/or purified" refer to in vitro isolation of a DNA or polypeptide molecule from its natural cellular environment, and from association with other components of the cell, such as nucleic acid or protein, so that it can be sequenced, replicated, and/or expressed. For example, "isolated Has2 nucleic acid" is RNA or DNA containing greater than 7, preferably 15, and more preferably 20 or more, sequential nucleotide bases that encode a biologically active Has2 polypeptide or a fragment thereof, or a biologically active variant Has2 polypeptide or a fragment thereof, that is complementary to the non-coding strand, or complementary to the coding strand, of the native Has2 polypeptide RNA or DNA, or hybridizes to said RNA or DNA and remains stably bound under stringent conditions.

"Isolated Has3 nucleic acid" is RNA or DNA containing greater than 7, preferably 15, and more preferably 20 or more, sequential nucleotide bases that encode a biologically active Has3 polypeptide or a fragment thereof, or a biologically active variant Has3 polypeptide or a fragment thereof, that is complementary to the non-coding strand, or complementary to the coding strand, of the native Has3 polypeptide RNA or DNA, or hybridizes to said RNA or DNA and remains stably bound under stringent conditions. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated Has2 nucleic acid is RNA or DNA that encodes a biologically active Has2 polypeptide sharing at least about 80%, preferably at least about 90%, sequence identity with the Has2 polypeptide of FIG. 3. An example of isolated Has3 nucleic acid is RNA or DNA that encodes a biologically active Has3 polypeptide sharing at least about 80%, preferably at least about 90%, sequence identity with the Has3 polypeptide of FIG. 12B.

As used herein, the term "recombinant nucleic acid" or "preselected nucleic acid," e.g., "recombinant DNA sequence or segment" or "preselected DNA sequence or segment" refers to a nucleic acid, i.e., to DNA that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

Variants of the DNA Molecules of the Invention

Nucleic acid molecules encoding amino acid sequence variants of Has2 or Has3 are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of a DNA molecule encoding an earlier prepared variant or a non-variant version of Has2 or Has3 polypeptide.

Oligonucleotide-mediated mutagenesis is a preferred method for preparing amino acid substitution variants of Has2 or Has3. This technique is well known in the art as described by Adelman et al., *DNA*, 2, 183 (1983). Briefly, Has2 or Has3 DNA is altered by hybridizing an oligonucleotide encoding the desired mutation to a DNA template, where the template is the single-stranded form of a plasmid or bacteriophage containing the unaltered or native DNA sequence of Has2 or Has3. After hybridization, a DNA polymerase is used to synthesize an entire second complementary strand of the template that will thus incorporate the oligonucleotide primer, and will code for the selected alteration in the Has2 or Has3 DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the Has2 or Has3, and the other strand (the original template) encodes the native, unaltered sequence of the Has2 or Has3, respectively. This heteroduplex molecule is then transformed into a suitable host cell, usually a prokaryote such as *E. Coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

A preferred embodiment of the invention is an isolated and purified DNA molecule comprising a preselected DNA segment encoding an Has2 polypeptide having SEQ ID NO:2, wherein the DNA segment comprises SEQ ID NO:1, or variants of SEQ ID NO:1 having nucleotide substitutions which are "silent." That is, when nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO:1 at the seventh codon (CTA in SEQ ID NO:1) includes the substitution of CTT, CTC or CTG for CTA. Other "silent" nucleotide substitutions in SEQ ID NO:1 which can encode a polypeptide having SEQ ID NO:2 can be ascertained by reference to page D1 in Appendix D in Sambrook et al., *Molecular Cloning: A Laboratory Manual* (1989). Nucleotide substitutions can be introduced into DNA segments by methods well known to the art. See, for example, Sambrook et al., supra.

Another preferred embodiment of the invention is an isolated and purified DNA molecule comprising a preselected DNA segment encoding an Has3 polypeptide having SEQ ID NO:32, wherein the DNA segment comprises SEQ ID NO:31, or variants of SEQ ID NO:31 having nucleotide substitutions which are "silent." That is, when nucleotide substitutions are present in a codon, the same amino acid is encoded by the codon with the nucleotide substitution as is encoded by the codon without the substitution. For example, leucine is encoded by the codon CTT, CTC, CTA and CTG. A variant of SEQ ID NO:31 at the fifth codon (CTG in SEQ ID NO:31) includes the substitution of CTT, CTC or CTA for CTG. Other "silent" nucleotide substitutions in SEQ ID NO:31 which can encode a polypeptide having SEQ ID NO:32 can be ascertained by reference to page D1 in Appendix D in Sambrook et al., *Molecular Cloning: A Laboratory Manual* (1989). Nucleotide substitutions can be introduced into DNA segments by methods well known to the art. See, for example, Sambrook et al., supra.

Chimeric Expression Cassettes

As used herein, "chimeric" means that a vector comprises DNA from at least two different species, or comprises DNA from the same species, which is linked or associated in a manner which does not occur in the "native" or wild type of the species.

The recombinant or preselected DNA sequence or segment, used for transformation herein, may be circular or linear, double-stranded or single-stranded. Generally, the preselected DNA sequence or segment is in the form of chimeric DNA, such as plasmid DNA, that can also contain coding regions flanked by control sequences which promote the expression of the preselected DNA present in the resultant cell line. Aside from preselected DNA sequences that serve as transcription units for Has2, Has3, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention. A preferred promoter useful in the practice of the invention is the CMV promoter.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Maal,* Cold Spring Harbor Laboratory Press (2d ed., 1989), provides suitable methods of construction.

Transformation into Host Cells

The recombinant DNA can be readily introduced into the host cells by transfection with an expression vector comprising DNA encoding Has2, or an expression vector comprising DNA encoding Has3, by any procedure useful for the introduction into a particular cell, e.g., calcium phosphate precipitation, lipofection, electroporation, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is resident in the genome of the host cell but is not expressed, or not highly expressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding Has2, or which comprises a gene encoding Has3, which host cell may or may not express significant levels of autologous or "native" hyaluronan.

Has2 or Has 3 Polypeptides

The present invention provides an isolated, purified Has2, or an isolated, purified Has3, which can be prepared by recombinant DNA methodologies. The general methods for isolating and purifying a recombinantly expressed protein from a host cell are well known to those in the art. Examples of the isolation and purification of such proteins are given in Sambrook et al., cited supra. Moreover, since the present invention provides the complete amino acid sequence of murine Has2 (FIG. 3), and murine Has3 (FIG. 12B), they or bioactive variants thereof can also be synthesized by the solid phase peptide synthetic method. This established and widely used method, including the experimental procedures, is described in the following references: Stewart et al., *Solid Phase Peptide Synthesis*, W.H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285.

When Has2 or Has3 polypeptide is expressed in a recombinant cell, preferably a Has2- or Has3-cell, respectively, it is necessary to purify Has2 or Has3 polypeptide from recombinant cell proteins or polypeptides to obtain preparations that are substantially homogenous as to Has2 or Has3 polypeptide. For example, the culture medium or lysate can be centrifuged to remove particulate cell debris. The membrane and soluble protein fractions are then separated. The Has3 polypeptide may then be purified from the soluble protein fraction and, if necessary, from the membrane fraction of the culture lysate. Has3 polypeptide can then be purified from contaminant soluble or membrane proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Has2 polypeptide, Has3 polypeptide, variant Has2 polypeptides, variant Has3 polypeptides, or biologically active subunits thereof can also be prepared by in vitro transcription and translation reactions. For example, a Has3 expression cassette can be employed to generate Has3 transcripts which are subsequently translated in vitro so as to result in a preparation of substantially homogenous Has3, variant Has3, or biologically active subunits thereof. The construction of vectors for use in vitro transcription/translation reactions, as well as the methodologies for such reactions, are well known to the art.

Once isolated from the resulting transgenic host cells or from in vitro transcription/translation reactions, derivatives and chemically derived variants of the Has2 polypeptide or Has 3 polypeptide can be readily prepared. For example, amides of the Has3 polypeptides of the present invention may also be prepared by techniques well known in the art for converting a carboxylic acid group or precursor, to an amide. A preferred method for amide formation at the C-terminal carboxyl group is to cleave the polypeptide from a solid support with an appropriate amine, or to cleave in the presence of an alcohol, yielding an ester, followed by aminolysis with the desired amine.

Salts of carboxyl groups of the Has2 polypeptide or Has3 polypeptide may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the present polypeptides may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired. In addition, the internal Has2 or Has3 amino acid sequence of FIG. 3 or FIG. 12B, respectively, can be modified by substituting one or two conservative amino acid substitutions for the positions specified, including substitutions which utilize the D rather than L form. The invention is also directed to variant or modified forms of the Has2 polypeptide or Has 3 polypeptide. One or more of the residues of the Has 2 polypeptide can be altered, so long as the variant polypeptide has at least about 50% of the biological activity of the protein having SEQ ID NO:2. One or more of the residues of the Has 3 polypeptide can be altered, so long as the variant polypeptide has at least about 50% of the biological activity of the protein having SEQ ID NO:32. Conservative amino acid substitutions are preferred--that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Acid addition salts of the polypeptides may be prepared by contacting the polypeptide with one or more equivalents of the desired inorganic or organic acid, such as, for example, hydrochloric acid. Esters of carboxyl groups of the polypeptides may also be prepared by any of the usual methods known in the art.

Has2 or Has 3 Variant Polypeptides

It is envisioned that variant Has2 polypeptides have at least one amino acid substitution relative to SEQ ID NO:2. It is also envisioned that variant Has3 polypeptides have at least one amino acid substitution relative to SEQ ID NO:32. In particular, amino acids are substituted in a relatively conservative manner. Such conservative substitutions are shown in Table 1 under the heading of exemplary substitutions. More preferred substitutions are under the heading of preferred substitutions. After the substitutions are introduced, the products are screened for biological activity.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Amino acid substitutions falling within the scope of the invention, are, in general, accomplished by selecting substitutions that do not differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

The invention also envisions Has2 or Has3 variants with non-conservative substitutions. Non-conservative substitutions entail exchanging a member of one of the classes described above for another. Amino acid substitutions are introduced into the DNA molecules of the invention by methods well known to the art. For example, see the description hereinabove for the introduction of silent mutations into the DNA molecules of the invention.

Uses of Has2 or Has3 Genes, and Polypeptides Thereof

The genes involved in HA biosynthesis and extracellular accumulation of HA ("HA coat formation"can be employed to synthesize HA in vitro. Because in vitro synthesized HA is of extremely high purity, is free from bacterial and animal cell contaminants, and can be optimized as to its physico-chemical properties, it is preferred to HA derived by extraction from bacterial or animal sources.

In vitro prepared HA has a similar range of applications as those described above for HA which is derived from animal or bacterial cells, e.g., protecting eye tissue during artificial intraocular lens implantation, as a drug delivery vehicle, and preventing or inhibiting post-operative adhesions. In vitro synthesized HA may also be employed to enhance or promote wound healing or tissue repair, e.g., to prevent restenosis following balloon angioplasty, and to repair or replace damaged or absent cartilage present in congenital defects, craniofacial disorders and arthritis. In addition, HA can be derivatized, as described in Balazs et al. (*Blood Coag. Fibrinolysis,* 2, 173 (1991)), to provide improved mechanical properties and an extended residence time in vivo.

Moreover, the identification of genes involved in HA biosynthesis and/or coat formation may also be useful for defining the molecular basis for genetic diseases, such as cartilage pathologies, e.g., rheumatoid arthritis, and for providing a clinically useful diagnostic test or in molecular-based therapeutics. Once such a gene has been identified, a probe specific for the gene can be made. Patient DNA can be screened with the probe to detect particular genetic variants that correlate with disease, e.g., craniofacial disorders. Patient RNA can be incubated with the probe to determine if the gene is over or under expressed in a patient with a particular disease relative to disease-free patients.

Furthermore, the cloning of genes involved in HA biosynthesis and/or extracellular coat formation will help to elucidate the molecular mechanism giving rise to the alteration of the protein encoded by the gene in patients having a particular disorder, e.g., cartilage deficiency. Once the molecular mechanism underlying the expression of the gene is understood, molecular genetic-based therapies directed to controlling the expression of the gene can then be employed to correct or supplement the expression of the gene in patients with the disorder.

In addition, high serum levels of HA are associated rheumatoid arthritis, septic conditions accompanying certain malignancies, e.g., mesothelioma and Wilms' tumor, and edema due to inflammation in the lung and in kidneys post-kidney transplantation. HA has also been implicated in Grave's ophthalmopathy, cirrhosis of the liver and accelerated aging in Werner's syndrome. Thus, the isolation of eukaryotic HA biosynthetic genes can be useful in gene therapies which employ the cloned genes in antisense expression vectors to inhibit or reduce the overexpression of HA genes in these patient populations. For example, an expression vector containing antisense Has3 can be introduced into joints (for rheumatoid arthritis), or into mesothelioma or Wilms' tumor cells, to inhibit or reduce the overexpression of Has3.

The probes and primers of the present invention are useful for detecting the expression of the DNA molecules of the present invention, detecting related DNA molecules and amplifying nucleic acid sequences that fall within the scope of the present invention. The uses of probes and primers, as well as their isolation, purification and conditions under which they are employed for the detection or amplification of a specific gene, are well known in the art.

Figure 12B-2:
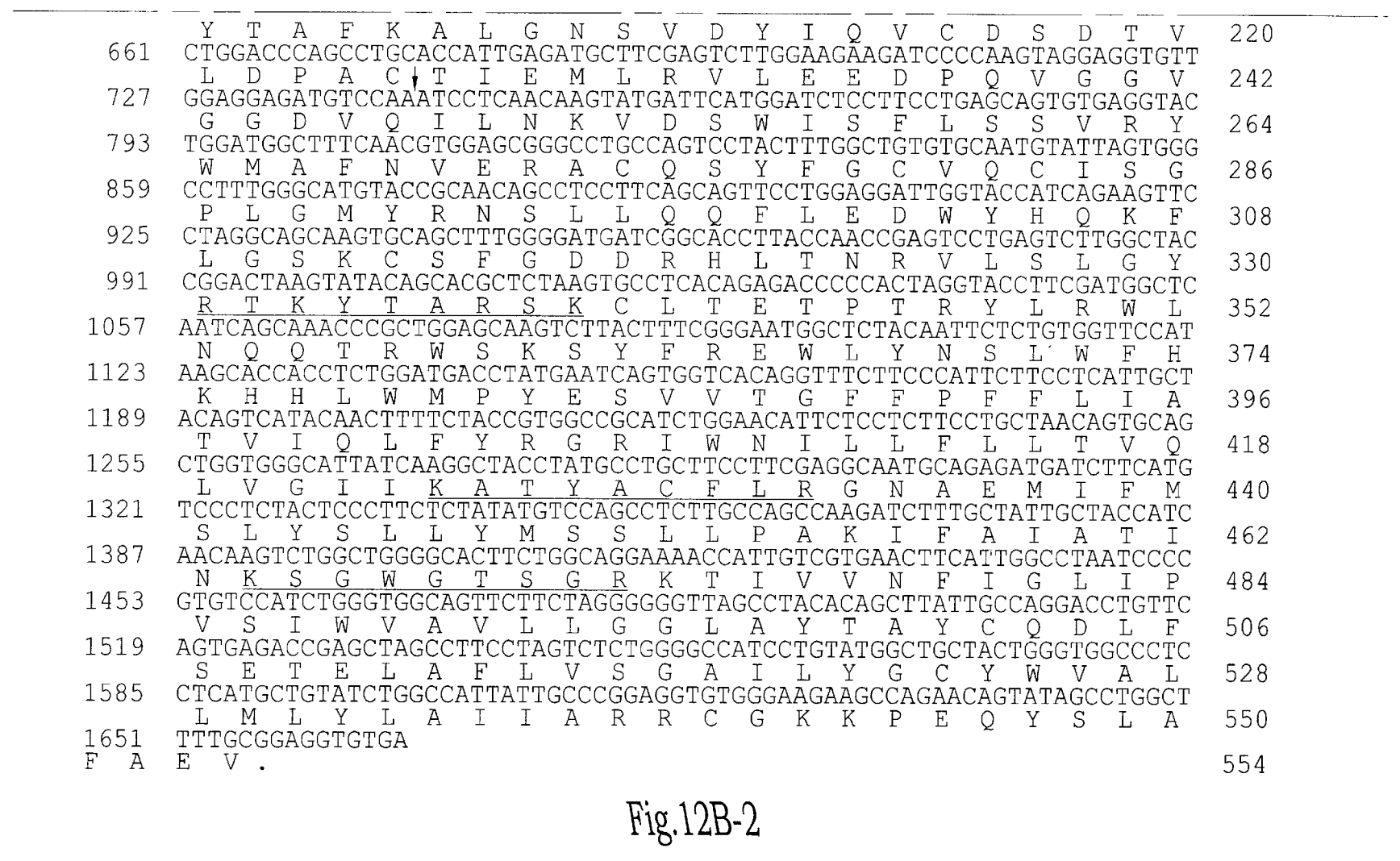

The present invention also provides isolated and purified DNA molecules which are "anti-sense" mRNA transcripts of the DNA sequences, including SEQ ID NO:1 or SEQ ID NO:31, shown in FIG. 3 or FIG. 12B, respectively, which, when expressed from an expression cassette in a host cell, can alter HA expression.

The invention will be further described by the following examples.

EXAMPLE 1 cDNA Cloning and Characterization of Mouse Hyaluronan Synthase-2

The aligned amino acid sequences of HasA, DG42 and NodC were utilized to prepare primers for a degenerate PCR strategy to identify a HasA/DG42 related cDNA in the mouse. Three degenerate primer pools for RT-PCR were prepared, two of which were predicted to anneal to the antisense strand, and one of which was predicted to anneal to the sense strand of a putative eukaryotic DNA molecule which encodes HA synthase. The oligonucleotides were made corresponding to the peptide sequences AFNVERACQ (SEQ ID NO:14), GDDRHLTN (SEQ ID NO:15), and QQTRWTKSYF (SEQ ID NO:16), and had the following degenerate nucleotide sequences: DEG 1 primer, 5'-GCN TTY AAY GTN GAR MGN GCN TGY CA 3' (SEQ ID NO:17, sense strand), DEG 3 primer, 5'-RTT NGT NAR RTG NCK RTC RTC NCC-3' (SEQ ID NO:18, antisense strand), and DEG 5 primer, 5'-RAA RTA NSW YTT NGT CCA NCK NGT YTG YTG-3' (SEQ ID NO:19, antisense strand).

A degenerate primer pool made to the peptide sequence QQTRWTKSYF (SEQ ID NO:16, DEG 5) was utilized for the first-strand synthesis. RNA was isolated using TRIZOL™ reagent (GIBCO-BRL/Life Technologies, Gaithersburg, Md.) according to the manufacturer's directions. Reverse transcription reactions were performed on total RNA isolated from 10.5 and 14.5 days post coitum (dpc) C57BL/6J mouse embryos. Briefly, 5 $\mu$g of total RNA were heat-denatured at 95° C. then split into two separate reactions. One reaction served as a control and amplified a fragment of 28S ribosomal RNA. The second reaction received one of two degenerate primer pools at a final concentration of 2 $\mu$M. Reverse-transcription was carried out at 42° C. using 10 units M-MuLV reverse transcriptase (Boehringer Mannheim, Indianapolis, Ind.) in a total volume of 25 $\mu$l.

Five microliters of each resultant first-strand cDNA were amplified in separate 100 $\mu$l PCR reactions using combinations of degenerate primer pools 1 and 3 (DEG 1/3) or 1 and 5 (DEG 1/5). Amplification conditions were as follows: 35 cycles of 94° C. for 1 minute, 50° C. for 1 minute, 72° C. for 1 minute, followed by a final extension of 72° C. for 10 minutes. Primer pools were used at a final concentration of 1 $\mu$M. Twenty microliters of each PCR reaction was separated through a 2.0% agarose gel (FIG. 1). All consistently amplified products (see arrows in FIG. 1) were gel-purified and cloned directly into a pBluescript KSII+ (Stratagene Cloning Systems, La Jolla, Calif.) T-vector prepared as described by Marchuk et al. (*Nucleic Acids Res.,* 19, 1154 (1991)). The resultant plasmids were subjected to restriction endonuclease and dideoxy sequencing of double-stranded plasmid DNAs using a Sequenase Version 2.0 sequencing kit (United States Biochemical Corp, Cleveland, Ohio).

The 300 bp DEG 1/5 product (MHas300) and the 180 bp DEG 1/3 product were related by a common internal site for the restriction endonuclease EcoRI, as shown below the gel image in FIG. 1. Sequence analysis of the other consistently amplified PCR products indicated that they were unrelated to mouse HAS (Itano et al., *J. Biol. Chem.,* 271, 9875 (1996)) hasA, DG42, nodC, and the 180 bp and 300 bp PCR products.

The 300 bp cDNA fragment, MHas300 was utilized as a probe to screen a primary λgt10 cDNA library constructed from 8.5 dpc C57BL/6J polyA+RNA (kindly provided by Dr. J. J. Lee, Mayo Clinic Scottsdale). The probe was labeled to high specific activity using random-priming in the presence of [$^{32}$P]dCTP (Feinberg et al., *Anal. Biochem.,* 132, 6 (1984)). Approximately $1.5\times10^6$ plaque-forming units (pfus) were screened using standard procedures (Sambrook et al., *Molecular Cloning: A Laboratory Manual,* Cold Spring Harbor (1989)). Double positive plaques were identified and taken through two additional rounds of plaque-purification. In addition, a portion of each primary plaque was screened by PCR, employing a combination of primers that flanked the λgt10 cloning site and MHas2 specific primers, to determine insert size relative to the MHas300 cDNA fragment. Fourteen positive clones were obtained and analyzed. The mouse λ cDNA library yielded multiple overlapping clones, which collectively spanned approximately 3 kb (FIG. 2). EcoRI restriction fragments were then subcloned into pBluescript KSII+ for sequence analysis. The nucleotide sequence of both strands was determined using synthetic oligonucleotide primers made to the mouse Has2 sequence and to the vector.

Sequence analyses identified an open reading frame (ORF) of 1656 bps, flanked by 5' and 3' untranslated regions (UTRs) of 507 and 772 bps, respectively (FIG. 3, SEQ ID NO:1). The open reading frame predicted a 63 kDa protein with several transmembrane sequences, multiple consensus phosphorylation sites, and four putative hyaluronan binding motifs. The predicted translation initiation site conformed to the Kozak consensus for initiation (Kozak, *Nucleic Acids Res.,* 12, 857 (1984)). Although there were four additional upstream ATGs within the 5' UTR, none of these fitted the Kozak consensus and all were followed closely by in-frame stop codons. The presence of several upstream ATGs has, however, been more commonly described in oncogenic sequences (Kozak, *Nucleic Acids Res.,* 15, 8125 (1987)). The 3' UTR contained two consensus sequences for polyadenylation, a CA repeat and a TA repeat (FIG. 3).

Database searches indicated that the predicted amino acid sequence of mouse Has2 (SEQ ID NO:2) aligned most significantly with Xenopus DG42 (SEQ ID NO:10; 56% identity, 70% similarity; Rosa et al., *Dev. Biol.,* 129, 114 (1987)), Streptococcal HasA (SEQ ID NO:11; 21% identity, 28% similarity; DeAngelis et al., *J. Biol. Chem.,* 268, 19181 (1993)), *Rhizobium sp.* NodC (SEQ ID NO:12; Jacobs et al., *J. Bacteriol.,* 162, 469 (1985); Collins-Emerson et al., *Nucleic Acids Res.,* 18, 6690 (1990)), and *Saccharomyces cerevisiae* chitin synthase 2 (Chs2) (SEQ ID NO:13; Bulawa, *Mol. Cell Biol.,* 12, 1764 (1992)) (FIG. 4). In addition, mouse Has2 displayed 55% identity and 73% similarity to the recently reported mouse Has1 gene (SEQ ID NO:11, Itano et al., *J. Biol. Chem.,* 271, 9875 (1996)), and the human homologue of this gene (Yang et al., *EMBO J.,* 13, 286 (1994)). Surprisingly, the deduced amino acid sequence of the cDNA of Itano et al. is distinct from the Has2 cDNA described hereinbelow, although the sequences are clearly related.

Recently isolated clones for a second human Has gene, which shares greater than 90% amino acid identity to mouse Has2 and thus is predicted to represent the human Has2 gene have also been obtained (SEQ ID NO:23). This suggests that there are at least two related Has genes in both mouse and humans.

Figures 1, 6A:
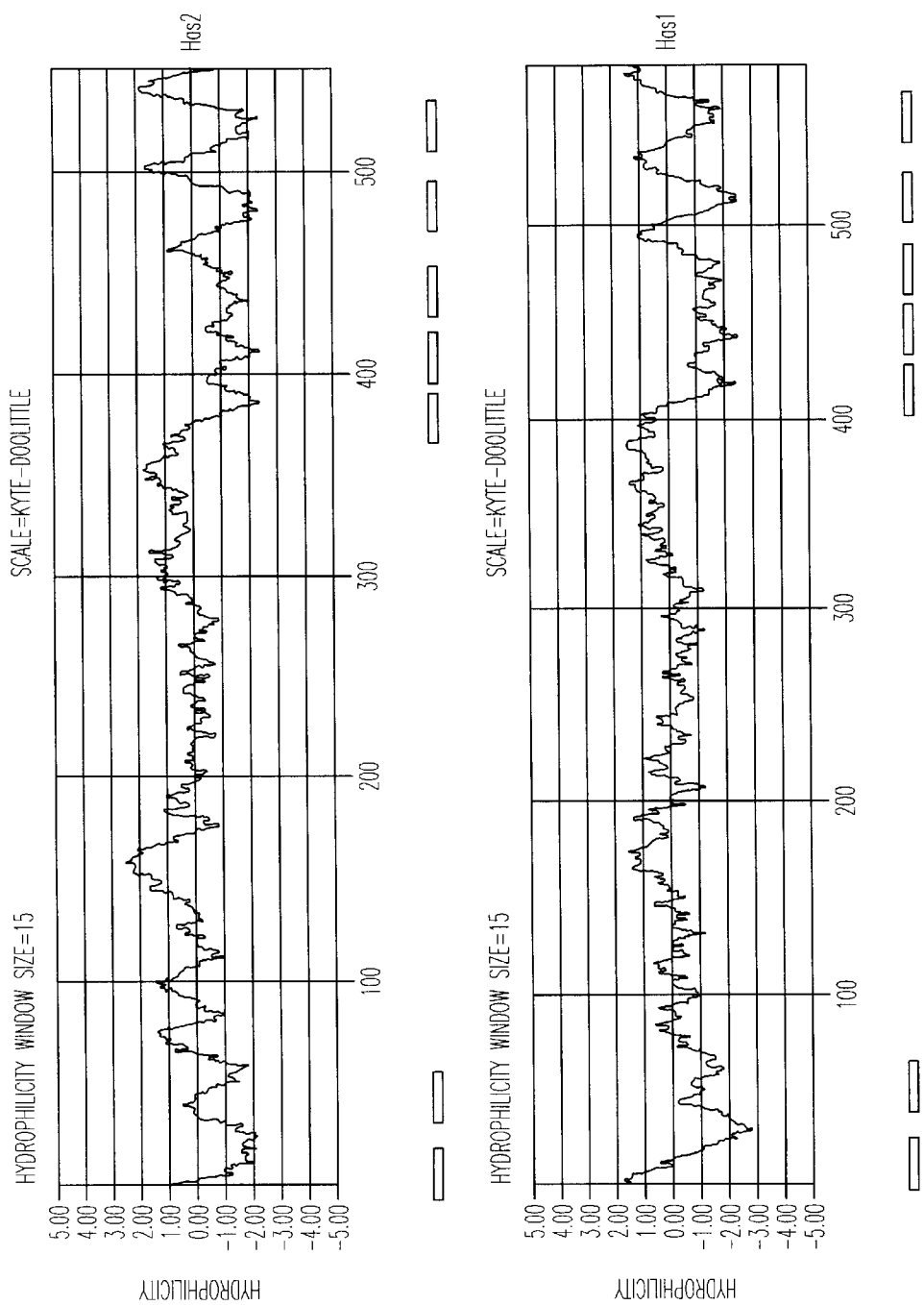
FIG. 1. Degenerate RT-PCR analysis. An agarose gel is shown which depicts polymerase chain reaction (PCR) amplified bands characteristic of a typical RT-PCR experiment. RT-PCR was performed on total RNA isolated from 10.5 days post coitum (dpc) (E 10.5) and 14.5 dpc (E 14.5) C57BL/6J mouse embryos. M, indicates 1 kilobase pair ladder (GIBCO-BRL/Life Technologies, Gaithersburg, Md.). DEG1/3 indicates degenerate primer pools 1 and 3. DEG 1/5 indicates degenerate primer pools 1 and 5.
Figures 2, 6A:
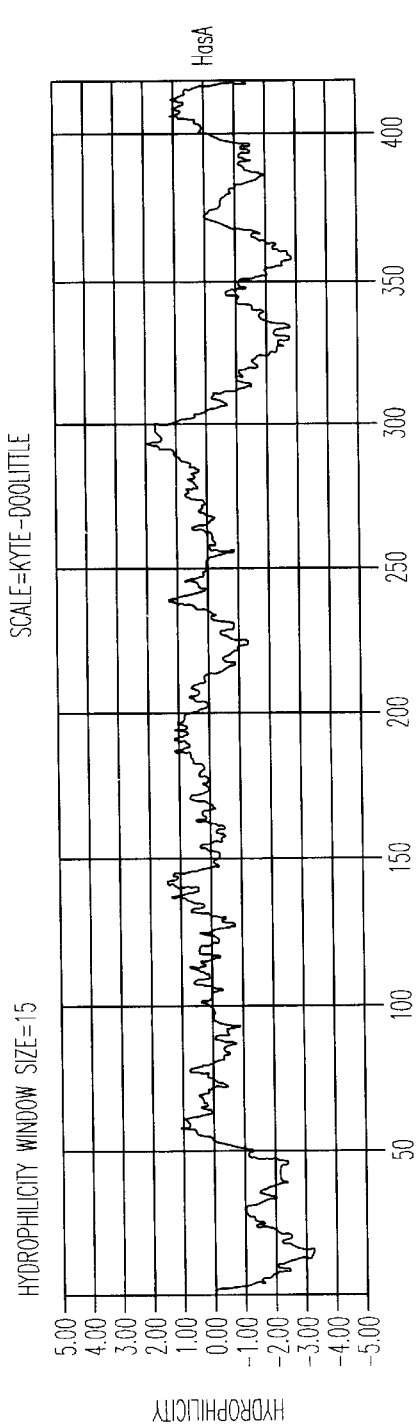
Figure 6B:
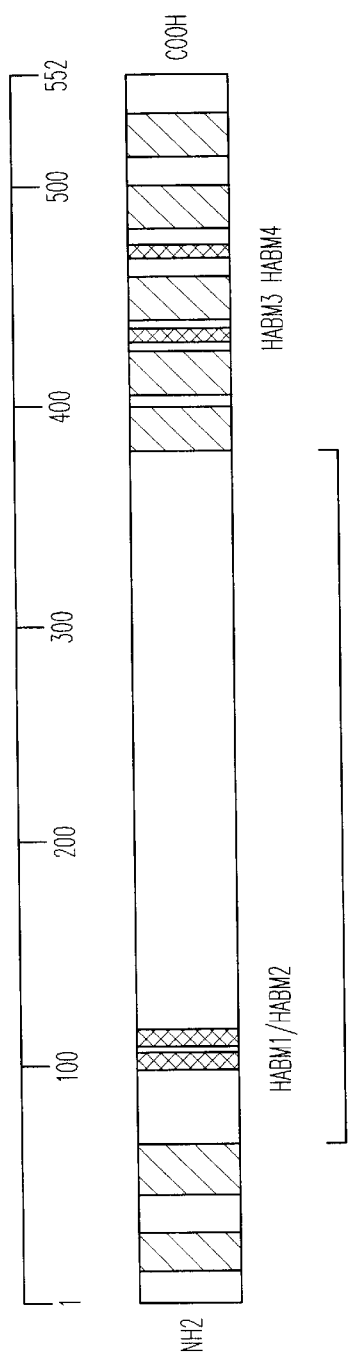
FIG. 6. Kyte-Doolittle hydrophilicity plots and linear cartoon representation of mouse Has2 protein. A) Comparison of mouse Has2, mouse Has1 and *Streptococcus pyogenes* HasA by Kyte-Doolittle hydrophilicity plots. The amino acid sequences of mouse Has2, mouse HAS (Has 1) and bacterial HasA were analyzed using the Kyte-Doolittle algorithm (MacVector) with a hydrophilicity window size of 15. Strongly hydrophobic areas of the proteins are indicated below the axes. Areas predicted to be potential transmembrane domains or signal peptide are indicated by the black bars below each plot. B) Linear representation of mouse Has2 predicted protein. Hydrophobic areas are indicated by the filled black boxes. Consensus $B(X_7)B$ HA binding motifs (HABM) are indicated by the filled gray boxes and are numbered. These motifs correspond to amino acid residues 100–108, 107–115, 420–428, and 460–468. The predicted intracellular loop of the molecule is indicated.

Investigation of the primary amino acid sequence of mouse Has2 identified several potential transmembrane sequences (FIG. 4), four potential HA binding motifs fitting the B(X$_7$)B consensus (Yang et al., *EMBO J.* 13, 286 (1994)), and numerous consensus sequences for phosphorylation by protein kinase C (PKC) and cyclic-AMP dependent kinases, such as protein kinase A (PKA) (Person et al., In: *Protein Phosphorylation: A Practical Approach* (Hardie, D. G., ed), IRL Press at Oxford University Press, Oxford (1993)). Has2 is predicted to be a multiple membrane-spanning protein with a large cytoplasmic loop, similar to the predicted structure of Streptococcus HasA and mouse HAS (Has1) (FIG. 6B). Sequence alignment of Has2 with *Saccharomyces cerevisiae* Chitin synthase2 (Chs2; SEQ ID NO:13 as shown in FIG. 5) demonstrated that the residues recently shown to be required for catalytic activity in Chs2 (Nagahashi et al., *J. Biol. Chem.*, 270, 13961 (1995)) are conserved within the large predicted cytoplasmic loop of mouse Has2 (FIG. 6B). It has been suggested that these catalytic residues may be generally conserved within glycosyltransferases that catalyze the synthesis of oligosaccharides with β1→4 linkages (Nagahashi et al., supra). Significantly, the predicted cytoplasmic loop of the Has2 molecule is the most highly conserved across species, and thus this part of the protein may form the catalytic domain.

EXAMPLE 2

Molecular Biochemical Characterization of Mouse Has2

Northern and Southern Analysis. Mouse multiple tissue Northern (MTN) Blots (CLONTECH, Palo Alto, Calif.) were hybridized to a [$^{32}$P]dCTP-labeled cDNA probe corresponding to the 1.65 kb open-reading-frame (ORF) of the mouse Has2 gene. Blots were hybridized at 42° C. and washed to high stringency according to the manufacturer's recommendations. The mouse embryo blot was exposed overnight at −70° C. to BioMax MR film (Eastman Kodak Company, New Haven, Conn.) with two intensifying screens, whereas the adult tissue blot was exposed for six days at −70° C. with two screens. To control for variation in loading, both blots were stripped, and rehybridized with a mouse glyceraldehyde-3-phosphate dehydrogenase (GAPDH) probe. Both GAPDH hybridized blots were exposed for one hour at −70° C. with two screens.

Figure 7:
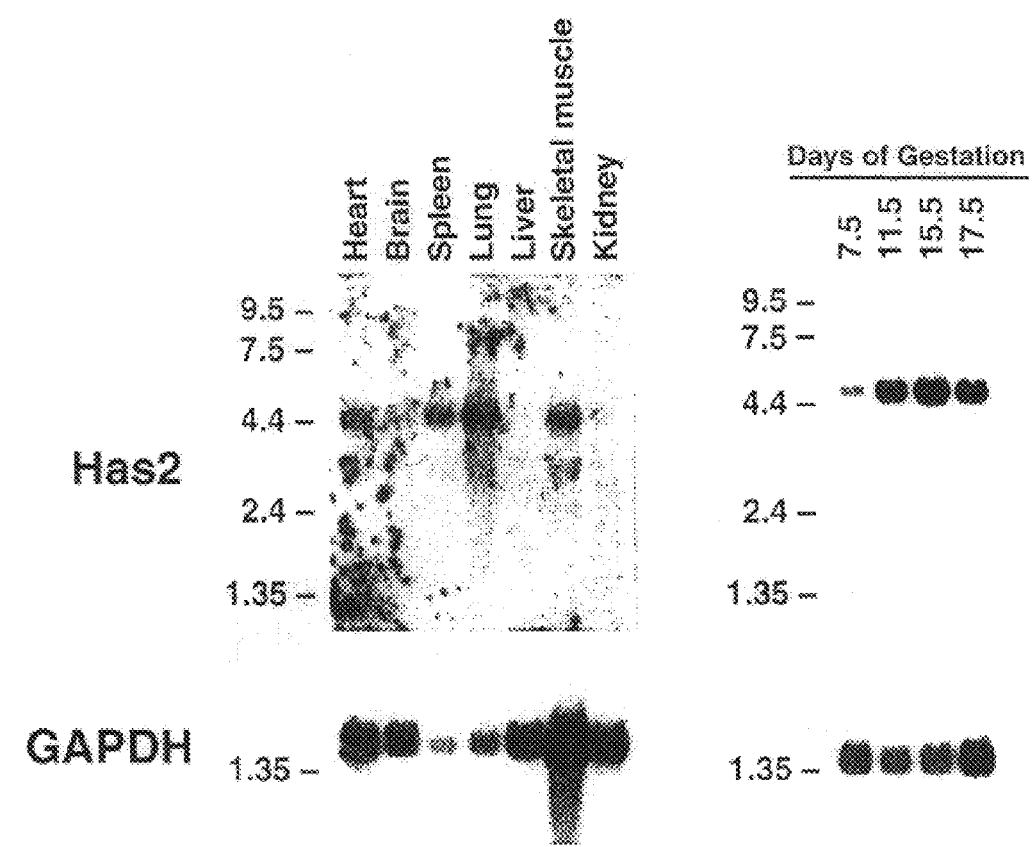
FIG. 7. Northern analyses of mouse Has2 expression. Multiple tissue Northern blots of polyA$^+$ RNA isolated from mouse embryos and adult tissues were hybridized with a mouse Has2 ORF cDNA probe. The relative positions of RNA molecular weight markers are indicated at the left of each blot. A GAPDH probe was employed as an internal control.

Northern analyses detected two transcripts of approximately 3.2 kb and 4.8 kb, respectively, in embryonic samples (FIG. 7). Only the 4.8 kb message was observed in RNA from adult tissues. The 4.8 kb transcript was expressed at levels approximately 20 fold higher than the 3.2 kb transcript. High levels of expression were observed in the developing mouse embryo, in addition to lower levels in adult mouse heart, brain, spleen, lung and skeletal muscle (FIG. 6). All of the isolated cDNA clones were predicted to form an identical ORF. Thus, rather than being the result of alternate splicing, the 4.8 kb transcript most probably corresponds to a mouse Has2 mRNA with an alternate polyA signal, generating a 3' UTR with approximately 1.8 kb of sequence, in addition to that reported herein.

Moreover, the observed expression pattern of mouse Has2, i.e., Has2 expression was detected in the primitive streak stage embryo (7.5 dpc) and an increase in Has2 expression in the later embryo, correlates well with the previously described expression pattern of HA. HA has previously been observed at significant levels starting as early as the egg cylinder stage (5.5 dpc), when it is secreted into the expanding yolk cavity. Thus, HA may play a role in the formation and expansion of embryonic cavities. From 9.5 dpc, synthesis increases, and the HA assumes more of a pericellular distribution, rather than being primarily associated with fluid-filled spaces. HA is present at high levels within the developing vertebral column, the neural crest-derived mesenchyme of the craniofacial region, and the heart and smooth muscle throughout the mid-gestation embryo.

In the adult, Has2 expression was detected in heart, brain, spleen, lung and skeletal muscle, but not in liver or kidney (FIG. 7). The level of expression of Has2 was markedly reduced in adult tissues as compared to the embryo.

Mouse 129Sv/J genomic DNA was prepared from tail snips using standard procedures. Approximately 15 μg samples of genomic DNA were digested overnight with restriction endonucleases, size-separated through 0.8% agarose gels, and transferred to Hybond N+ nylon membranes (Amersham, Arlington Heights, Ill.). Membranes were hybridized to a [$^{32}$P]dCTP-labeled cDNA probe corresponding to the 1.65 kb ORF of mouse Has2. Hybridization conditions were performed as recommended by the manufacturer. Membranes were washed to low (1×SSC+0.1% SDS at 37° C.) and high (0.1×SSC+0.1% SDS at 55° C.) stringency (1×SSC (saline sodium citrate) is 150 mM NaCl, 15 mM Na citrate) and autoradiography was performed as described above.

Figure 8:
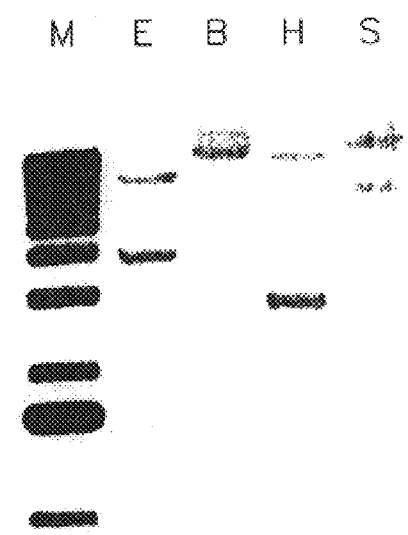
FIG. 8. Southern analysis of mouse Has2. Total 129Sv/J mouse genomic DNA was digested with the restriction enzymes, E (EcoRI), B (BamHI), H (HindIII), and S (SacI) and probed with a labeled mouse Has2 ORF cDNA. "M" indicates 1 kilobase pair ladder.

The pattern of hybridizing restriction fragments that was observed through Southern analyses was consistent with mouse Has2 being a single copy gene within the mouse genome (FIG. 8). In addition, the pattern observed in digests of total mouse genomic DNA was identical to that observed in equivalent digests of recently isolated mouse Has2 genomic clones. Low stringency wash conditions failed to identify any further hybridizing fragments including those fragments corresponding to the related mouse Has 1 (Itano et al., supra) gene. This suggests that the level of sequence identity (55%) between mouse Has2 and mouse Has1, and possibly other Has-related genes, is not sufficient to permit detection through Southern hybridization even at low stringency. Thus, while these results preclude the existence of a mouse Has2 pseudogene, they do not preclude the existence of other genes related to mouse Has2 and mouse Has1.

Transfection Studies. To investigate the potential role of mouse Has2 in HA biosynthesis, expression constructs were created in the mammalian expression vector, pCIneo (Promega Corporation, Madison, Wis.). Mouse Has2 ORFs were amplified by PCR, from a template of mouse Has cDNA clone λ11.1 (FIG. 2). PCR primers were designed to create a mouse Has2 cDNA with an optimized Kozak consensus A—ATGG, and to contain SmaI/XmaI sites at each end suitable for cloning. Primers were as follows: 5'-CCCGGGCAAG ATG GAT TGT GAG AGG TTT CTA TGT GTC CTG -3' (SEQ ID NO:21, bps 504 to 537, FIG. 3) and 5'-CCCGGG TCA TAC ATC AAG CAC CAT GTC ATA CTG-3' (SEQ ID NO:22, bps 2163 to 2137, FIG. 3). Gel-purified PCR products were cloned directly into a pBluescript KSII+T-vector for sequence verification, prior to subcloning into the XmaI site of pCIneo.

The mouse Has2 expression vector was co-transfected with a cytomegalovirus promoter (CMV) driven β-gal expression vector into COS-1 (SV40-transformed African green monkey kidney) cells (Gluzman, *Cell,* 23, 175 (1981)) using Lipofectamine™ (GIBCO-BRL/Life Technologies, Gaithersburg, Md.), according to the manufacturer's instructions. The β-gal expression plasmid was used in all transfections to permit the visual identification of cells that had been successfully transfected. Control co-transfections were pCIneo (vector control) and LacZ vector. Cells were analyzed 36 hours after lipofection (transient transfection). The COS-1 cell line and the mouse 3T6 (Swiss embryonic fibroblast) cell line were routinely maintained at 37° C. in Dulbecco's modified Eagle's medium (DMEM) supplemented with 10% fetal bovine serum (FBS) and 2 mM L-glutamine, in a humidified chamber at 5% $CO_2$.

HA Coat Assays. Glutaraldehyde fixed horse erythrocytes (Sigma Chemical Company, St. Louis, Mo.) were reconstituted in phosphate-buffered saline (PBS), washed several times to remove traces of sodium azide, and finally resuspended in PBS plus 1 mg/ml BSA to a density of $5×10^8$ cells/ml. HA coats were visualized around live cells growing in individual wells of a 24-well plate or 6-well plate by adding $1×10^7$ or $5×10^7$ red blood cells, respectively, to the growth medium. Red cells were allowed to settle for 15 minutes before HA coats were scored. To confirm the coats as being composed of HA, red cells were removed by extensive washing with PBS, and one well of each experimental sample was treated with 10 units/ml bovine testicular hyaluronidase (CALBIOCHEM, San Diego, Calif.) or 5 units/ml Streptomyces hyaluronidase (CALBIOCHEM, San Diego, Calif.) in DMEM plus 0.5% FBS for 1 hour at 37° C. Equivalent wells were incubated under the same conditions in the absence of hyaluronidase. After incubation, red cells were added to the wells, as previously described, and coats were again scored. HA coats were imaged at 200× magnification. After imaging, red cells were removed by extensive washing with PBS. Cells were stained to detect β-galactosidase (LacZ) activity and imaged as described by Sanes et al. *EMBO J.,* 5, 3133 (1986).

Parental, untransfected COS-1 cells had no detectable coat-forming ability in HA pericellular coat-forming assays (FIG. 9B). In contrast, untransfected 3T6 mouse embryonic fibroblast cells had well-developed HA coats (FIG. 9A). Transient co-transfection of mouse Has2 and LacZ expression constructs into COS-1 cells resulted in the production of large HA coats (FIGS. 9D-I). Cells acquiring an HA coat also stained positively for β-gal activity (FIGS. 9D-I), confirming that cells that had generated HA coats had successfully taken up DNA. HA coats were destroyed by treatment with Streptomyces hyaluronidase (FIG. 9H) or bovine testicular hyaluronidase. Control pCIneo transfected cells produced no coats (FIG. 9C), and were indistinguishable from parental untransfected COS-1 cells. Equivalent numbers of LacZ positive cells were observed in experimental and control transfections.

These results indicate that parental COS-1 cells express all other factors required for HA biosynthesis and pericellular coat formation, but most likely lack HA synthase activity. Thus, expression of Has2 in COS-1 cells is sufficient for HA coat formation.

Discussion

Residues demonstrated to be critical in terms of the β1→4 glycosyltransferase activity of yeast Chs2 were conserved in mouse Has2, mouse Has 1, Streptococcal HasA, Xenopus DG42 and Rhizobium NodC. Thus, it is likely that mouse Has proteins have β1→4 glycosyltransferase activity. Furthermore, although overall sequence identity between mouse Has2 and *Streptococcus pyogenes* HasA was only 21%, a 180 amino acid region within the predicted intracellular loop (residues 182 to 361) was highly conserved. This region exhibited 54% similarity between mouse Has2 and bacterial HasA, and greater than 80% similarity between mouse Has2, mouse Has1, and Xenopus DG42. This level of sequence conservation suggests that these proteins are functionally related.

Sequence analyses predicted that mouse Has2 and Has3 encode a membrane protein with multiple transmembrane domains, similar in structure to the bacterial HasA protein and mouse Has1. Significantly, four consensus binding sites for HA were identified in Has2, three of which were predicted to be intracellular. These sites may thus represent areas of potential binding of HA chains during elongation, and/or may represent sites at which the newly synthesized HA polymer remains attached prior to release from the cell. In addition to putative HA binding sites, numerous consensus sequences for phosphorylation by PKC and cAMP-dependent kinases were identified within the predicted intracellular loop of the molecule. This is significant, as mammalian HA biosynthesis has been shown to be dependent on activation by PKC, and suggests that the PKC dependence may partly involve direct activation of Has2 through phosphorylation.

HA-dependent pericellular coats have been proposed to form through two alternate mechanisms. The first mechanism is HA receptor-dependent and HA synthesis independent. This type of coat can form through association of HA with cell surface HA receptors, and stabilization of the coat by association of HA binding proteoglycans, such as aggrecan and link protein (Lee et al., *J. Cell Biol.,* 123, 1899 (1993); Knudson et al., *Proc. Natl. Acad. Sci. USA,* 90, 4003 (1993)). Presumably, this permits cells expressing HA receptors to enter an environment rich in HA, and to organize an HA matrix around themselves that is independent of the ability to synthesize HA.

The second mechanism is HA receptor independent, and requires the synthesis and extrusion of HA through the plasma membrane. It has been proposed that the extruded HA associates with the membrane through continued attachment to the synthase, and that this coat is stabilized by HA-HA and HA-protein bridges (Heldin et al., *Exp. Cell Res.,* 208, 422 (1993)).

Figure 9:
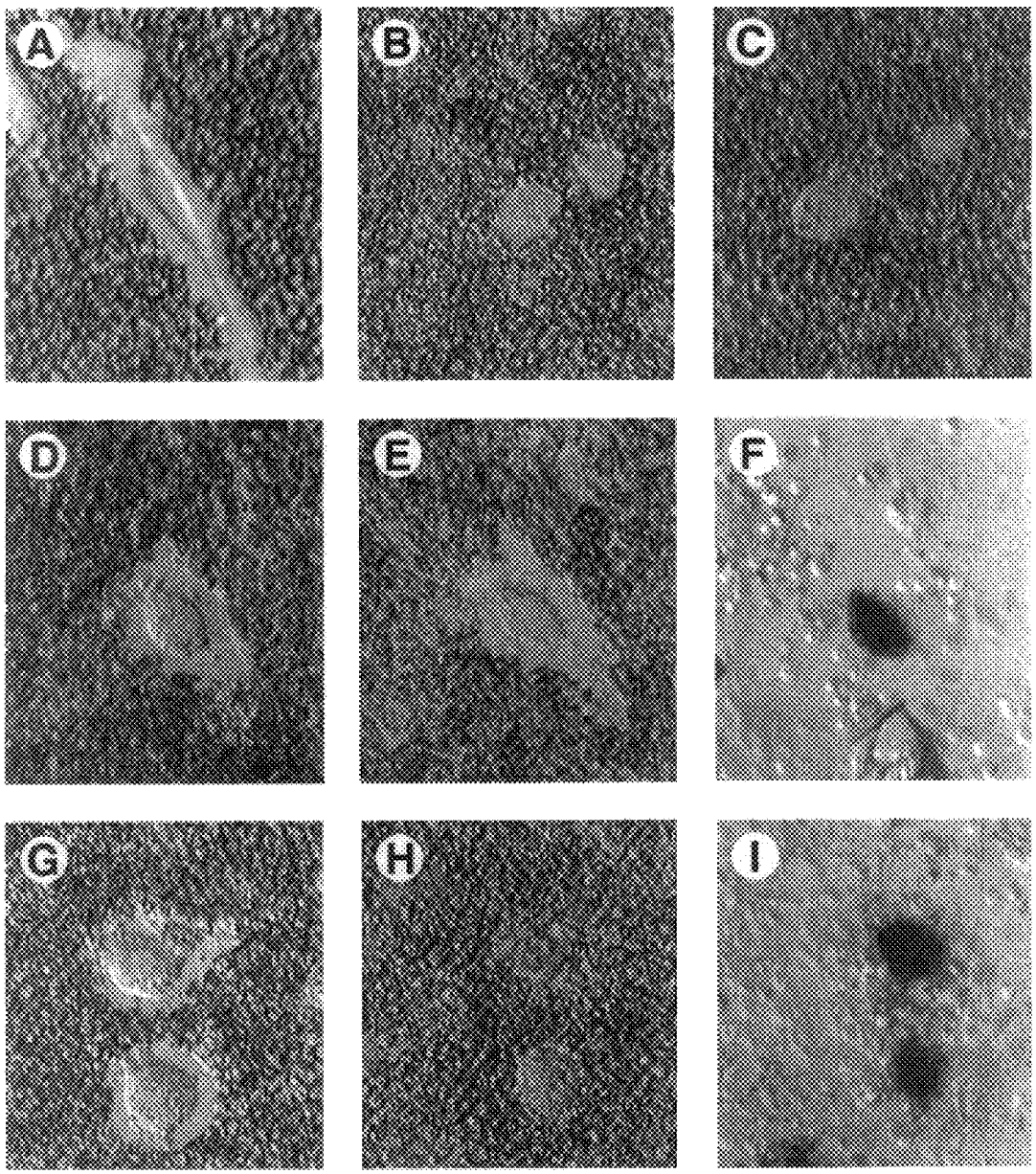
FIG. 9. COS-1 cells expressing mouse Has2 hyaluronan coats. HA coats were detected by a particle exclusion assay (see Clarris et al., *Exp. Cell Res.*, 49, 181 (1986)). (A) Mouse 3T6 embryonic fibroblasts. (B) COS-1 cells. (C) COS-1 cells co-transfected with a β-gal expression vector and pCIneo control vector. (D-I) COS-1 cells co-transfected with a vector which expresses mouse Has2 and a vector which expresses β-gal. (E) Co-transfected COS-1 cells which were maintained in starvation-medium. (F and I) Co-transfected COS-1 cells stained for β-gal activity. (H) Co-transfected COS-1 cells which were maintained in starvation-medium containing hyaluronidase.

Expression of mouse Has2 by COS-1 cells resulted in the formation of large well-pronounced HA coats, as determined by a particle exclusion assay (FIG. 9). Previous studies in COS cells have shown that transfection of the HA receptor, CD44, and the addition of exogenous HA (15 μg/ml) and proteoglycans to the medium was required for HA-dependent pericellular matrix formation (Knudson et al., *Proc. Natl. Acad. Sci. USA,* 90, 4003 (1993)). In contrast, the studies described hereinabove demonstrate that expression of mouse Has2 in COS cells, in the absence of HA receptor expression, exogenously added HA, or proteoglycans, was sufficient for HA coat formation. This suggests that Has2 expression leads to the synthesis of HA, which is extruded through the plasma membrane and may associate with the cell surface to form an HA coat through continued attachment to the synthase. In this respect, the consensus HA binding motifs predicted within mouse Has2 may play an important role.

HA biosynthesis requires two enzyme activities; the transfer of UDP-N-acetylglucosamine (UDP-GlcNAc) and UDP-glucuronic acid (UDP-GlcUA), respectively, to the growing HA chain (Philipson et al., *Biochemistry* 24, 7899 (1985)).

In *S. pyogenes*, a single enzyme, HasA, carries out both activities. In contrast, recombinant Xenopus DG42 protein can synthesize short chitin oligomers from UDP-GlcNAc in vitro, but cannot synthesize a hyaluronan chain in the presence of UDP-GlcNAc and UDP-GlcUA (Semino et al., *Proc. Natl. Acad. USA*, 92, 3498 (1995)). This suggests that eukaryotic HA synthesis requires DG42-like activity and a second enzyme activity provided by a separate protein.

EXAMPLE 3 cDNA Cloning and Characterization of Human Hyaluronan Synthase-2 and Mouse and Human Hyaluronan Synthase-3

Using degenerate PCR primer pair DEG 1 and DEG 5, described in Example 1, PCR products of approximately 300 bp were amplified from human and mouse total genomic DNA. The templates for PCR were 100 ng of human T47D mammary carcinoma cell line genomic DNA, and 100 ng of mouse 129 Sv/J genomic DNA. Cycling parameters were as follows: 35 cycles of 94° C. for 10 seconds, 50° C. for 30 seconds, and 72° C. for 1 minute, followed by a final extension step at 72° C. for 10 minutes. Amplified fragments of the expected size were identified through agarose gel electrophoresis, gel-purified, and cloned directly as described in Example 1.

Figures 1, 14C:
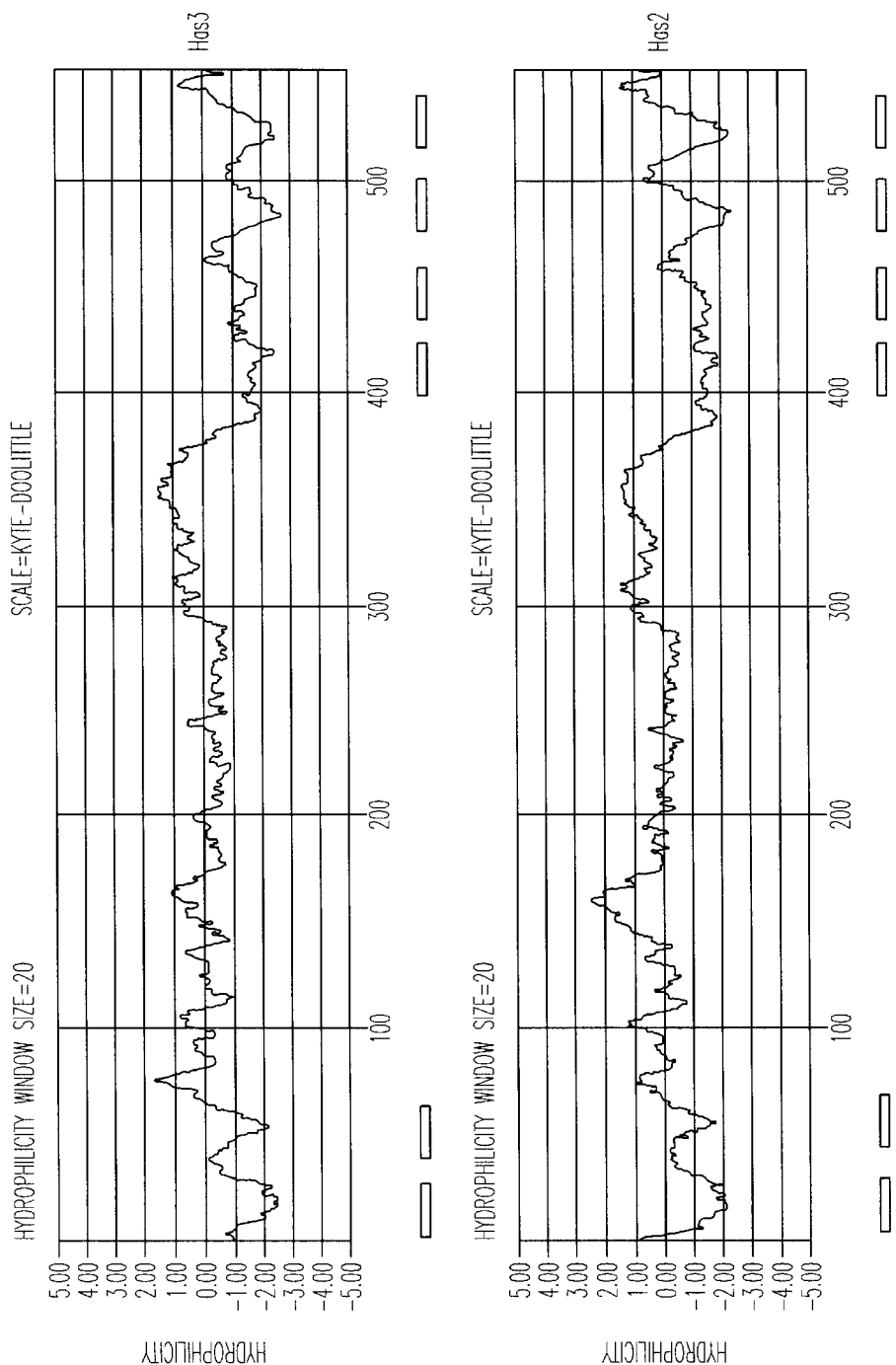
Figures 2, 14C:
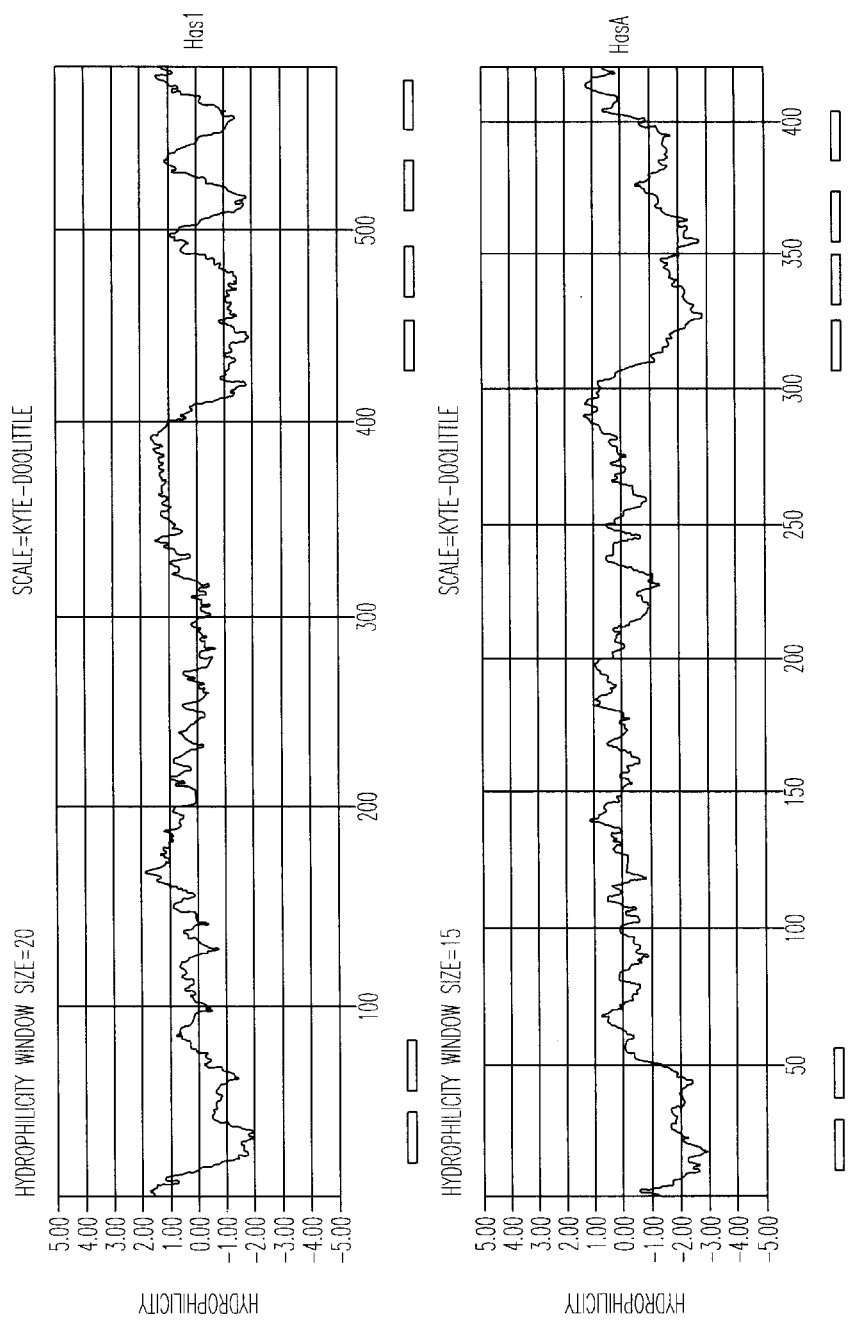

Two additional degenerate oligonucleotide primer pools (DEG 10 and DEG 11) were designed, based upon the conserved amino acid sequences GWGTSGRK (SEQ ID NO:20) and RWLNQQTRW (SEQ ID NO:33) (see FIG. 14). Similar PCR conditions were used to amplify fragments of the expected size from human and mouse genomic DNA using these degenerate primers. Amplified PCR products were gel-purified and ligated directly into a cloning vector for sequence analyses.

Sequences obtained from the clones fell into two groups in both the mouse and human. One group of human clones, represented by SEQ ID NO:23, shared 88% sequence identity with the equivalent region of mouse Has2 (SEQ ID NO:1) (FIG. 10C), and was 100% identical at the amino acid level to SEQ ID NO:2 (FIG. 10D). Thus, SEQ ID NO:23 represents a partial nucleotide sequence of human Has2. A human fetal lung expressed sequence tag (EST) (Genbank Accession No. W21505) shares approximately 90% nucleotide sequence identity with SEQ ID NO:1, and close to 100% amino acid identity to the predicted carboxy-terminal end of SEQ ID NO:2.

The second group of clones obtained through degenerate PCR, although clearly related to Has2 and Has1, were unique. The genes present in these clones has been designated Has3 (FIG. 11). The mouse and human Has3 genes share 93% nucleotide identity (SEQ ID Nos. 26 and 25, respectively) and 99% amino acid identity (SEQ ID Nos. 28 and 27, respectively).

Based upon the sequence of these partial fragments, a single pair of oligonucleotide primers, forward 5'-TAC TGG ATG GCT TTC AAC GTG GAG-3' (corresponding to nucleotides 790 to 813, SEQ ID NO:34, FIG. 12B), and reverse 5'-GTC ATC CAG AGG TGG TGC TTA TGG-3' (corresponding to antisense complement of nucleotides 1142 to 1119, SEQ ID NO:37, FIG. 12B) were employed to facilitate PCR screening of a mouse 129Sv P1 genomic library (Genome Systems, St. Louis, Mo.). Three positive P1 clones were obtained. The restriction fragments spanning the entire mouse Has3 gene were identified, the inserts comprising the fragments subcloned into pBluescript (Stratagene, La Jolla, Calif.) based vectors and the inserts sequenced.

To confirm the sequence obtained from the analysis of genomic clones, the Has 3 cDNA was obtained. The cDNA was cloned by reverse-transcriptase polymerase chain reaction (RT-PCR) amplification. The template for the reaction was total RNA from late gestation (17.5 days post-coitum) mouse C57BL/6J embryos. First-strand cDNA synthesis was performed as described in Example 1 using the mouse Has3 reverse oligonucleotide primer.

First-strand cDNAs were PCR amplified using standard PCR buffer conditions supplemented with 2% deionized formamide, through 35 cycles of 94° C. for 10 seconds, 65° C. for 30 seconds, and 72° C. for 2 minutes, followed by a final extension step of 72° C. for 10 minutes. Oligonucleotide primers possessed EcoRI restriction endonuclease sites (underlined) at their 5' termini to facilitate subsequent cloning steps. These oligonucleotides included: forward, 5'-CC GAATTAAG ATG GCG GTG CAG CTG ACT ACA GCC-3' (corresponding to nucleotides 1 to 24, SEQ ID NO:38, FIG. 12B), and reverse, 5' CCGAATTC TCA CAC CTC CGC AAA AGC CAG GC-3' (corresponding to the antisense complement of nucleotides 1665 to 1643, SEQ ID NO:39, FIG. 12B). Amplified cDNAs of the expected size were gel-purified and cloned. All sequence analyses were performed using the Genetics Computer Group (GCG) package, and MacVector programs.

The open reading frame (ORF) encoding mouse Has3 is 1662 bp (SEQ ID NO:31) (FIG. 12B). This ORF encodes a polypeptide of 554 amino acids (SEQ ID NO:32) with a predicted molecular mass of 63.3 kDa. This polypeptide is only 2 amino acids longer than the mouse Has2 polypeptide. Sequence alignments indicated that mouse Has3 is 71%, 57%, 56%, and 28% identical to mouse Has2, mouse Has1 (HAS protein), Xenopus DG42, and *Streptococcus pyogenes* HasA, respectively (FIG. 13A). Like Has1 and Has2, residues demonstrated to be critical for N-acetylglucosaminyltransferase activity of yeast chitin synthase 2 are completely conserved. In addition, these residues are conserved with members of a recently identified putative plant cellulose synthase family (Pear et al., *Proc. Natl. Acad Sci. USA*, 93, 12637 (1996)) (FIG. 13B).

Alignment of the partial sequence of human has3 (HAS3 hereinafter) and mouse Has3 (Has3 hereinafter) indicated a very high level of sequence conservation (99%) (FIG. 12A). This is similar to the high level of conservation observed for human and mouse HAS 1 (96%) and HAS2 (99%).

Hydrophilicity plots suggested that Has3 is very similar in structure to Has2 and Has 1, and predicted the presence of multiple transmembrane domains, with two at the N-terminus and a cluster at the C-terminus (FIG. 14C). Significantly, like Has2 and Has1, the Has3 sequence predicts the presence of several potential HA binding motifs defined by the consensus B $(X_7)$B (underlined in FIG. 12B). Furthermore, these motifs are located at similar positions within the Has3 polypeptide.

EXAMPLE 4

Molecular Biochemical Characterization of Mouse Has3

Figure 13:
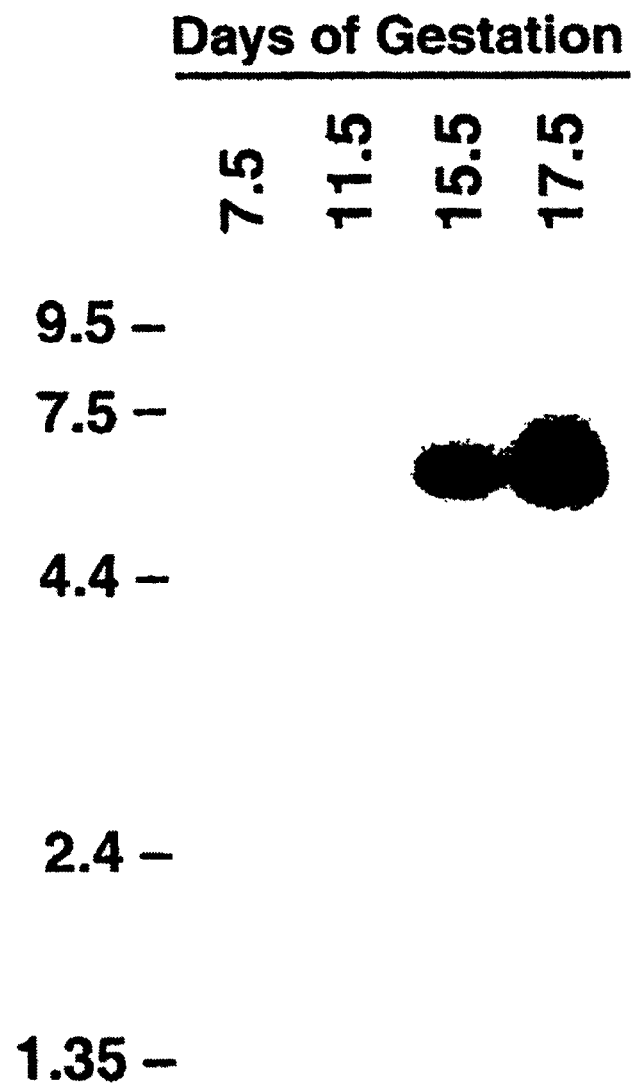
FIG. 13. Northern blot depicting the expression of mouse Has3 at four different stages of mouse embryonic development. A cDNA probe representing the mouse Has3 ORF was radiolabeled and hybridized to a blot containing mouse embryonic polyA+RNAs (CLONTECH) under conditions recommended by the manufacturer.

Northern Analysis. To determine the temporal expression pattern of mouse Has3 in the developing mouse embryo, Northern blot analysis was employed. The mouse Has3 ORF cDNA was labeled with [$\alpha^{32}$P]dCTP by random priming (Feinberg and Vogelstein, *Anal. Biochem.*, 132, 6 (1984)) and hybridized to a Northern blot of mouse embryo messenger RNA (CLONTECH, Palo Alto, Calif.) under conditions recommended by the manufacturer. The results showed that, in contrast to mouse Has2 which is highly expressed from as early as day 7.5 post-coitum through late gestation in the developing mouse embryo, mouse Has3 is expressed predominantly in the late gestation embryo (FIG. 13). One major transcript of approximately 6.0–6.5 kb and a minor transcript of approximately 4.0 kb were observed (FIG. 13).

Figure 15:
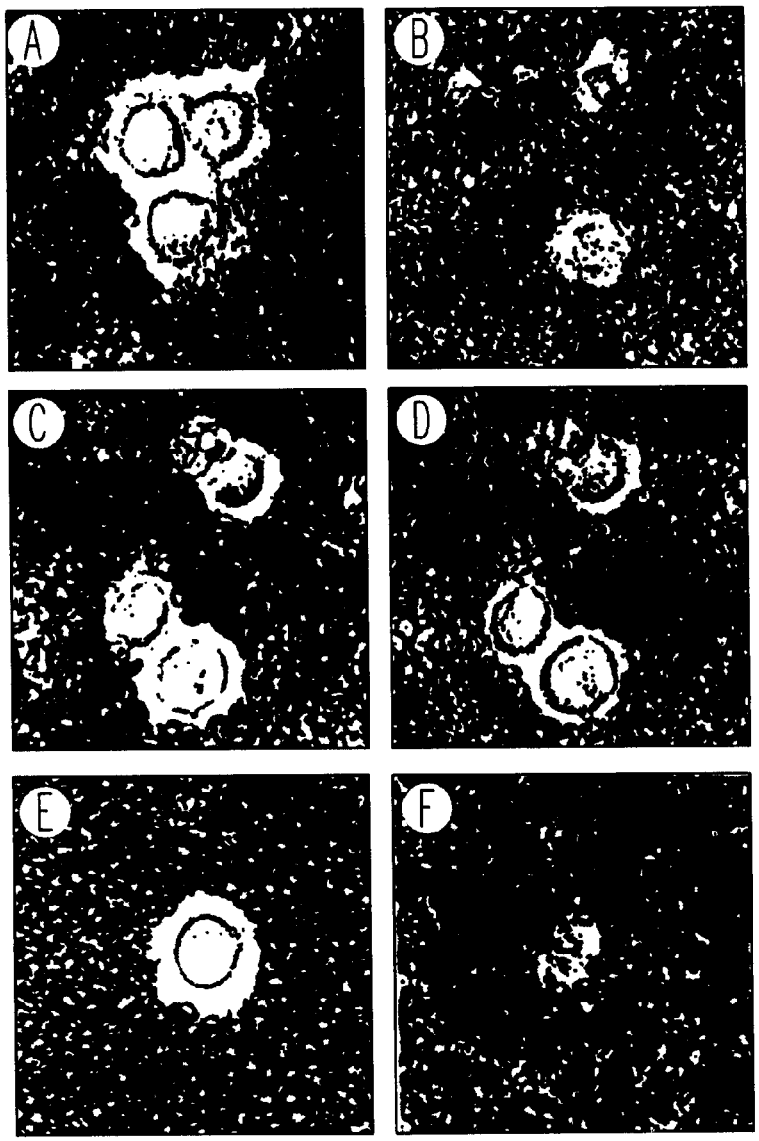
FIG. 15. COS-1 cells expressing mouse Has 3 hyaluronan coats. HA coats were detected as described in the legend to FIG. 9. (A) COS-1 cells co-transfected with a β-gal expression vector and a vector which expresses mouse Has2. (B) COS-1 cells co-transfected with a β-gal expression vector and pCIneo control vector. (C) COS-1 cells co-transfected with a vector which expresses mouse Has3 and a vector which expresses β-gal before mock treatment with hylauronidase. (D) COS-1 cells co-transfected with a vector which expresses mouse Has3 and a vector which expresses β-gal after mock treatment with hylauronidase. (E) COS-1 cells co-transfected with a vector which expresses mouse Has3 and a vector which expresses β-gal before treatment with hylauronidase. (F) COS-1 cells co-transfected with a vector which expresses mouse Has3 and a vector which expresses β-gal after treatment with hylauronidase.

Transfection Studies. The mouse Has3 ORF was cloned into the EcoRI site of the expression vector pCIneo (Promega, Madison, Wis.). To test the enzyme activity of mouse Has3, the mouse Has3 expression vector was co-transfected with a pCMV β-gal vector into COS-1 (SV40-transformed African green monkey kidney) cells using LipofectAMINE™ (Life Technologies Inc., Gaithersburg, Md.), according to the manufacturer's instructions. Positive control transfections utilized the mouse Has2 expression vector described above. HA coat assays and detection of β-galactosidase activity were performed as described in Example 2.

pCIneo (vector only control) transfected cells failed to produce coats (FIG. 15B). Mouse Has3 transfected cells produced pericellular coats that were destroyed by treatment with a specific hyaluronidase from Streptomyces (5 TRU/ml for 1 hour at 37° C.) (compare panels E, before hyaluronidase treatment, and F, after hyaluronidase treatment, in FIG. 15). In contrast, pericellular coats remained on mock hyaluronidase treated cells (compare panels C, before, and D, after mock hyaluronidase treatment in FIG. 15). Thus, the data showed that expression of mouse Has3 in COS-1 cells resulted in the generation of well-pronounced HA-dependent pericellular coats, as previously observed for Has 2.

To confirm the HA biosynthetic capability of Has3 transfected cells, HA synthase assays were performed on crude membranes prepared from these cells. Crude cell membrane preparations were isolated as described by Becq et al. (*Proc. Natl. Acad. Sci. USA*, 91, 9160 (1994)), except the final membrane pellets were resuspended in 50 μl of lysis buffer (LB) consisting of 10 mM KCl, 1.5 mM $MgCl_2$, and 10 mM Tris-HCl pH 7.4 plus protease inhibitors (aprotinin, leupeptin and phenylmethylsulfonyl fluoride) (LB+). Protein content of crude membrane preparations was determined by a BCA assay (Pierce, Rockford, Ill.). To detect HA synthase activity, duplicate samples of approximately 100 μg crude membrane protein were incubated overnight at 37° C. in a total reaction volume of 200 μl under the following conditions: 5 mM dithiothreitol, 15 mM $MgCl_2$, 25 mM HEPES pH 7.1, 1 mM UDP-GlcNAc, 0.05 mM UDP-GlcUA, 0.4 μg aprotinin, 0.4 μg leupeptin, 0.5 μCi UDP-[$^{14}$C]GlcUA (ICN, Costa Mesa, Calif.). An additional specificity control reaction was set up in which UDP-GlcNAc was omitted. After overnight incubation, samples were boiled for 10 minutes, and subsequently divided in two equal portions. Streptomyces hyaluronidase (1 turbidity reducing unit (TRU)) was added to one half and incubated for an additional hour at 37° C. SDS was added to a final concentration of 1%, samples were boiled and analyzed by descending paper chromatography essentially as described in DeAngelis and Weegel, *Biochemistry*, 33, 9033 (1994).

These assays indicated that crude membranes prepared from either Has3 or Has2 transfected COS-1 cells were capable of converting UDP-[$^{14}$C]GlcUA into significant amounts of a high molecular weight product only in the presence of UDP-GlcNAc (Table 2). Furthermore, this product could be specifically degraded by Streptomyces hyaluronidase (Table 2). Thus, in COS-1 cells, Has2 and Has3 appear to possess similar enzymatic activities.

TABLE 2

Hyaluronan Synthase Activity of Transfected COS-1 Cells

| Vector | +UDP-GlcNAc[a] | −UDP-GlcNAc | Hyaluronidase[b] |
|---|---|---|---|
| Mouse Has3 | 204.2[c] | 1.9[d] | − |
| pCIneo | 65.0 | 2.2 | + |
| Mouse Has2 | 26.9 | 2.5 | − |
| pCIneo | 10.5 | 2.0 | + |
| pCIneo (control) | 11.0 | ND[e] | − |
|  | 10.3 | ND | + |

[a]Plus and minus symbols indicate whether or not UDP-GlcNAc was included in these reactions.
[b]Plus and minus symbols indicate whether or not a reaction was subsequently treated for 1 hour at 37° C. with 1 TRU Streptomyces hyaluronidase prior to paper chromatography.
[c]Numbers represent picomoles radiolabeled product formed and were calculated taking into account the specific activity of the UDP[$^{14}$C]-GlcUA used, the amount of cold UDP-GlcUA per reaction, and assumed a scintillation counting efficiency of >95%. Based upon these calculations, 1 picomole of radiolabeled product is represented by 384 disintegrations per minute (dpm), i.e., 204.2 picomoles product was calculated from 78, 413 dpm. Numbers represent the mean calculated from duplicate reactions.
[d]Number represents the result of a single reaction in each instance.
[e]Not determined.

Discussion.

The three Has proteins are encoded by three separate but related genes, which constitute a mammalian HAS gene family. Sequence comparisons and structural predictions suggest that the mammalian HAS proteins are very similar in structure. They are predicted to have one or two N-terminal transmembrane domains and a cluster of C-terminal transmembrane domains separated by a large cytoplasmic loop. This topology is extraordinarily similar to that predicted for the bacterial HA synthase, HasA (Helderman et al., *Glycobiology*, 6, 741 (1996)), and to that recently reported for the *Rhizobium meliloti* nodulation factor, NodC (Barny et al., *Molec. Microbiol.*, 19, 443 (1996)). In addition, the mammalian HAS sequences, the Xenopus DG42 sequence, HasA sequence, NodC sequence, and the recently reported putative plant cellulose synthases share critical residues shown to be required for N-acetylglucosaminyltransferase activity of yeast chitin synthase 2, making it highly likely that all these proteins are functionally related processive β-glycosyltransferases. The highly conserved aspartate residues may represent sites such as cation binding sites that in turn may coordinate nucleotide-sugar interaction with the enzyme.

While Semino and Robbins have postulated that DG42 and its related mammalian homologs, rather than being bona fide HA synthases, may stimulate HA production through synthesizing chitin oligosaccharide primers, which are required for and rate limiting for eukaryotic HA biosynthesis (*Proc. Natl. Acad. Sci. USA*, 93, 4548 (1996)), cell membranes isolated from baker's yeast, *Saccharomyces cerevisiae*, engineered to express DG42 have HA synthesis activity in vitro when supplied with the required UDP-precursors (DeAngelis and Achyuthan, *J. Biol. Chem.*, 271, 23657 (1996)) since *S. cerevisiae* is deficient in UDP-glucuronic acid production, *S. cerevisiae* is incapable of HA biosynthesis.

Expression of any one of the mammalian HAS proteins in transfected mammalian cells leads to a dramatic increase in HA biosynthesis. This would suggest that the proteins have similar activities. However, the high degree of sequence conservation (96–99% identity) between human and mouse HA synthases contrasts with the lower level of identity between synthases within a species (Has1/Has2, 55% identity; Has1/Has3, 57% identity; Has2/Has3, 71% identity), arguing for evolutionary conservation of functionally important residues, and for some differences in the mode of action of the three proteins. Potential differences in function of the proteins could relate to the length of the HA chain synthesized, the rate of HA synthesis, the ability to interact with cell-type specific accessory proteins, and whether or not the HA is preferentially secreted by the cell or alternatively retained by the cell in the form of a pericellular coat.

EXAMPLE 5

Identification of the Chromosomal Location of the Has Genes

To determine the chromosomal location of the mouse Has genes, a panel of DNA samples, from an interspecific cross that has been characterized for over 2,000 genetic markers throughout the mouse genome, was analyzed. The genetic markers included in this genetic map span between 50 and 80 centi-Morgans (cM) on each mouse autosome and the X chromosome (Chr), and the mapping of the reference loci in this interspecific cross are indicated with citations in an online database (data can be accessed through the internet as follows: http://www.informaticsjax.org/crossdata.html to enter the DNA Mapping Panel Data Sets from the Mouse Genome Database (MGD), then select the Seldin cross and Chromosome).

Initially, DNAs from two parental mice [C3H/HeJ-gld and (C3H/HeJ-gld x Mus spretus)F1] were digested with various restriction endonucleases and hybridized with probes specific to mouse Has1, Has2 and Has3 to determine restriction fragment length variants (RFLVs) to allow haplotype analyses. The 223 bp mouse Has1 probe was generated through PCR amplification of a full-length mouse Has1 cDNA template using oligonucleotide primers, 5'GTCA-GAGCTACTTCCACTGTG3' (SEQ ID NO:53) and 5'AAG-GAGGAGGGCGTCTCCGAG3' (SEQ ID NO:54) (nt positions 947–967 and 1169–1149, respectively). The mouse Has2 probe was the MHas300 partial cDNA (FIG. 2), and the mouse Has3 probe was an equivalent fragment of the mouse Has3 gene, generated using degenerate PCR primers as described above (Example 1). For each gene, informative RFLVs were detected: Has1 using BamHI restriction endonuclease, C2H/HeJ-gld, 18.0 kb, 6.8 kb; Mus spretus, 2.1 kb; Has2 using TaqI restriction endonuclease, C3H/HeJ-gld, 3.7 kb; Mus spretus, 3.9 kb; Has3 using MspI restriction endonuclease, C3H/HeJ-gld, 1.3 kb, 4.2 kb; Mus spretus, 3.2 kb.

Comparison of the hapotype distribution of the Has RFLVs indicated that these genes segregated to three different mouse autosomes; Has1 to mouse Chr 17, Has2 to mouse Chr 15, and Has3 to mouse Chr 8. The best gene order±the standard deviation (Green, In: Genetics and Probability in Animal Breeding Experiments (E. Green, ed.), MacMillan, N.Y., pp. 77–113 (1981)) indicated the following gene orders: on mouse Chr 17 (centromere) Thbs2—0.9 cM±0.9 cM—Has1—3.5 cM±1.7 cM—Hsp84-1; on mouse Chr 15 (centromere) Dhfr-rs1—14.0 cM±3.3 cM—Has2—0.9 cM±0.9 cM—Myc; and on mouse Chr 8 (centromere) Mt1—5.3 cM±2.1 cM—D8Mit242—0.9 cM±0.9 cM—Has3/D8Mit12—11.4 cM±3.0 cM—D8Mit154.

Pairwise sequence alignments of mouse Has cDNAs with human HAS cDNAs permitted the design of oligonucleotide primer pairs specific for the respective human HAS genes. Human HAS1: HAS1F 5'GTGCTTCTGTCGCTC-TACGCG3' (SEQ ID NO:49) and Human HAS1R 5'CCAGTCCCAATATAGTCCAGACTG3' (SEQ ID NO:50) (nt positions 1410–1431 and 1940–1917, respectively, (Shyjan et al., J. Biol. Chem., 271, 23395 (1996)) which amplified a 520 bp fragment. Human HAS2: HAS2F 5'GGTGTGTTCAGTGCATTAGTGGA3' (SEQ ID NO:51) and HAS2R 5'TAGCCATCTGAGATATTCTAT-AGGT3' (SEQ ID NO:52) (nt positions 1359–1382 and 1579–1555, respectively, Watanabe and Yamaguchi, J. Biol. Chem., 271, 22945 (1996)) which amplified a 220 bp fragment. Human HAS3: HAS3F 5'TGTGCAGTGTATT-AGTGGGCCCT3' (SEQ ID NO:41) and HAS3R 5'GTTGAGCCACCGGAGGTACTTAG3' (SEQ ID NO:43) which amplified a 220 bp fragment. Conditions used in all PCR reactions were: 0.2 mM each dNTP, 50 mM KCl, 10 mM Tris-HCl pH 8.3, 1.5 mM $MgCl_2$, 2% deionized formamide, 0.25 U Taq polymerase (Boehringer Mannheim), primers at 0.4 µM, 100 µl reactions. Cycling parameters for each primer pair were as follows: 35 cycles of 94° C. for 10 seconds, 67° C. (HAS1), 63° C. (HAS2), or 65° C. (HAS3) for 30 seconds, and 72° C. for 1 minute, followed by a final extension step at 72° C. for 10 minutes.

The oligonucleotide primers were used to screen two somatic cell hybrid mapping panels (Coriell Institute, Camden, N.J.) segregating human chromosomes on a mouse or hamster background. Using this approach, the human HAS genes were unequivocally assigned to human Chr 19 (HAS1), Chr 8 (HAS2), and Chr 16 (HAS3).

To refine the location of human HAS1 on Chr 19, the PCR fragment described above was used as a probe to screen colony filters of a Chr 19 cosmid library (Olsen et al., Genomics, 23, 659 (1994)). Two positive clones, R30674 and F21560, were identified, neither of which had been incorporated into any of the previously assembled contigs constituting the Chr 19 map (Ashworth et al., Natl. Genet., 11, 422 (1965)). Alu-PCR products (Parrish et al., Am. J. Hum. Genet., 57(5), 267 (1995)) from clone F21560 were hybridized to the cosmid library and to a genomic Bacterial Artificial Chromosome (BAC) library (Shizuya et al., Proc. Natl. Acad. Sci. USA, 89, 8794 (1992)) to form a contig around the HAS1 gene. The probe identified several additional cosmids that were members of a previously assembled contig (CT1665), which had been in situ mapped to 19q13.3, as well as two BACs (BC79672 and BC56224) which extended the HAS1 contig in the opposite direction from CT1665. Alu-PCR products from BC56224 were hybridized to cosmids and identified the HAS1 cosmids in addition to numerous clones from another previously assembled contig (CT1031). Clone D1852 from this contig has been incorporated into the high resolution pronuclear FISH map of human 19q, placing HAS1 at the q13.3–13.4 boundary, within the approximately 400 kb region between ETFB (Electron-Transferring-Flavoprotein, Beta polypeptide) and FPR1 (Formyl Peptide Receptor 1). EcoRI mapping confirmed the clone overlaps detected by hybridization and indicated a size of 286 kb for the extended HAS 1 contig. In addition to the above mapping results, the localization of HAS1to Chr 19q13.3–13.4 was confirmed using a 2.1 kb human HAS1 cDNA (Itano et al., BBRC, 222, 816 (1996)) and FISH analysis, as described in Inazawa et al. (Genomes, 17, 153 (1993)). The mapping results for mouse Has1 and human HAS1 reinforce the recently reported relationship between a small region of human 19q and mouse Chr 17.

The position of Has2 on proximal mouse Chr 15 suggested that the human homolog, HAS2, is located on the long arm of human Chr 8 at band q24.1 (DeBry and Seldin, Genomics, 33, 337 (1996) and online database: http://www3.ncbi.nlm.nih.gov/Homology/). This location corresponds to the region predicted to contain the gene for the human Langer-Giedion syndrome (LGS) (Chen et al., *Genomics*, 32, 117 (1996)), a contiguous genetic syndrome characterized by craniofacial deformities, multiple exostoses, mental retardation, microcephaly, and redundant skin (Bauermeister and Letts, *Ortho. Rev.*, 21, 31 (1962)). To refine the location of human HAS2 on Chr 8, the human HAS2 primers were used to PCR screen the following human-hamster somatic cell hybrids: CL-17, 3;8/4-1, MC2F, 21q+, and TL/UC (Parrish et al., *Som. Cell Molec. Genet.*, 20, 143 (1994); Wagner et al., *Genomics*, 10, 114 (1991)). Positive PCR signals were observed for CL-17, 21q+ and 3;8/4-1 in addition to total human DNA, sublocalizing the HAS2 gene to the q arm in interval I-8 (Spurr et al., *Cytogenet. Cell Genet*, 68, 147 (1995)). Human HAS2 primers were further screened against YACs within the distal portion of a large YAC contig (Chen et al., supra). This contig extends from interval I-1 into interval 1-9. Only three of the YACs tested were positive, narrowing the location of HAS2 to the overlapping region between these YACs. This places the human HAS2 gene at human Chr 8q24.12, close to the DAP-A1 gene, and between the defined critical region for the Langer-Giedion syndrome (LGS) and the MYC gene. Thus, HAS2 can be excluded as a candidate gene for LGS.

The localization of the mouse Has3 gene to mouse Chr 8 near the D8Mit12 locus implicated human Chr 16q as the most likely location for the human homolog of this gene. To confirm and refine this localization YAC DNA pools from a YAC map of human Chr 16 (Daggett et al., *Nature*, 377(5), 335 (1995)) were screened with DNA primers that were specific for the human HAS3 gene, as described above. Three YACs (My782G9, My703C5, and My878A4) were identified which produced an amplimer of the correct size with these primers. These results place the HAS3 gene in band 16q22.1 between the somatic cell hybrid breakpoints CY127(D) and CY6, and near the E-cadherin gene (CDH1) gene and the D16S496 marker.

All publications and patents are incorporated by reference herein, as though individually incorporated by reference. The invention is not limited to the exact details shown and described, for it should be understood that many variations and modifications may be made while remaining within the spirit and scope of the invention defined by the claims.

What is claimed is:

1. An isolated and purified DNA molecule comprising a mammalian DNA segment encoding a polypeptide having hyaluronan synthase activity, or the complement thereof, wherein the DNA segment hybridizes under hybridizing conditions to SEQ ID NO:31 or the complement thereof, and wherein the DNA segment remains hybridized to SEQ ID NO:31 or the complement thereof under stringent wash conditions at a temperature of 50° C. or greater but lower than the Tm in 0.1×SSC.

2. The DNA molecule of claim 1 wherein the DNA segment encodes a murine hyaluronan synthase.

3. The DNA molecule of claim 1 wherein the DNA segment encodes a hyaluronan synthase having SEQ ID NO:32.

4. The DNA molecule of claim 1 wherein the DNA segment comprises SEQ ID NO:31.

5. The DNA molecule of claim 1 wherein the DNA segment encodes a human hyaluronan synthase.

6. The DNA molecule of claim 5 wherein the DNA segment comprises SEQ ID NO:25.

7. The DNA molecule of claim 5 wherein the DNA segment encodes a polypeptide comprising SEQ ID NO29.

8. An expression cassette comprising a promoter operably linked to a DNA segment encoding a polypeptide having hyaluronan synthase activity or the complement thereof, wherein the DNA segment hybridizes under hybridizing conditions to SEQ ID NO:31 or the complement thereof, and wherein the DNA segment remains hybridized to SEQ ID NO:31 or the complement thereof under stringent wash conditions at a temperature of 50° C. or greater but lower than the Tm in 0.1×SSC.

9. The expression cassette of claim 8 wherein the DNA segment encodes a murine hyaluronan synthase.

10. The expression cassette of claim 8 wherein the DNA segment encodes a hyaluronan synthase having SEQ ID NO:32.

11. The expression cassette of claim 8 wherein the DNA segment comprises SEQ ID NO:31.

12. The expression cassette of claim 8 wherein the DNA segment encodes a human hyaluronan synthase.

13. The expression cassette of claim 12 wherein the DNA segment comprises SEQ ID NO:25.

14. A host cell, the genome of which is augmented by a DNA segment encoding a polypeptide having hyaluronan synthase activity or the complement thereof, wherein the DNA segment hybridizes under hybridizing conditions to SEQ ID NO:31 or the complement thereof, and wherein the DNA segment remains hybridized to SEQ ID NO:31 or the complement thereof under stringent wash conditions at a temperature of 50° C. or greater but lower than the Tm in 0.1×SSC.

15. The host cell of claim 14 wherein the DNA segment encodes a murine hyaluronan synthase.

16. The host cell of claim 14 wherein the DNA segment encodes a hyaluronan synthase having SEQ ID NO:32.

17. The host cell of claim 14 wherein the DNA segment encodes a human hyaluronan synthase.

18. A method to produce hyaluronan synthase, comprising: culturing a host cell transformed with a nucleic acid molecule comprising a promoter operably linked to a DNA segment encoding a polypeptide having hyaluronan synthase activity, so that said host cell expresses said hyaluronan synthase, wherein the DNA segment hybridizes under hybridizing conditions to SEQ ID NO:31 or the complement thereof, and wherein the DNA segment remains hybridized to SEQ ID NO:31 or the complement thereof under stringent wash conditions at a temperature of 50° C. or greater but lower than the Tm in 0.1×SSC.

19. The method of claim 18 further comprising isolating hyaluronan synthase from the host cell.

20. The method of claim 18 wherein the DNA segment encodes a murine hyaluronan synthase.

21. The method of claim 20 wherein the DNA segment comprises SEQ ID NO:31.

22. The method of claim 18 wherein the DNA segment encodes a hyaluronan synthase having SEQ ID NO:32.

23. The method of claim 18 wherein the DNA segment encodes a human hyaluronan synthase.

24. The method of claim 23 wherein the DNA segment comprises SEQ ID NO:25.

* * * * *

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
      (A) LENGTH: 2947 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ACATGTAAGA AGAAGGAGAA GTCAAGGCGT CTGGAAAGAA TTACCCAGTC CTGGCTTCGA      60

GCAGCCCATT GAACGGGGGA CTTGAACCAG CCAAAGACTT CTTCATTCTG CTCTTGCTAG     120

ACTCTGCTGA GTCTTGACCC GGCTTGTAGG TTGATGTGAA AAGAGATTTT GTGTCGTCGG     180

AGGGAAGGGG ATTGGAGCAA ATAGCAAAAC AGGGGGAAAA GTTAATTTAT CTTTAAAGCA     240

GATATAACAA AGAATTAGAA GACTTAAGTG CAGCGGAAAT ATAAAGAGAA TATTAGTGAA     300

ATTTCTTCTC AAAGAGGGGA GAACCAAGCA TTTAAGGCTC CCCCATCTTT TTTTTTAAAT     360

GTTGTTTTTA AATTTCTTAT TTTTTTTGGC CGGTCGTCTC AAATTCATCT GATTTCTTAT     420

TACCTCAATT TTGGAAACTT CCTTCCACGA CCCTCCGGGA CCACACAGAC AGGCGGAGGA     480

CGAGTCTATG AGCAGGAGCT GAACAAGATG CATTGTGAGA GGTTTCTATG TGTCCTGAGA     540

ATAATTGGAA CTACACTTTT TGGAGTGTCT CTCCTCCTCG GAATCACAGC TGCTTATATT     600

GTTGGCTACC AGTTTATCCA AACAGATAAT TACTACTTCT CATTTGGACT GTACGGTGCC     660

TTTTTAGCCT CGCATCTCAT CATCCAAAGC CTCTTTGCCT TTTTGGAACA CCGGAAAATG     720

AAGAAGTCCC TTGAAACCCC GATTAAATTG AACAAAACGG TAGCACTCTG CATCGCTGCG     780

TACCAAGAGG ACCCTGACTA CTTACGGAAA TGTTTGCAAT CTGTGAAAAG GCTGACCTAC     840

CCTGGGATTA AAGTCGTGAT GGTCATCGAT GGGAACTCAG ACGACGACCT TTACATGATG     900
```

-continued

```
GACATATTCA GCGAAGTTAT TGGCAGGGAC AAATCGGCCA CGTACATCTG GAAGAACAAC      960

TTTCATGAAA AGGGACCTGG TGAGACAGAA GAGTCCCATA AGAAAGTTC ACAACATGTC      1020

ACCCAATTGG TCTTGTCTAA CAAAAGTATT TGCATCATGC AAAAATGGGG TGGAAAGAGA     1080

GAAGTCATGT ACACAGCCTT CAGAGCACTG GGGCGAAGCG TGGATTATGT ACAGGTGTGT     1140

GACTCAGATA CTATGCTTGA CCCTGCCTCA TCTGTGGAGA TGGTGAAGGT CTTAGAGGAA     1200

GACCCTATGG TTGGAGGTGT TGGAGGAGAT GTCCAGATTT TAAACAAGTA TGATTCCTGG     1260

ATCTCCTTCC TCAGCAGCGT GAGATACTGG ATGGCTTTTA ATATAGAAAG GGCCTGCCAG     1320

TCTTATTTTG GCTGTGTCCA GTGCATAAGC GGTCCTCTGG AATGTACAG AAACTCCTTG      1380

CTGCATGAAT TTGTGGAAGA CTGGTACAAT CAGGAATTCA TGGGTAACCA ATGCAGTTTT     1440

GGTGACGACA GGCACCTTAC CAACAGGGTG TTGAGTCTGG GCTATGCAAC TAAATACACG     1500

GCTCGGTCCA AGTGCCTTAC TGAAACTCCC ATAGAATATC TGAGATGGCT GAACCAGCAG     1560

ACCCGATGGA GCAAGTCCTA CTTCCGAGAG TGGCTGTACA ATGCCATGTG GTTTCACAAG     1620

CATCACCTGT GGATGACCTA TGAAGCTGTT ATCACTGGAT TCTTTCCTTT CTTTCTCATT     1680

GCCACAGTCA TCCAGCTCTT CTACAGGGGT AAAATCTGGA ACATCCTCCT CTTCCTGTTA     1740

ACTGTCCAGC TAGTGGGTCT CATCAAGTCA TCTTTTGCCA GCTGCCTTAG AGGAAATATC     1800

GTCATGGTAT TCATGTCTCT GTATTCAGTG TTATACATGT CAAGTCTACT TCCTGCCAAG     1860

ATGTTTGCAA TTGCAACCAT AAACAAAGCT GGGTGGGGCA CATCTGGAAG GAAGACCATT     1920

GTTGTTAATT TCATAGGACT TATTCCAGTG TCCGTGTGGT TTACAATCCT TCTAGGTGGT     1980

GTAATTTTCA CCATTTATAA GGAATCTAAA AAGCCATTTT CCGAATCCAA ACAGACTGTT     2040

CTCATCGTGG GAACTTTGAT CTATGCATGC TACTGGGTCA TGCTTTTGAC TCTCTATGTG     2100

GTTCTCATCA ATAAGTGTGG CAGGCGGAAG AAGGGACAAC AGTATGACAT GGTGCTTGAT     2160

GTATGATGAT GTTTGTAGTC ACACCTGGAG ACACACACAC ACACATCA CACACACACA       2220

CACCTTAGCT CCTCAAGGGG CTATACAGTA TTGTGGCACC GCACCCTGCC ACCACAGGAG     2280

ACATATCACT GCTGCTGGGA CTTGAACAAA GACATTCAAT GGGGGTTGGT TTCTTTTTTA     2340

TTCTGCCAAA GCAAATTGAT ACATCAGTGA GAAGAAAGTC CGATTAAATC TGACAGTTTT     2400

AGGACGGTGG GATGATGTCT TGGCTTATGC ACTTTTCCCT TACTGTGCAT CTGCCTGACA     2460

GTGTTTGTTC TAAATACCTC ACTTGCCATG CTTTGTGTGG GTGATCATGG AAGAAAAGGA     2520

TTCTGAAAAC TCAAGGGAAC GTTCTTTCAA CCTACACATC CTAACTTATG GACTCTTTTG     2580

ATAGCTGATG ATTTTCTTTC TATTTTTTGT TTTTAAGGAA AATTGTTCAT CTTTACCAAA     2640

TGAAATGCCA AAGGAAAGTT GGAAAGCCAC TGGCTATGCT GTATTTTGAT ATAATAATTG     2700

TACTGTGTTT TAAATTTTGT ATCCGGATTT TTAAAAACAA AATTTCACAC CATAGTCTAT     2760

ATTTTACTTC TCTGGCAAAA TACACTTTTG TTCTTTTATA TATATATATA TATATATATA     2820

ATAAAATAGG TTCTAAAAAA ATCCATACTA TAAAAAAAAA TTAACCTGCC CAAAATGTGA     2880

AACGTGGTTG ACTGATGTTC ATGAAAGAAT AAAATGTTTC TCTCTTTCTC TACATTTTAA     2940

AAAAAAA                                                              2947
```

(2) INFORMATION FOR SEQ ID NO:2:

(i) SEQUENCE CHARACTERISTICS:
    (A) LENGTH: 552 amino acids
    (B) TYPE: amino acid
    (C) STRANDEDNESS: single
    (D) TOPOLOGY: linear -continued (ii) MOLECULE TYPE: protein (xi) SEQUENCE DESCRIPTION: SEQ ID NO:2:

```
Met His Cys Glu Arg Phe Leu Cys Val Leu Arg Ile Ile Gly Thr Thr
 1               5                  10                  15
Leu Phe Gly Val Ser Leu Leu Gly Ile Thr Ala Ala Tyr Ile Val
                20                  25                  30
Gly Tyr Gln Phe Ile Gln Thr Asp Asn Tyr Tyr Phe Ser Phe Gly Leu
                35                  40                  45
Tyr Gly Ala Phe Leu Ala Ser His Leu Ile Ile Gln Ser Leu Phe Ala
 50                  55                  60
Phe Leu Glu His Arg Lys Met Lys Lys Ser Leu Glu Thr Pro Ile Lys
65                  70                  75                  80
Leu Asn Lys Thr Val Ala Leu Cys Ile Ala Ala Tyr Gln Glu Asp Pro
                85                  90                  95
Asp Tyr Leu Arg Lys Cys Leu Gln Ser Val Lys Arg Leu Thr Tyr Pro
               100                 105                 110
Gly Ile Lys Val Val Met Val Ile Asp Gly Asn Ser Asp Asp Asp Leu
               115                 120                 125
Tyr Met Met Asp Ile Phe Ser Glu Val Ile Gly Arg Asp Lys Ser Ala
130                 135                 140
Thr Tyr Ile Trp Lys Asn Asn Phe His Glu Lys Gly Pro Gly Glu Thr
145                 150                 155                 160
Glu Glu Ser His Lys Glu Ser Ser Gln His Val Thr Gln Leu Val Leu
                165                 170                 175
Ser Asn Lys Ser Ile Cys Ile Met Gln Lys Trp Gly Gly Lys Arg Glu
                180                 185                 190
Val Met Tyr Thr Ala Phe Arg Ala Leu Gly Arg Ser Val Asp Tyr Val
                195                 200                 205
Gln Val Cys Asp Ser Asp Thr Met Leu Asp Pro Ala Ser Ser Val Glu
210                 215                 220
Met Val Lys Val Leu Glu Glu Asp Pro Met Val Gly Gly Val Gly Gly
225                 230                 235                 240
Asp Val Gln Ile Leu Asn Lys Tyr Asp Ser Trp Ile Ser Phe Leu Ser
                245                 250                 255
Ser Val Arg Tyr Trp Met Ala Phe Asn Ile Glu Arg Ala Cys Gln Ser
                260                 265                 270
Tyr Phe Gly Cys Val Gln Cys Ile Ser Gly Pro Leu Gly Met Tyr Arg
                275                 280                 285
Asn Ser Leu Leu His Glu Phe Val Glu Asp Trp Tyr Asn Gln Glu Phe
290                 295                 300
Met Gly Asn Gln Cys Ser Phe Gly Asp Asp Arg His Leu Thr Asn Arg
305                 310                 315                 320
Val Leu Ser Leu Gly Tyr Ala Thr Lys Tyr Thr Ala Arg Ser Lys Cys
                325                 330                 335
Leu Thr Glu Thr Pro Ile Glu Tyr Leu Arg Trp Leu Asn Gln Gln Thr
                340                 345                 350
Arg Trp Ser Lys Ser Tyr Phe Arg Glu Trp Leu Tyr Asn Ala Met Trp
                355                 360                 365
Phe His Lys His His Leu Trp Met Thr Tyr Glu Ala Val Ile Thr Gly
     370                 375                 380
Phe Phe Pro Phe Phe Leu Ile Ala Thr Val Ile Gln Leu Phe Tyr Arg
385                 390                 395                 400
```

```
Gly Lys Ile Trp Asn Ile Leu Leu Phe Leu Leu Thr Val Gln Leu Val
                    405                 410                 415

Gly Leu Ile Lys Ser Ser Phe Ala Ser Cys Leu Arg Gly Asn Ile Val
                420                 425                 430

Met Val Phe Met Ser Leu Tyr Ser Val Leu Tyr Met Ser Ser Leu Leu
                435                 440                 445

Pro Ala Lys Met Phe Ala Ile Ala Thr Ile Asn Lys Ala Gly Trp Gly
            450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Lys Pro Phe Ser Glu Ser Lys Gln Thr Val Leu
                500                 505                 510

Ile Val Gly Thr Leu Ile Tyr Ala Cys Tyr Trp Val Met Leu Leu Thr
            515                 520                 525

Leu Tyr Val Val Leu Ile Asn Lys Cys Gly Arg Arg Lys Lys Gly Gln
    530                 535                 540

Gln Tyr Asp Met Val Leu Asp Val
545                 550
```

(2) INFORMATION FOR SEQ ID NO:3:

(i) SEQUENCE CHARACTERISTICS:
  (A) LENGTH: 583 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:3:

```
Met Arg Gln Asp Met Pro Lys Pro Ser Glu Ala Ala Arg Cys Cys Ser
1               5                   10                  15

Gly Leu Ala Arg Arg Ala Leu Thr Ile Ile Phe Ala Leu Leu Ile Leu
            20                  25                  30

Gly Leu Met Thr Trp Ala Tyr Ala Ala Gly Val Pro Leu Ala Ser Asp
            35                  40                  45

Arg Tyr Gly Leu Leu Ala Phe Gly Leu Tyr Gly Ala Phe Leu Ser Ala
    50                  55                  60

His Leu Val Ala Gln Ser Leu Phe Ala Tyr Leu Glu His Arg Arg Val
65                  70                  75                  80

Ala Ala Ala Arg Arg Ser Leu Ala Lys Gly Pro Leu Asp Ala Ala
                85                  90                  95

Thr Ala Arg Ser Val Ala Leu Thr Ile Ser Ala Tyr Gln Glu Asp Pro
            100                 105                 110

Ala Tyr Leu Arg Gln Cys Leu Thr Ser Ala Arg Ala Leu Leu Tyr Pro
            115                 120                 125

His Thr Arg Leu Arg Val Leu Met Val Val Asp Gly Asn Arg Ala Glu
        130                 135                 140

Asp Leu Tyr Met Val Asp Met Phe Arg Glu Val Phe Ala Asp Glu Asp
145                 150                 155                 160

Pro Ala Thr Tyr Val Trp Asp Gly Asn Tyr His Gln Pro Trp Glu Pro
                165                 170                 175

Ala Glu Ala Thr Gly Ala Val Gly Glu Gly Ala Tyr Arg Glu Val Glu
            180                 185                 190
```

-continued

```
Ala Glu Asp Pro Gly Arg Leu Ala Val Glu Ala Leu Val Arg Thr Arg
        195                 200                 205
Arg Cys Val Cys Val Ala Gln Arg Trp Gly Gly Lys Arg Glu Val Met
210                 215                 220
Tyr Thr Ala Phe Lys Ala Leu Gly Asp Ser Val Asp Tyr Val Gln Val
225                 230                 235                 240
Cys Asp Ser Asp Thr Arg Leu Asp Pro Met Ala Leu Leu Glu Leu Val
                245                 250                 255
Arg Val Leu Asp Glu Asp Pro Arg Val Gly Ala Val Gly Gly Asp Val
                260                 265                 270
Arg Ile Leu Asn Pro Leu Asp Ser Trp Val Ser Phe Leu Ser Ser Leu
                275                 280                 285
Arg Tyr Trp Val Ala Phe Asn Val Glu Arg Ala Cys Gln Ser Tyr Phe
                290                 295                 300
His Cys Val Ser Cys Ile Ser Gly Pro Leu Gly Leu Tyr Arg Asn Asn
305                 310                 315                 320
Leu Leu Gln Gln Phe Leu Glu Ala Trp Tyr Asn Gln Lys Phe Leu Gly
                325                 330                 335
Thr His Cys Thr Phe Gly Asp Asp Arg His Leu Thr Asn Arg Met Leu
                340                 345                 350
Ser Met Gly Tyr Ala Thr Lys Tyr Thr Ser Arg Ser Arg Cys Tyr Ser
                355                 360                 365
Glu Thr Pro Ser Ser Phe Leu Arg Trp Leu Ser Gln Gln Thr Arg Trp
370                 375                 380
Ser Lys Ser Tyr Phe Arg Glu Trp Leu Tyr Asn Ala Leu Trp Trp His
385                 390                 395                 400
Arg His His Ala Trp Met Thr Tyr Glu Ala Val Val Ser Gly Leu Phe
                405                 410                 415
Pro Phe Phe Val Ala Thr Val Leu Arg Leu Phe Tyr Ala Gly Arg
                420                 425                 430
Pro Trp Ala Leu Leu Trp Val Leu Leu Cys Val Gln Gly Val Ala Leu
                435                 440                 445
Ala Lys Ala Ala Phe Ala Ala Trp Leu Arg Gly Cys Val Arg Met Val
450                 455                 460
Leu Leu Ser Leu Tyr Ala Pro Leu Tyr Met Cys Gly Leu Leu Pro Ala
465                 470                 475                 480
Lys Phe Leu Ala Leu Val Thr Met Asn Gln Ser Gly Trp Gly Thr Ser
                485                 490                 495
Gly Arg Lys Lys Leu Ala Ala Asn Tyr Val Pro Val Leu Pro Leu Ala
                500                 505                 510
Leu Trp Ala Leu Leu Leu Leu Gly Leu Ala Arg Ser Val Ala Gln
                515                 520                 525
Glu Ala Arg Ala Asp Trp Ser Gly Pro Ser Arg Ala Ala Glu Ala Tyr
530                 535                 540
His Leu Ala Ala Gly Ala Gly Ala Tyr Val Ala Tyr Trp Val Val Met
545                 550                 555                 560
Leu Thr Ile Tyr Trp Val Gly Val Arg Arg Leu Cys Arg Arg Arg Ser
                565                 570                 575
Gly Gly Tyr Arg Val Gln Val
                580
```

(2) INFORMATION FOR SEQ ID NO:4:

(i) SEQUENCE CHARACTERISTICS:

(A) LENGTH: 587 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:4:

```
Met Lys Glu Lys Ala Ala Glu Thr Met Glu Ile Pro Glu Gly Ile Pro
 1               5                  10                  15

Lys Asp Leu Glu Pro Lys His Pro Thr Leu Trp Arg Ile Ile Tyr Tyr
             20                  25                  30

Ser Phe Gly Val Val Leu Leu Ala Thr Ile Thr Ala Ala Tyr Val Ala
         35                  40                  45

Glu Phe Gln Val Leu Lys His Glu Ala Ile Leu Phe Ser Leu Gly Leu
 50                  55                  60

Tyr Gly Leu Ala Met Leu Leu His Leu Met Met Gln Ser Leu Phe Ala
 65                  70                  75                  80

Phe Leu Glu Ile Arg Arg Val Asn Lys Ser Glu Leu Pro Cys Ser Phe
                 85                  90                  95

Lys Lys Thr Val Ala Leu Thr Ile Ala Gly Tyr Gln Glu Asn Pro Glu
            100                 105                 110

Tyr Leu Ile Lys Cys Leu Glu Ser Cys Lys Tyr Val Lys Tyr Pro Lys
        115                 120                 125

Asp Lys Leu Lys Ile Ile Leu Val Ile Asp Gly Asn Thr Glu Asp Asp
130                 135                 140

Ala Tyr Met Met Glu Met Phe Lys Asp Val Phe His Gly Glu Asp Val
145                 150                 155                 160

Gly Thr Tyr Val Trp Lys Gly Asn Tyr His Thr Val Lys Lys Pro Glu
                165                 170                 175

Glu Thr Asn Lys Gly Ser Cys Pro Glu Val Ser Lys Pro Leu Asn Glu
            180                 185                 190

Asp Glu Gly Ile Asn Met Val Glu Glu Leu Val Arg Asn Lys Arg Cys
        195                 200                 205

Val Cys Ile Met Gln Gln Trp Gly Lys Arg Glu Val Met Tyr Thr Ala
210                 215                 220

Phe Gln Ala Ile Gly Thr Ser Val Asp Tyr Val Gln Val Cys Asp Ser
225                 230                 235                 240

Asp Thr Lys Leu Asp Glu Leu Ala Thr Val Glu Met Val Lys Val Leu
                245                 250                 255

Glu Ser Asn Asp Met Tyr Gly Ala Val Gly Gly Asp Val Arg Ile Leu
            260                 265                 270

Asn Pro Tyr Asp Ser Phe Ile Ser Phe Met Ser Ser Leu Arg Tyr Trp
        275                 280                 285

Met Ala Phe Asn Val Glu Arg Ala Cys Gln Ser Tyr Phe Asp Cys Val
290                 295                 300

Ser Cys Ile Ser Gly Pro Leu Gly Met Tyr Arg Asn Asn Ile Leu Gln
305                 310                 315                 320

Val Phe Leu Glu Ala Trp Tyr Arg Gln Lys Phe Leu Gly Thr Tyr Cys
                325                 330                 335

Thr Leu Gly Asp Asp Arg His Leu Thr Asn Arg Val Leu Ser Met Gly
            340                 345                 350

Tyr Arg Thr Lys Tyr Thr His Lys Ser Arg Ala Phe Ser Glu Thr Pro
        355                 360                 365

Ser Leu Tyr Leu Arg Trp Leu Asn Gln Gln Thr Arg Trp Thr Lys Ser
```

-continued

```
              370              375              380
Tyr Phe Arg Glu Trp Leu Tyr Asn Ala Gln Trp Trp His Lys His His
385              390              395              400

Ile Trp Met Thr Tyr Glu Ser Val Val Ser Phe Ile Phe Pro Phe Phe
                405              410              415

Ile Thr Ala Thr Val Ile Arg Leu Ile Tyr Ala Gly Thr Ile Trp Asn
                420              425              430

Val Val Trp Leu Leu Leu Cys Ile Gln Ile Met Ser Leu Phe Lys Ser
            435              440              445

Ile Tyr Ala Cys Trp Leu Arg Gly Asn Phe Ile Met Leu Leu Met Ser
        450              455              460

Leu Tyr Ser Met Leu Tyr Met Thr Gly Leu Leu Pro Ser Lys Tyr Phe
465              470              475              480

Ala Leu Leu Thr Leu Asn Lys Thr Gly Trp Gly Thr Ser Gly Arg Lys
                485              490              495

Lys Ile Val Gly Asn Tyr Met Pro Ile Leu Pro Leu Ser Ile Trp Ala
                500              505              510

Ala Val Leu Cys Gly Gly Val Gly Tyr Ser Ile Tyr Met Asp Cys Gln
            515              520              525

Asn Asp Trp Ser Thr Pro Glu Lys Gln Lys Glu Met Tyr His Leu Leu
        530              535              540

Tyr Gly Cys Val Gly Tyr Val Met Tyr Met Val Ile Met Ala Val Met
545              550              555              560

Tyr Trp Val Trp Val Lys Arg Cys Cys Arg Lys Arg Ser Gln Thr Val
                565              570              575

Thr Leu Val His Asp Ile Pro Asp Met Cys Val
                580              585

(2) INFORMATION FOR SEQ ID NO:5:

(i) SEQUENCE CHARACTERISTICS:
        (A) LENGTH: 419 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Pro Ile Phe Lys Lys Thr Leu Ile Val Leu Ser Phe Ile Phe Leu
1               5                10               15

Ile Ser Ile Leu Ile Tyr Leu Asn Met Tyr Leu Phe Gly Thr Ser Thr
                20               25               30

Val Gly Ile Tyr Gly Val Ile Leu Ile Thr Tyr Leu Val Ile Lys Leu
            35               40               45

Gly Leu Ser Phe Leu Tyr Glu Pro Phe Lys Gly Asn Pro His Asp Tyr
    50               55               60

Lys Val Ala Ala Val Ile Pro Ser Tyr Asn Glu Asp Ala Glu Ser Leu
65               70               75               80

Leu Glu Thr Leu Lys Ser Val Leu Ala Gln Thr Tyr Pro Leu Ser Glu
                85               90               95

Ile Tyr Ile Val Asp Asp Gly Ser Ser Asn Thr Asp Ala Ile Gln Leu
                100              105              110

Ile Glu Glu Tyr Val Asn Arg Glu Val Asp Ile Cys Arg Asn Val Ile
            115              120              125

Val His Arg Ser Leu Val Asn Lys Gly Lys Arg His Ala Gln Ala Trp
```

```
            130                 135                 140
Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175

Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
            195                 200                 205

Phe Gly Val Glu Arg Ala Ala Gln Ser Leu Thr Gly Asn Ile Leu Val
            210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
            275                 280                 285

Lys Ser Tyr Leu Lys Gln Gln Asn Arg Trp Asn Lys Ser Phe Phe Arg
            290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
            355                 360                 365

Val His Tyr Met Val Lys His Pro Ala Ser Phe Leu Leu Ser Pro Leu
            370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys (2) INFORMATION FOR SEQ ID NO:6:

(i) SEQUENCE CHARACTERISTICS:
        (A) LENGTH: 426 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Tyr Leu Leu Asp Thr Thr Ser Thr Ala Ala Ile Ser Ile Tyr Ala
1               5                   10                  15

Leu Leu Leu Thr Ala Tyr Arg Ser Met Gln Val Leu Tyr Ala Arg Pro
                20                  25                  30

Ile Asp Gly Leu Ala Val Ala Ala Glu Pro Val Glu Thr Arg Pro Leu
            35                  40                  45

Pro Ala Val Asp Val Ile Val Pro Ser Phe Asn Glu Asp Pro Gly Ile
50                  55                  60
```

```
Leu Ser Ala Cys Leu Ala Ser Ile Ala Asp Gln Asp Tyr Pro Gly Glu
 65                  70                  75                  80

Leu Arg Val Tyr Val Val Asp Asp Gly Ser Arg Asn Arg Glu Ala Ile
                 85                  90                  95

Val Arg Val Arg Ala Phe Tyr Ser Arg Asp Pro Arg Phe Ser Phe Ile
            100                 105                 110

Leu Leu Pro Glu Asn Val Gly Lys Arg Lys Ala Gln Ile Ala Ala Ile
            115                 120                 125

Gly Gln Ser Ser Gly Asp Leu Val Leu Asn Val Asp Ser Asp Ser Thr
        130                 135                 140

Ile Ala Phe Asp Val Val Ser Lys Leu Ala Ser Lys Met Arg Asp Pro
145                 150                 155                 160

Glu Val Gly Ala Val Met Gly Gln Leu Thr Ala Ser Asn Ser Gly Asp
                165                 170                 175

Thr Trp Leu Thr Lys Leu Ile Asp Met Glu Tyr Trp Leu Ala Cys Asn
            180                 185                 190

Glu Glu Arg Ala Ala Gln Ser Arg Phe Gly Ala Val Met Cys Cys Cys
            195                 200                 205

Gly Pro Cys Ala Met Tyr Arg Arg Ser Ala Leu Ala Ser Leu Leu Asp
210                 215                 220

Gln Tyr Glu Thr Gln Leu Phe Arg Gly Lys Pro Ser Asp Phe Gly Glu
225                 230                 235                 240

Asp Arg His Leu Thr Ile Leu Met Leu Lys Ala Gly Phe Arg Thr Glu
                245                 250                 255

Tyr Val Pro Asp Ala Ile Val Ala Thr Val Val Pro Asp Thr Leu Lys
                260                 265                 270

Pro Tyr Leu Arg Gln Gln Leu Arg Trp Ala Arg Ser Thr Phe Arg Asp
            275                 280                 285

Thr Phe Leu Ala Leu Pro Leu Leu Arg Gly Leu Ser Pro Phe Leu Ala
            290                 295                 300

Phe Asp Ala Val Gly Gln Asn Ile Gly Gln Leu Leu Leu Ala Leu Ser
305                 310                 315                 320

Val Val Thr Gly Leu Ala His Leu Ile Met Thr Ala Thr Val Pro Trp
                325                 330                 335

Trp Thr Ile Leu Ile Ile Ala Cys Met Thr Ile Ile Arg Cys Ser Val
            340                 345                 350

Val Ala Leu His Ala Arg Gln Leu Arg Phe Leu Gly Phe Val Leu His
            355                 360                 365

Thr Pro Ile Asn Leu Phe Leu Ile Leu Pro Leu Lys Ala Tyr Ala Leu
            370                 375                 380

Cys Thr Leu Ser Asn Ser Asp Trp Leu Ser Arg Tyr Ser Ala Pro Glu
385                 390                 395                 400

Val Pro Val Ser Gly Gly Lys Gln Thr Pro Ile Gln Thr Ser Gly Arg
                405                 410                 415

Val Thr Pro Asp Cys Thr Cys Ser Gly Glu
                420                 425
```

(2) INFORMATION FOR SEQ ID NO:7:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Lys Arg Glu Val Met Tyr Thr Ala Phe Arg Ala Leu Gly Arg Ser Val
1               5                   10                  15

Asp Tyr Val Gln Val Cys Asp Ser Asp Thr Met Leu Asp Pro Ala Ser
                20                  25                  30

Ser Val Glu Met Val Lys Val Leu Glu Glu Asp
            35                  40

(2) INFORMATION FOR SEQ ID NO:8:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Gln Cys Ser Phe Gly Asp Asp Arg His Leu Thr Asn Arg Val Leu Ser
1               5                   10                  15

Leu Gly Tyr Ala Thr Lys Tyr Thr Ala Arg Ser Lys Cys Leu Thr Glu
                20                  25                  30

Thr Pro Ile Glu Tyr Leu Arg Trp Leu Asn Gln Gln Thr Arg Trp Ser
            35                  40                  45

Lys Ser Tyr Phe Arg Glu Trp
50                  55

(2) INFORMATION FOR SEQ ID NO:9:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Lys Arg Glu Val Met Tyr Thr Ala Phe Lys Ala Leu Gly Asp Ser Val
1               5                   10                  15

Asp Tyr Val Gln Val Cys Asp Ser Asp Thr Arg Leu Asp Pro Met Ala
                20                  25                  30

Leu Leu Glu Leu Val Arg Val Leu Asp Glu Asp
            35                  40

(2) INFORMATION FOR SEQ ID NO:10:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Lys Arg Glu Val Met Tyr Thr Ala Phe Gln Ala Ile Gly Thr Ser Val
1               5                   10                  15

Asp Tyr Val Gln Val Cys Asp Ser Asp Thr Lys Leu Asp Glu Leu Ala
                20                  25                  30

```
Thr Val Glu Met Val Lys Val Leu Glu Ser Asn
        35                  40
```

(2) INFORMATION FOR SEQ ID NO:11:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Lys Arg His Ala Gln Ala Trp Ala Phe Glu Arg Ser Asp Ala Asp Val
 1               5                  10                  15
Phe Leu Thr Val Asp Ser Asp Thr Tyr Ile Tyr Pro Asn Ala Leu Glu
                20                  25                  30
Glu Leu Leu Lys Ser Phe Asn Asp Glu
        35                  40
```

(2) INFORMATION FOR SEQ ID NO:12:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Lys Arg Lys Ala Gln Ile Ala Ala Ile Gly Gln Ser Ser Gly Asp Leu
 1               5                  10                  15
Val Leu Asn Val Asp Ser Asp Ser Thr Ile Ala Phe Asp Val Val Ser
                20                  25                  30
Lys Leu Ala Ser Lys Met Arg Asp Pro
        35                  40
```

(2) INFORMATION FOR SEQ ID NO:13:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Lys Lys Lys Ile Asn Ser His Arg Trp Leu Phe Asn Ala Phe Cys Pro
 1               5                  10                  15
Val Leu Gln Pro Thr Val Val Thr Leu Val Asp Val Gly Thr Arg Leu
                20                  25                  30
Asn Asn Thr Ala Ile Tyr Arg Leu Trp Lys Val Phe Asp Met Asp
        35                  40                  45
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ala Phe Asn Val Glu Arg Ala Cys Gln
 1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gly Asp Asp Arg His Leu Thr Asn
 1               5

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Gln Gln Thr Arg Trp Thr Lys Ser Tyr Phe
 1               5                   10

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:17:

GCNTTYAAYG TNGARMGNGC NTGYCA                                              26

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:18:

RTTNGTNARR TGNCKRTCRT CNCC                                                24

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:19:

RAARTANSWY TTNGTCCANC KNGTYTGYTG                                30

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Gly Trp Gly Thr Ser Gly Arg Lys
 1               5

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:21:

CCCGGGCAAG ATGGATTGTG AGAGGTTTCT ATGTGTCCTG                     40

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:22:

CCCGGGTCAT ACATCAAGCA CCATGTCATA CTG                            33

(2) INFORMATION FOR SEQ ID NO:23:

(i) SEQUENCE CHARACTERISTICS:
        (A) LENGTH: 235 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:23:

GTCTTATTTT GGGTGTGTTC AGTGCATTAG TGGACCTCTG GGAATGTACA GAAACTCCTT    60

GTTGCATGAG TTTGTGGAAG ATTGGTACAA TCAAGAATTT ATGGGCAACC AATGTAGCTT   120

TGGTGATGAC AGGCATCTCA CGAACCGGGT GCTGAGCCTG GGCTATGCAA CAAAATACAC   180

AGCTCGATCT AAGTGCCTTA CTGAAACACC TATAGAATAT CTCAGATGGC TAAAC        235

(2) INFORMATION FOR SEQ ID NO:24:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Ser Tyr Phe Gly Cys Val Gln Cys Ile Ser Gly Pro Leu Gly Met Tyr
1               5                   10                  15

Arg Asn Ser Leu Leu Gln Gln Phe Leu Glu Asp Trp Tyr His Gln Lys
                20                  25                  30

Phe Leu Gly Ser Lys Cys Ser Phe Gly Asp Asp Arg His Leu Thr Asn
            35                  40                  45

Arg Val Leu Ser Leu Gly Tyr Arg Thr Lys Tyr Thr Ala Arg Ser Lys
    50                  55                  60

Cys Leu Thr Glu Thr Pro Thr Lys Tyr Leu Arg Trp Leu Asn
65                  70                  75

(2) INFORMATION FOR SEQ ID NO:25:

(i) SEQUENCE CHARACTERISTICS:
        (A) LENGTH: 235 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:25:

GTCCTACTTT GGCTGTGTGC AGTGTATTAG TGGGCCCTTG GGCATGTACC GCAACAGCCT    60

CCTCCAGCAG TTCCTGGAGG ACTGGTACCA TCAGAAGTTC CTAGGCAGCA AGTGCAGCTT   120

CGGGGATGAC CGGCACCTCA CCAACCGAGT CCTGAGCCTT GGCTACCGAA CTAAGTATAC   180

CGCGCGCTCC AAGTGCCTCA CAGAGACCCC CACTAAGTAC CTCCGGTGGC TCAAC        235

(2) INFORMATION FOR SEQ ID NO:26:

(i) SEQUENCE CHARACTERISTICS:
        (A) LENGTH: 235 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:26:

GTCCTACTTT GGCTGTGTGC AATGTATTAG TGGGCCTTTG GGCATGTACC GCAACAGCCT    60

CCTTCAGCAG TTCCTGGAGG ATTGGTACCA TCAGAAGTTC CTAGGCAGCA AGTGCAGCTT   120

TGGGGATGAT CGGCACCTTA CCAACCGAGT CCTGAGTCTT GGCTACCGGA CTAAGTATAC   180

AGCACGCTCT AAGTGCCTCA CAGAGACCCC CACTAGGTAC CTTCGATGGC TCAAT        235

(2) INFORMATION FOR SEQ ID NO:27:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Ser Tyr Phe Gly Cys Val Gln Cys Ile Ser Gly Pro Leu Gly Met Tyr
1               5                   10                  15

Arg Asn Ser Leu Leu Gln Gln Phe Leu Glu Asp Trp Tyr His Gln Lys

```
                    20                  25                  30

Phe Leu Gly Ser Lys Cys Ser Phe Gly Asp Asp Arg His Leu Thr Asn
            35                  40                  45

Arg Val Leu Ser Leu Gly Tyr Arg Thr Lys Tyr Thr Ala Arg Ser Lys
 50                  55                  60

Cys Leu Thr Glu Thr Pro Thr Lys Tyr Leu Arg Trp Leu Asn
65                  70                  75
```

(2) INFORMATION FOR SEQ ID NO:28:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Ser Tyr Phe Gly Cys Val Gln Cys Ile Ser Gly Pro Leu Gly Met Tyr
 1               5                  10                  15

Arg Asn Ser Leu Leu Gln Gln Phe Leu Glu Asp Trp Tyr His Gln Lys
            20                  25                  30

Phe Leu Gly Ser Lys Cys Ser Phe Gly Asp Asp Arg His Leu Thr Asn
            35                  40                  45

Arg Val Leu Ser Leu Gly Tyr Arg Thr Lys Tyr Thr Ala Arg Ser Lys
 50                  55                  60

Cys Leu Thr Glu Thr Pro Thr Arg Tyr Leu Arg Trp Leu Asn
65                  70                  75
```

(2) INFORMATION FOR SEQ ID NO:29:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Ser Tyr Phe Gly Cys Val Gln Cys Ile Ser Gly Pro Leu Gly Met Tyr
 1               5                  10                  15

Arg Asn Ser Leu Leu Gln Gln Phe Leu Glu Asp Trp Tyr His Gln Lys
            20                  25                  30

Phe Leu Gly Ser Lys Cys Ser Phe Gly Asp Asp Arg His Leu Thr Asn
            35                  40                  45

Arg Val Leu Ser Leu Gly Tyr Arg Thr Lys Tyr Thr Ala Arg Ser Lys
 50                  55                  60

Cys Leu Thr Glu Thr Pro Thr Lys Tyr Leu Arg Trp Leu Asn Gln Gln
65                  70                  75                  80

Thr Arg Trp Ser Lys Ser Tyr Phe Arg Glu Trp Leu Tyr Asn Ser Leu
            85                  90                  95

Trp Phe His Lys His His Leu Trp Met Thr Tyr Glu Ser Val Val Thr
            100                 105                 110

Gly Phe Phe Pro Phe Phe Leu Ile Ala Thr Val Ile Gln Leu Phe Tyr
            115                 120                 125

Arg Gly Arg Ile Trp Asn Ile Leu Leu Phe Leu Thr Val Gln Leu
            130                 135                 140
```

```
Val Gly Ile Ile Lys Ala Thr Tyr Ala Cys Phe Leu Arg Gly Asn Ala
145                 150                 155                 160

Glu Met Ile Phe Met Ser Tyr Leu Ser Leu Leu Tyr Met Ser Ser Leu
                165                 170                 175

Leu Pro Ala Lys Ile Phe Ala Ile Ala Thr Ile Asn Lys Ser
            180                 185                 190
```

(2) INFORMATION FOR SEQ ID NO:30:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Ser Tyr Phe Gly Cys Val Gln Cys Ile Ser Gly Pro Leu Gly Met Tyr
1               5                   10                  15

Arg Asn Ser Leu Leu Gln Gln Phe Leu Glu Asp Trp Tyr His Gln Lys
                20                  25                  30

Phe Leu Gly Ser Lys Cys Ser Phe Gly Asp Asp Arg His Leu Thr Asn
            35                  40                  45

Arg Val Leu Ser Leu Gly Tyr Arg Thr Lys Tyr Thr Ala Arg Ser Lys
50                  55                  60

Cys Leu Thr Glu Thr Pro Thr Arg Tyr Leu Arg Trp Leu Asn Gln Gln
65                  70                  75                  80

Thr Arg Trp Ser Lys Ser Tyr Phe Arg Glu Trp Leu Tyr Asn Ser Leu
                85                  90                  95

Trp Phe His Lys His His Leu Trp Met Thr Tyr Glu Ser Val Val Thr
                100                 105                 110

Gly Phe Phe Pro Phe Phe Leu Ile Ala Thr Val Ile Gln Leu Phe Tyr
            115                 120                 125

Arg Gly Arg Ile Trp Asn Ile Leu Leu Phe Leu Leu Thr Val Gln Leu
130                 135                 140

Val Gly Ile Ile Lys Ala Thr Tyr Ala Cys Phe Leu Arg Gly Asn Ala
145                 150                 155                 160

Glu Met Ile Phe Met Ser Tyr Leu Ser Leu Leu Tyr Met Ser Ser Leu
                165                 170                 175

Leu Pro Ala Lys Ile Phe Ala Ile Ala Thr Ile Asn Lys Ser
            180                 185                 190
```

(2) INFORMATION FOR SEQ ID NO:31:

(i) SEQUENCE CHARACTERISTICS:
        (A) LENGTH: 1665 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: Coding Sequence
        (B) LOCATION: 1...1662
        (D) OTHER INFORMATION:

(xi) SEQUENCE DESCRIPTION: SEQ ID NO:31:

```
ATG CCG GTG CAG CTG ACT ACA GCC CTG CGT GTG GTG GGC ACC AGT CTG    48
Met Pro Val Gln Leu Thr Thr Ala Leu Arg Val Val Gly Thr Ser Leu
1               5                   10                  15
```

-continued

| | | |
|---|---|---|
| TTT GCC CTG GTA GTG CTG GGA GGC ATC CTG GCG GCC TAT GTG ACA GGC<br>Phe Ala Leu Val Val Leu Gly Gly Ile Leu Ala Ala Tyr Val Thr Gly<br>20                          25                          30 | 96 |
| TAC CAG TTT ATC CAC ACA GAA AAG CAC TAC CTG TCC TTT GGC CTC TAC<br>Tyr Gln Phe Ile His Thr Glu Lys His Tyr Leu Ser Phe Gly Leu Tyr<br>     35                      40                      45 | 144 |
| GGT GCC ATC CTG GGT CTA CAT CTG CTC ATC CAG AGC CTG TTT GCC TTC<br>Gly Ala Ile Leu Gly Leu His Leu Leu Ile Gln Ser Leu Phe Ala Phe<br>50                          55                          60 | 192 |
| CTG GAG CAC CGT CGA ATG CGC AGG GCA GGG CGC CCC CTC AAG CTG CAC<br>Leu Glu His Arg Arg Met Arg Arg Ala Gly Arg Pro Leu Lys Leu His<br>65                          70                      75                      80 | 240 |
| TGC TCC CAG AGG TCG CGT TCA GTG GCA CTC TGC ATT GCT GCC TAC CAA<br>Cys Ser Gln Arg Ser Arg Ser Val Ala Leu Cys Ile Ala Ala Tyr Gln<br>     85                      90                      95 | 288 |
| GAG GAC CCC GAA TAC CTG CGC AAG TGC CTT CGC TCA GCT CAG CGC ATT<br>Glu Asp Pro Glu Tyr Leu Arg Lys Cys Leu Arg Ser Ala Gln Arg Ile<br>100                        105                    110 | 336 |
| GCC TTT CCA AAC CTC AAG GTG GTC ATG GTA GTG GAT GGC AAT CGC CAG<br>Ala Phe Pro Asn Leu Lys Val Val Met Val Val Asp Gly Asn Arg Gln<br>            115                    120                    125 | 384 |
| GAA GAT ACC TAC ATG TTG GAC ATC TTC CAT GAG GTG CTG GGT GGC ACT<br>Glu Asp Thr Tyr Met Leu Asp Ile Phe His Glu Val Leu Gly Gly Thr<br>130                        135                    140 | 432 |
| GAG CAA GCT GGC TTC TTT GTG TGG CGT AGC AAT TTC CAT GAG GCG GGT<br>Glu Gln Ala Gly Phe Phe Val Trp Arg Ser Asn Phe His Glu Ala Gly<br>145                        150                    155                    160 | 480 |
| GAA GGA GAG ACA GAG GCC AGC CTG CAG GAA GGC ATG GAG CGT GTG CGA<br>Glu Gly Glu Thr Glu Ala Ser Leu Gln Glu Gly Met Glu Arg Val Arg<br>                    165                    170                    175 | 528 |
| GCT GTG GTG TGG GCC AGC ACC TTC TCA TGC ATC ATG CAG AAG TGG GGG<br>Ala Val Val Trp Ala Ser Thr Phe Ser Cys Ile Met Gln Lys Trp Gly<br>                180                    185                    190 | 576 |
| GGC AAG CGT GAG GTC ATG TAC ACT GCC TTC AAG GCC CTT GGC AAC TCA<br>Gly Lys Arg Glu Val Met Tyr Thr Ala Phe Lys Ala Leu Gly Asn Ser<br>195                        200                    205 | 624 |
| GTG GAC TAC ATC CAG GTG TGT GAC TCT GAC ACT GTG CTG GAC CCA GCC<br>Val Asp Tyr Ile Gln Val Cys Asp Ser Asp Thr Val Leu Asp Pro Ala<br>210                        215                    220 | 672 |
| TGC ACC ATT GAG ATG CTT CGA GTC TTG GAA GAA GAT CCC CAA GTA GGA<br>Cys Thr Ile Glu Met Leu Arg Val Leu Glu Glu Asp Pro Gln Val Gly<br>225                        230                    235                    240 | 720 |
| GGT GTT GGA GGA GAT GTC CAA ATC CTC AAC AAG TAT GAT TCA TGG ATC<br>Gly Val Gly Gly Asp Val Gln Ile Leu Asn Lys Tyr Asp Ser Trp Ile<br>                245                    250                    255 | 768 |
| TCC TTC CTG AGC AGT GTG AGG TAC TGG ATG GCT TTC AAC GTG GAG CGG<br>Ser Phe Leu Ser Ser Val Arg Tyr Trp Met Ala Phe Asn Val Glu Arg<br>            260                    265                    270 | 816 |
| GCC TGC CAG TCC TAC TTT GGC TGT GTG CAA TGT ATT AGT GGG CCT TTG<br>Ala Cys Gln Ser Tyr Phe Gly Cys Val Gln Cys Ile Ser Gly Pro Leu<br>275                        280                    285 | 864 |
| GGC ATG TAC CGC AAC AGC CTC CTT CAG CAG TTC CTG GAG GAT TGG TAC<br>Gly Met Tyr Arg Asn Ser Leu Leu Gln Gln Phe Leu Glu Asp Trp Tyr<br>290                        295                    300 | 912 |
| CAT CAG AAG TTC CTA GGC AGC AAG TGC AGC TTT GGG GAT GAT CGG CAC<br>His Gln Lys Phe Leu Gly Ser Lys Cys Ser Phe Gly Asp Asp Arg His<br>305                        310                    315                    320 | 960 |
| CTT ACC AAC CGA GTC CTG AGT CTT GGC TAC CGG ACT AAG TAT ACA GCA<br>Leu Thr Asn Arg Val Leu Ser Leu Gly Tyr Arg Thr Lys Tyr Thr Ala | 1008 |

-continued

```
                  325                 330                 335
CGC TCT AAG TGC CTC ACA GAG ACC CCC ACT AGG TAC CTT CGA TGG CTC    1056
Arg Ser Lys Cys Leu Thr Glu Thr Pro Thr Arg Tyr Leu Arg Trp Leu
            340                 345                 350

AAT CAG CAA ACC CGC TGG AGC AAG TCT TAC TTT CGG GAA TGG CTC TAC    1104
Asn Gln Gln Thr Arg Trp Ser Lys Ser Tyr Phe Arg Glu Trp Leu Tyr
            355                 360                 365

AAT TCT CTG TGG TTC CAT AAG CAC CAC CTC TGG ATG ACC TAT GAA TCA    1152
Asn Ser Leu Trp Phe His Lys His His Leu Trp Met Thr Tyr Glu Ser
            370                 375                 380

GTG GTC ACA GGT TTC TTC CCA TTC TTC CTC ATT GCT ACA GTC ATA CAA    1200
Val Val Thr Gly Phe Phe Pro Phe Phe Leu Ile Ala Thr Val Ile Gln
385                 390                 395                 400

CTT TTC TAC CGT GGC CGC ATC TGG AAC ATT CTC CTC TTC CTG CTA ACA    1248
Leu Phe Tyr Arg Gly Arg Ile Trp Asn Ile Leu Leu Phe Leu Leu Thr
                405                 410                 415

GTG CAG CTG GTG GGC ATT ATC AAG GCT ACC TAT GCC TGC TTC CTT CGA    1296
Val Gln Leu Val Gly Ile Ile Lys Ala Thr Tyr Ala Cys Phe Leu Arg
                420                 425                 430

GGC AAT GCA GAG ATG ATC TTC ATG TCC CTC TAC TCC CTT CTC TAT ATG    1344
Gly Asn Ala Glu Met Ile Phe Met Ser Leu Tyr Ser Leu Leu Tyr Met
            435                 440                 445

TCC AGC CTC TTG CCA GCC AAG ATC TTT GCT ATT GCT ACC ATC AAC AAG    1392
Ser Ser Leu Leu Pro Ala Lys Ile Phe Ala Ile Ala Thr Ile Asn Lys
450                 455                 460

TCT GGC TGG GGC ACT TCT GGC AGG AAA ACC ATT GTC GTG AAC TTC ATT    1440
Ser Gly Trp Gly Thr Ser Gly Arg Lys Thr Ile Val Val Asn Phe Ile
465                 470                 475                 480

GGC CTA ATC CCC GTG TCC ATC TGG GTG GCA GTT CTT CTA GGG GGG TTA    1488
Gly Leu Ile Pro Val Ser Ile Trp Val Ala Val Leu Leu Gly Gly Leu
                485                 490                 495

GCC TAC ACA GCT TAT TGC CAG GAC CTG TTC AGT GAG ACC GAG CTA GCC    1536
Ala Tyr Thr Ala Tyr Cys Gln Asp Leu Phe Ser Glu Thr Glu Leu Ala
                500                 505                 510

TTC CTA GTC TCT GGG GCC ATC CTG TAT GGC TGC TAC TGG GTG GCC CTC    1584
Phe Leu Val Ser Gly Ala Ile Leu Tyr Gly Cys Tyr Trp Val Ala Leu
            515                 520                 525

CTC ATG CTG TAT CTG GCC ATT ATT GCC CGG AGG TGT GGG AAG AAG CCA    1632
Leu Met Leu Tyr Leu Ala Ile Ile Ala Arg Arg Cys Gly Lys Lys Pro
530                 535                 540

GAA CAG TAT AGC CTG GCT TTT GCG GAG GTG TGA                        1665
Glu Gln Tyr Ser Leu Ala Phe Ala Glu Val
545                 550
```

(2) INFORMATION FOR SEQ ID NO:32:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:32:

```
Met Pro Val Gln Leu Thr Thr Ala Leu Arg Val Val Gly Thr Ser Leu
1               5                   10                  15

Phe Ala Leu Val Val Leu Gly Gly Ile Leu Ala Ala Tyr Val Thr Gly
                20                  25                  30
```

```
Tyr Gln Phe Ile His Thr Glu Lys His Tyr Leu Ser Phe Gly Leu Tyr
         35                  40                  45
Gly Ala Ile Leu Gly Leu His Leu Leu Ile Gln Ser Leu Phe Ala Phe
     50                  55                  60
Leu Glu His Arg Arg Met Arg Arg Ala Gly Arg Pro Leu Lys Leu His
 65                  70                  75                  80
Cys Ser Gln Arg Ser Arg Ser Val Ala Leu Cys Ile Ala Ala Tyr Gln
                 85                  90                  95
Glu Asp Pro Glu Tyr Leu Arg Lys Cys Leu Arg Ser Ala Gln Arg Ile
                100                 105                 110
Ala Phe Pro Asn Leu Lys Val Val Met Val Val Asp Gly Asn Arg Gln
            115                 120                 125
Glu Asp Thr Tyr Met Leu Asp Ile Phe His Glu Val Leu Gly Gly Thr
        130                 135                 140
Glu Gln Ala Gly Phe Phe Val Trp Arg Ser Asn Phe His Glu Ala Gly
145                 150                 155                 160
Glu Gly Glu Thr Glu Ala Ser Leu Gln Glu Gly Met Glu Arg Val Arg
                165                 170                 175
Ala Val Val Trp Ala Ser Thr Phe Ser Cys Ile Met Gln Lys Trp Gly
            180                 185                 190
Gly Lys Arg Glu Val Met Tyr Thr Ala Phe Lys Ala Leu Gly Asn Ser
        195                 200                 205
Val Asp Tyr Ile Gln Val Cys Asp Ser Asp Thr Val Leu Asp Pro Ala
210                 215                 220
Cys Thr Ile Glu Met Leu Arg Val Leu Glu Glu Asp Pro Gln Val Gly
225                 230                 235                 240
Gly Val Gly Gly Asp Val Gln Ile Leu Asn Lys Tyr Asp Ser Trp Ile
                245                 250                 255
Ser Phe Leu Ser Ser Val Arg Tyr Trp Met Ala Phe Asn Val Glu Arg
            260                 265                 270
Ala Cys Gln Ser Tyr Phe Gly Cys Val Gln Cys Ile Ser Gly Pro Leu
        275                 280                 285
Gly Met Tyr Arg Asn Ser Leu Leu Gln Gln Phe Leu Glu Asp Trp Tyr
        290                 295                 300
His Gln Lys Phe Leu Gly Ser Lys Cys Ser Phe Gly Asp Asp Arg His
305                 310                 315                 320
Leu Thr Asn Arg Val Leu Ser Leu Gly Tyr Arg Thr Lys Tyr Thr Ala
                325                 330                 335
Arg Ser Lys Cys Leu Thr Glu Thr Pro Thr Arg Tyr Leu Arg Trp Leu
            340                 345                 350
Asn Gln Gln Thr Arg Trp Ser Lys Ser Tyr Phe Arg Glu Trp Leu Tyr
        355                 360                 365
Asn Ser Leu Trp Phe His Lys His His Leu Trp Met Thr Tyr Glu Ser
    370                 375                 380
Val Val Thr Gly Phe Phe Pro Phe Phe Leu Ile Ala Thr Val Ile Gln
385                 390                 395                 400
Leu Phe Tyr Arg Gly Arg Ile Trp Asn Ile Leu Phe Leu Leu Thr
                405                 410                 415
Val Gln Leu Val Gly Ile Ile Lys Ala Thr Tyr Ala Cys Phe Leu Arg
            420                 425                 430
Gly Asn Ala Glu Met Ile Phe Met Ser Leu Tyr Ser Leu Leu Tyr Met
        435                 440                 445
Ser Ser Leu Leu Pro Ala Lys Ile Phe Ala Ile Ala Thr Ile Asn Lys
```

```
                  450                 455                 460
Ser Gly Trp Gly Thr Ser Gly Arg Lys Thr Ile Val Val Asn Phe Ile
465                 470                 475                 480

Gly Leu Ile Pro Val Ser Ile Trp Val Ala Val Leu Leu Gly Gly Leu
                485                 490                 495

Ala Tyr Thr Ala Tyr Cys Gln Asp Leu Phe Ser Glu Thr Glu Leu Ala
                500                 505                 510

Phe Leu Val Ser Gly Ala Ile Leu Tyr Gly Cys Tyr Trp Val Ala Leu
                515                 520                 525

Leu Met Leu Tyr Leu Ala Ile Ile Ala Arg Arg Cys Gly Lys Lys Pro
530                 535                 540

Glu Gln Tyr Ser Leu Ala Phe Ala Glu Val
545                 550
```

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
Arg Trp Leu Asn Gln Gln Thr Arg Trp
1               5
```

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:34:

```
TACTGGATGG CTTTCAACGT GGAG                                      24
```

(2) INFORMATION FOR SEQ ID NO:35:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Lys Arg Glu Val Met Tyr Thr Ala Phe Lys Ala Leu Gly Asn Ser Val
1               5                   10                  15

Asp Tyr Ile Gln Val Cys Asp Ser Asp Thr Val Leu Asp Pro Ala Cys
                20                  25                  30

Thr Ile Glu Met Leu Arg Val Leu Glu Glu Asp
            35                  40
```

(2) INFORMATION FOR SEQ ID NO:36:

(i) SEQUENCE CHARACTERISTICS:
        (A) LENGTH: 55 amino acids
        (B) TYPE: amino acid (C) STRANDEDNESS: single
            (D) TOPOLOGY: linear (ii) MOLECULE TYPE: peptide (xi) SEQUENCE DESCRIPTION: SEQ ID NO:36:

Lys Cys Ser Phe Gly Asp Asp Arg His Leu Thr Asn Arg Val Leu Ser
1               5                   10                  15

Leu Gly Tyr Arg Thr Lys Tyr Thr Ala Arg Ser Lys Cys Leu Thr Glu
            20                  25                  30

Thr Pro Thr Arg Tyr Leu Arg Trp Leu Asn Gln Gln Thr Arg Trp Ser
        35                  40                  45

Lys Ser Tyr Phe Arg Glu Trp
    50                  55

(2) INFORMATION FOR SEQ ID NO:37:

(i) SEQUENCE CHARACTERISTICS:
            (A) LENGTH: 24 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:37:

GTCATCCAGA GGTGGTGCTT ATGG                                              24

(2) INFORMATION FOR SEQ ID NO:38:

(i) SEQUENCE CHARACTERISTICS:
            (A) LENGTH: 35 base pairs
            (B) TYPE: nucleic acid
            (C) STRANDEDNESS: unknown
            (D) TOPOLOGY: unknown (ii) MOLECULE TYPE: cDNA (xi) SEQUENCE DESCRIPTION: SEQ ID NO:38:

CCGAATTCAA GATGGCGGTG CAGCTGACTA CAGCC                                  35

(2) INFORMATION FOR SEQ ID NO:39:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:39:

CCGAATTCTC ACACCTCCGC AAAAGCCAGG C                                      31

(2) INFORMATION FOR SEQ ID NO:40:

(i) SEQUENCE CHARACTERISTICS:
            (A) LENGTH: 55 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:40:

His Cys Thr Phe Gly Asp Asp Arg His Leu Thr Asn Arg Met Leu Ser
1               5                   10                  15

Met Gly Tyr Ala Thr Lys Tyr Thr Ser Arg Ser Arg Cys Tyr Ser Glu
            20                  25                  30

Thr Pro Ser Ser Phe Leu Arg Trp Leu Ser Gln Gln Thr Arg Trp Ser
            35                  40                  45

Lys Ser Tyr Phe Arg Glu Trp
            50                  55

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:41:

TGTGCAGTGT AATTAGTGGG CCCT                                    24

(2) INFORMATION FOR SEQ ID NO:42:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

Tyr Cys Thr Leu Gly Asp Asp Arg His Leu Thr Asn Arg Val Leu Ser
 1               5                  10                  15

Met Gly Tyr Arg Thr Lys Tyr Thr His Lys Ser Arg Ala Phe Ser Glu
            20                  25                  30

Thr Pro Ser Leu Tyr Leu Arg Trp Leu Asn Gln Gln Thr Arg Trp Thr
            35                  40                  45

Lys Ser Tyr Phe Arg Glu Trp
            50                  55

(2) INFORMATION FOR SEQ ID NO:43:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:43:

GTTGAGCCAC CGGAGGTACT TAG                                     23

(2) INFORMATION FOR SEQ ID NO:44:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Pro Val Ser Ile Gly Asp Asp Arg Cys Leu Thr Asn Tyr Ala Ile Asp

```
            1               5              10              15
Leu Gly Arg Thr Val Tyr Gln Ser Thr Ala Arg Cys Asp Thr Asp Val
                    20                  25                  30

Pro Phe Gln Leu Lys Ser Tyr Leu Lys Gln Gln Asn Arg Trp Asn Lys
            35                  40                  45

Ser Phe Phe Arg Glu Ser
            50
```

(2) INFORMATION FOR SEQ ID NO:45:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Asn Met Tyr Leu Ala Glu Asp Arg Ile Leu Cys Trp Glu Leu Val Ala
 1               5                  10                  15

Lys Arg Asp Ala Lys Trp Val Leu Lys Tyr Val Lys Glu Ala Thr Gly
            20                  25                  30

Glu Thr Asp Val Pro Glu Asp Val Ser Glu Phe Ile Ser Gln Arg Arg
            35                  40                  45

Arg Trp Leu Asn Cys Ala Met Phe Ala Ala
            50                  55
```

(2) INFORMATION FOR SEQ ID NO:46:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Pro Ser Asp Phe Gly Glu Asp Arg His Leu Thr Ile Leu Met Leu Lys
 1               5                  10                  15

Ala Gly Phe Arg Thr Glu Tyr Val Pro Asp Ala Ile Val Ala Thr Val
            20                  25                  30

Val Pro Asp Thr Leu Lys Pro Tyr Leu Arg Gln Gln Leu Arg Trp Ala
            35                  40                  45

Arg Ser Thr Phe Arg Asp Thr
            50                  55
```

(2) INFORMATION FOR SEQ ID NO:47:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Lys Ala Gly Ala Glu Asn Ala Leu Val Arg Val Ser Ala Val Leu Thr
 1               5                  10                  15

Asn Ala Pro Phe Ile Leu Asn Leu Asp Cys Asp His Tyr Val Asn Asn
            20                  25                  30
```

```
Ser Lys Ala Val Arg Glu Ala Met Cys Phe Leu Met Asp
        35                  40                  45
```

(2) INFORMATION FOR SEQ ID NO:48:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Tyr Gly Ser Val Thr Glu Asp Ile Leu Thr Gly Phe Lys Met His Cys
 1               5                  10                  15

Arg Gly Trp Arg Ser Ile Tyr Cys Met Pro Leu Arg Pro Ala Phe Lys
            20                  25                  30

Gly Ser Ala Pro Ile Asn Leu Ser Asp Arg Leu His Gln Val Leu Arg
        35                  40                  45

Trp Ala Leu Gly Ser Val Glu Ile Phe
    50                  55
```

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

GTGCTTCTGT CTCTCTACGC G                                  21

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

CCAGTCCCAA TATAGTCCAG ACTG                           24

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

GGTGTGTTCA GTGCATTAGT GGA                            23

(2) INFORMATION FOR SEQ ID NO:52:

(i) SEQUENCE CHARACTERISTICS:
        (A) LENGTH: 25 base pairs

-continued

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

TAGCCATCTG AGATATTCTA TAGGT                                              25

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

GTCAGAGCTA CTTCCACTGT G                                                  21

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

AAGGAGGAGG GCGTCTCCGA G                                                  21
```